(12) United States Patent
Fuchiwaki

(10) Patent No.: US 10,538,538 B2
(45) Date of Patent: Jan. 21, 2020

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventor: Junta Fuchiwaki, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 205 days.

(21) Appl. No.: 15/831,674

(22) Filed: Dec. 5, 2017

(65) Prior Publication Data

US 2018/0201632 A1 Jul. 19, 2018

(30) Foreign Application Priority Data

Jan. 13, 2017 (KR) .................. 10-2017-0006413

(51) Int. Cl.
| | | |
|---|---|---|
| H01L 51/50 | (2006.01) | |
| C07F 7/10 | (2006.01) | |
| C09K 11/06 | (2006.01) | |
| H01L 51/00 | (2006.01) | |
| C07F 7/08 | (2006.01) | |

(52) U.S. Cl.
CPC .............. *C07F 7/10* (2013.01); *C07F 7/0816* (2013.01); *C09K 11/06* (2013.01); *H01L 51/0059* (2013.01); *H01L 51/0072* (2013.01); *H01L 51/0094* (2013.01); *C09K 2211/1096* (2013.01); *H01L 51/5056* (2013.01)

(58) Field of Classification Search
None
See application file for complete search history.

(56) References Cited

U.S. PATENT DOCUMENTS

| | | |
|---|---|---|
| 8,384,068 B2 | 2/2013 | Kahle et al. |
| 9,537,105 B2 | 1/2017 | Pflumm et al. |
| 2010/0171417 A1 | 7/2010 | Kitamura et al. |

(Continued)

FOREIGN PATENT DOCUMENTS

| | | |
|---|---|---|
| JP | 2001-244076 A | 9/2001 |
| KR | 10-2014-0000639 A | 1/2014 |
| KR | 10-1381505 B1 | 3/2014 |

(Continued)

*Primary Examiner* — Gregory D Clark
(74) *Attorney, Agent, or Firm* — Lewis Roca Rothgerber Christie LLP

(57) ABSTRACT

A polycyclic compound is represented by Formula 1,

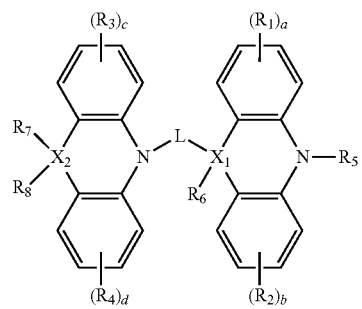

[Formula 1]

where $X_1$, $X_2$, L, $R_1$ to $R_8$, and a to d are as defined in the specification.

20 Claims, 2 Drawing Sheets

(56) References Cited

U.S. PATENT DOCUMENTS

2015/0188056 A1    7/2015   Suda
2018/0148462 A1*   5/2018   Fuchiwaki ............ C07F 7/0816

FOREIGN PATENT DOCUMENTS

| KR | 10-1506919 B1 | 3/2015 |
| KR | 10-2015-0033700 A | 4/2015 |
| KR | 10-1559430 B1 | 10/2015 |
| KR | 10-1577468 B1 | 12/2015 |
| KR | 10-2018-0037645 A | 4/2018 |
| WO | WO 2007/110228 A1 | 10/2007 |
| WO | WO 2010/050778 A1 | 5/2010 |
| WO | WO 2010/050781 A1 | 5/2010 |
| WO | WO 2015/068987 A1 | 5/2015 |

* cited by examiner

POLYCYCLIC COMPOUND AND ORGANIC ELECTROLUMINESCENCE DEVICE INCLUDING THE SAME

CROSS-REFERENCE TO RELATED APPLICATIONS

Korean Patent Application No. 10-2017-0006413, filed on Jan. 13, 2017, in the Korean Intellectual Property Office, and entitled: "Polycyclic Compound and Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

Development relating to organic electroluminescence displays as an image display is being actively conducted. An organic electroluminescence display is different from a liquid crystal display in that it is a self-luminescent display that accomplishes display by recombining holes and electrons injected from a first electrode and a second electrode in an emission layer and emitting light from a luminescent material which includes an organic compound in the emission layer.

As an organic electroluminescence device, for example, an organic electroluminescence device composed of a first electrode, a hole transport layer disposed on the first electrode, an emission layer disposed on the hole transport layer, an electron transport layer disposed on the emission layer, and a second electrode disposed on the electron transport layer is known. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light by radiation deactivation of the excitons. In addition, the configuration of an organic electroluminescence device is not limited to those described above, and various modifications may be possible.

In an application of an organic electroluminescence device to a display, the decrease of a driving voltage, increase of emission efficiency and extension of life for the organic electroluminescence device are required, and the development of materials which may stably implement these requirements in an organic electroluminescence is also continuously required.

SUMMARY

Embodiments are directed to a polycyclic compound represented by the following Formula 1:

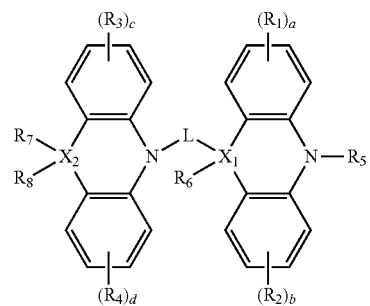

[Formula 1]

where $X_1$ and $X_2$ are each independently any one of C, Si, Ge, or Sn, L is a substituted or unsubstituted arylene group having 6 to 30 ring carbon atoms, or a substituted or unsubstituted heteroarylene group having 2 to 30 ring carbon atoms, $R_1$ to $R_4$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_5$ is a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_6$ to $R_8$ are each independently a substituted or unsubstituted alkyl group having 1 to 20 carbon atoms, a substituted or unsubstituted alkoxy group having 1 to 20 carbon atoms, a substituted or unsubstituted aryloxy group having 6 to 30 ring carbon atoms, a substituted or unsubstituted aryl group having 6 to 30 ring carbon atoms, or a substituted or unsubstituted heteroaryl group having 2 to 30 ring carbon atoms, or $R_6$ to $R_8$ may form a ring by combining adjacent groups with each other, and a to d are each independently an integer of 1 to 4.

At least one of $X_1$ or $X_2$ may be Si.

One of $X_1$ or $X_2$ may be any one of Si, Ge, or Sn, and the other one of $X_1$ or $X_2$ is C.

L may be a substituted or unsubstituted phenylene group, or a substituted or unsubstituted divalent biphenyl group.

L may be represented by any one of the following L-1 to L-4:

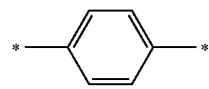

L-1

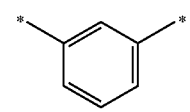

L-2

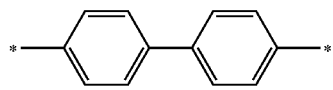

L-3

-continued

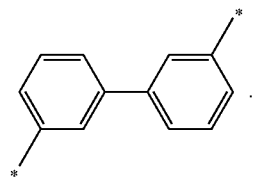
L-4

L may be a substituted or unsubstituted heteroarylene group including one of N, O, or S as a hetero atom.

L may be represented by one of the following L-5 to L-7:

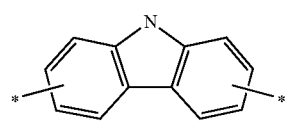
L-5

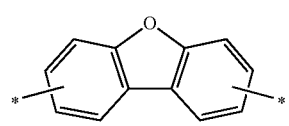
L-6

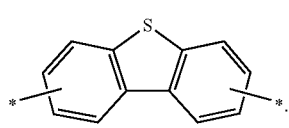
L-7

$R_5$ may be a methyl group, or a substituted or unsubstituted phenyl group.

$R_6$ may be a methyl group, or a substituted or unsubstituted phenyl group.

$R_7$ and $R_8$ may each independently be a methyl group, or a substituted or unsubstituted phenyl group, or may combine with each other to form a substituted or unsubstituted fluorene ring.

The polycyclic compound represented by Formula 1 may be any one of compounds represented in the following Compound Group 1:

[Compound Group 1]

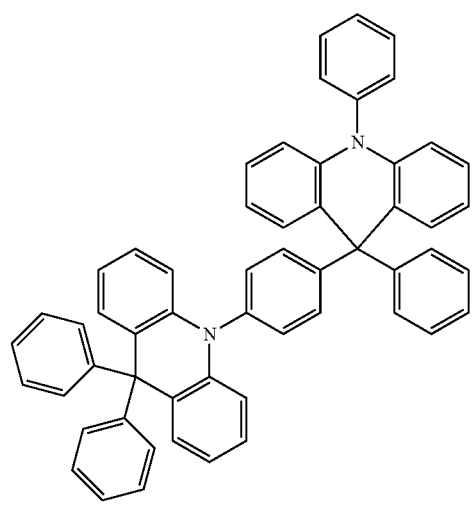
1

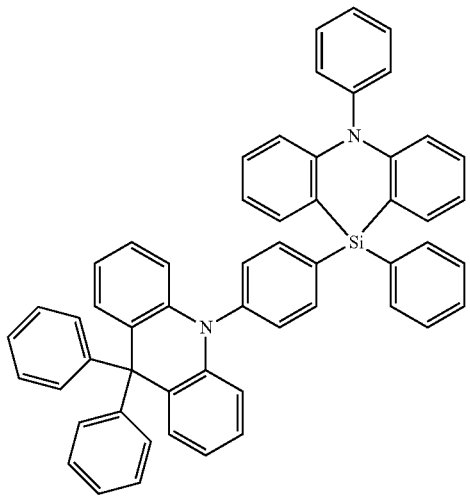
2

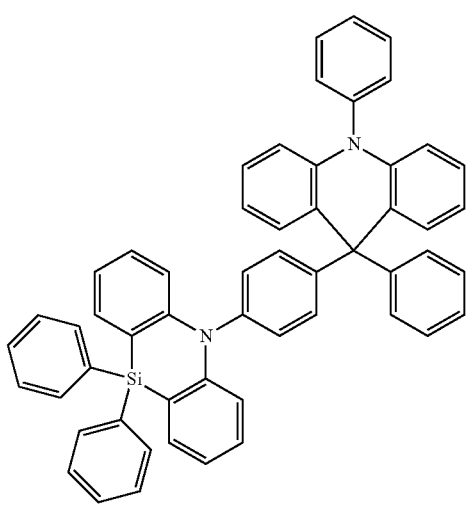
3

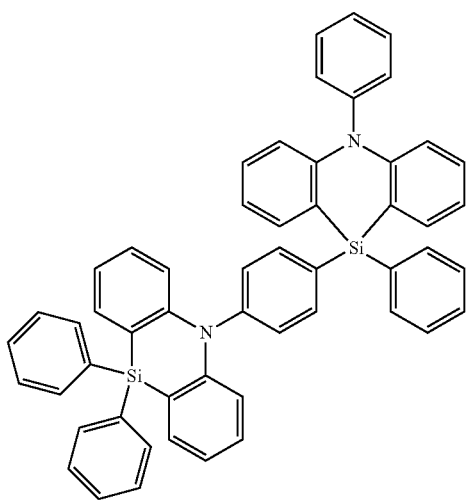
4

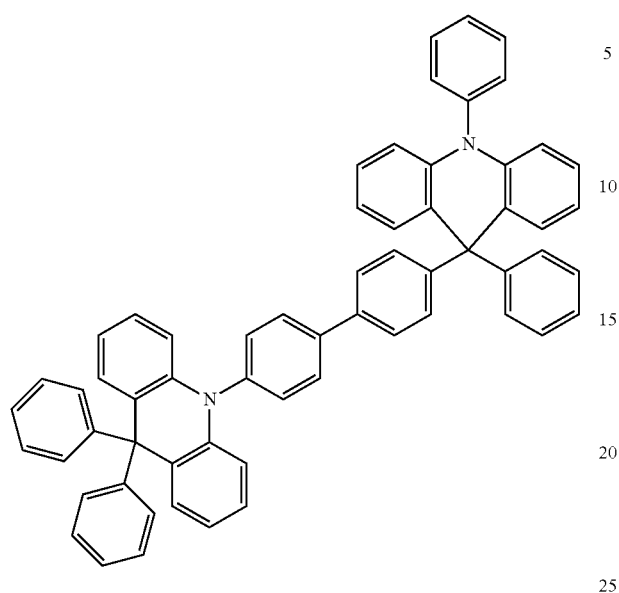
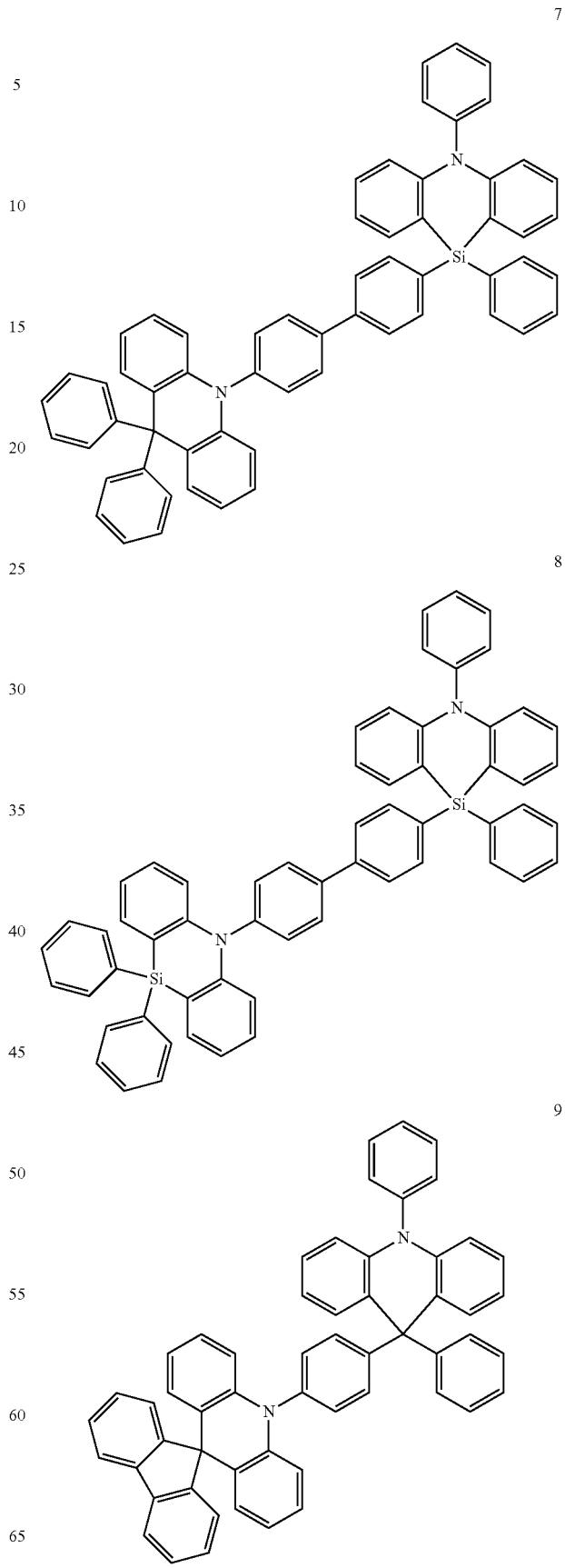

10
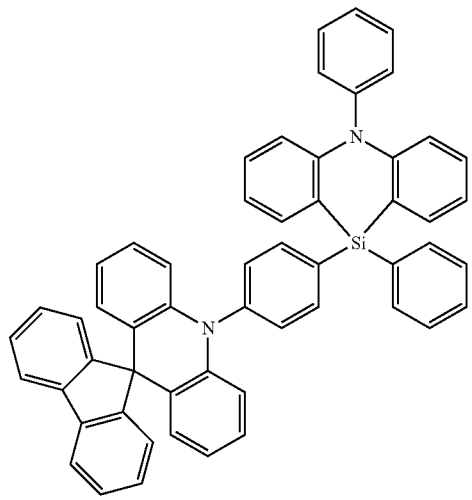
11
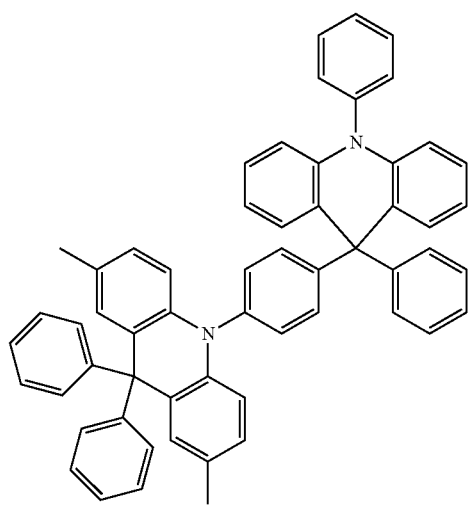
12
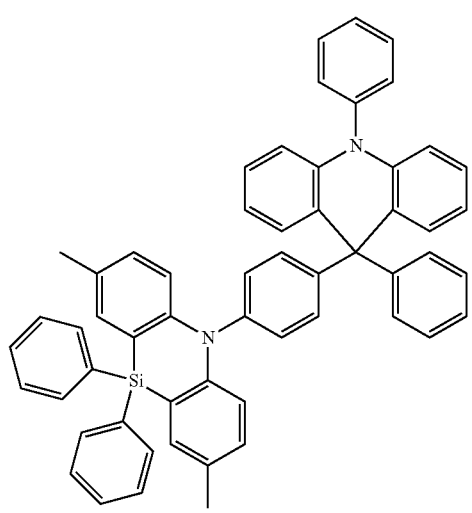
13
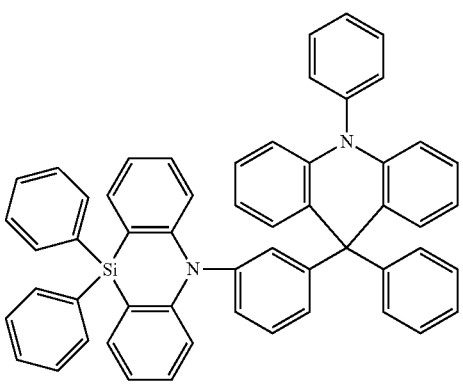
14
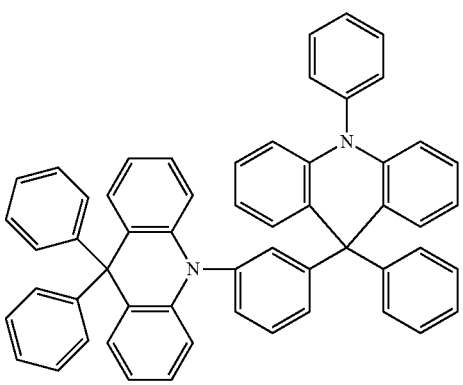
15
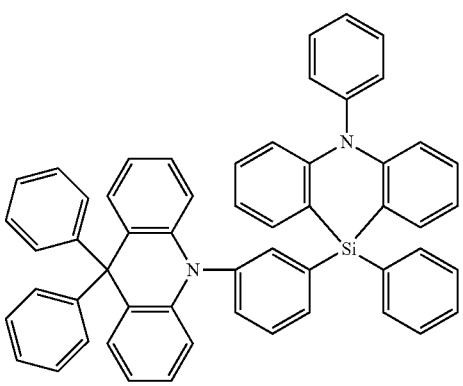
16

17
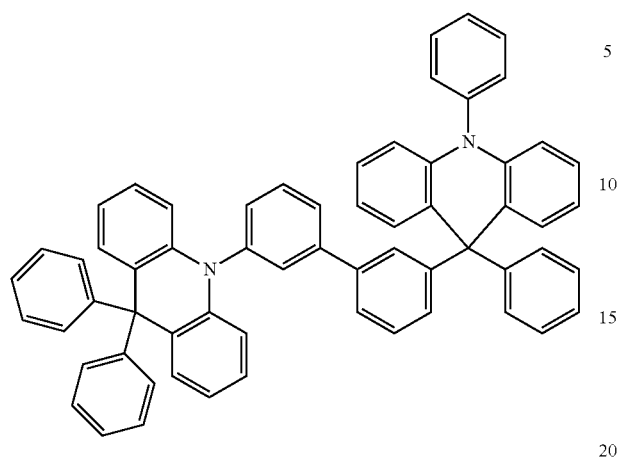
18
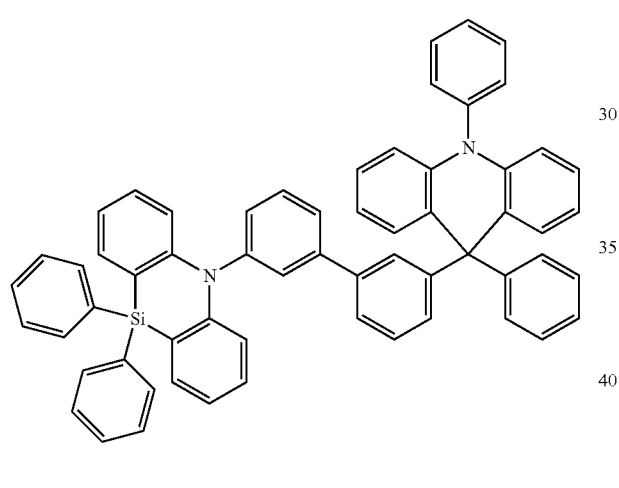
19
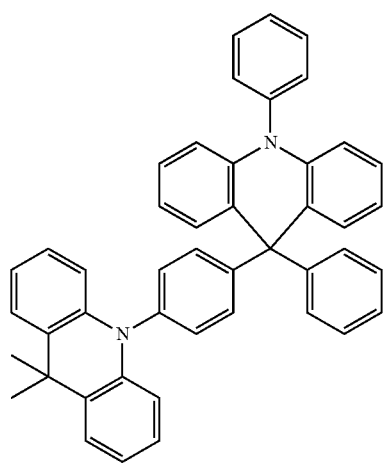
20
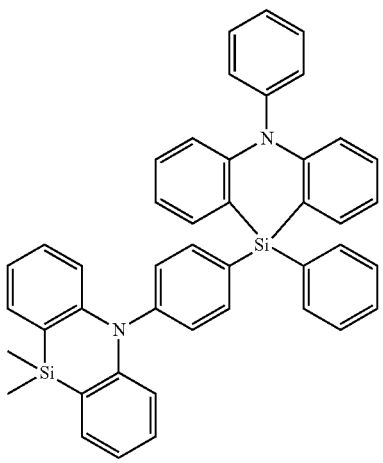
21
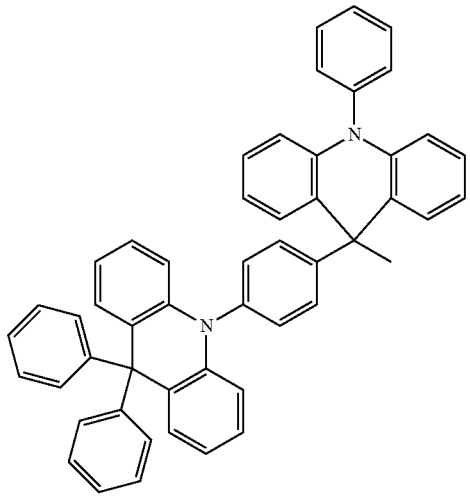
22
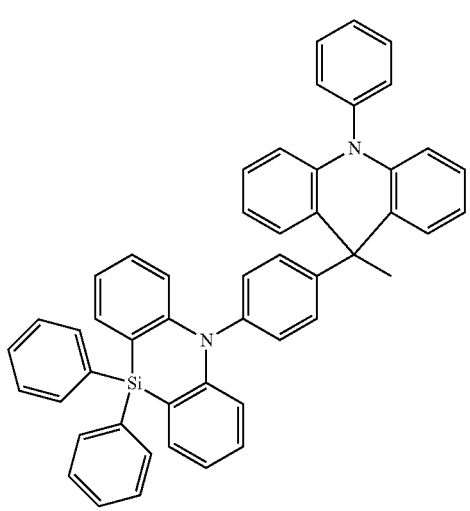

23
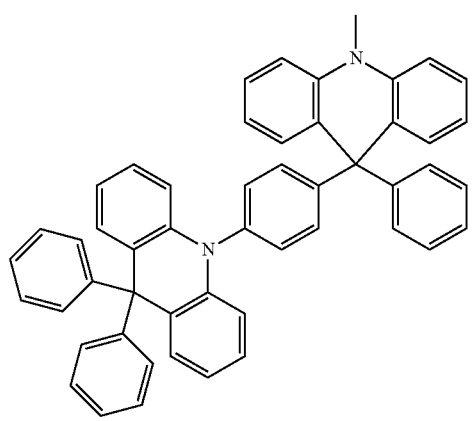
24
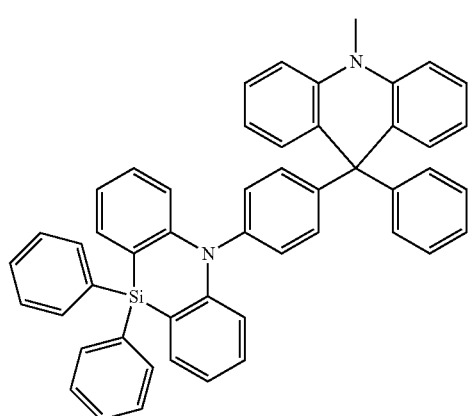
25
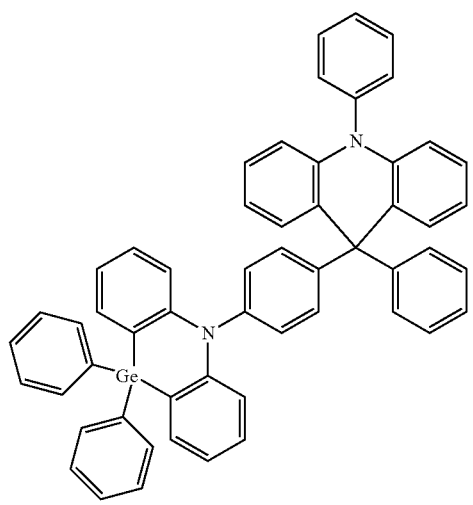
26
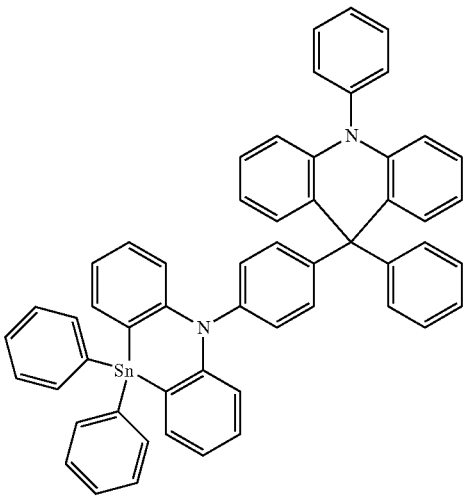
27
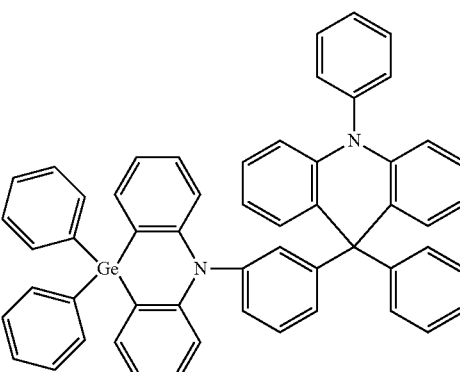
28
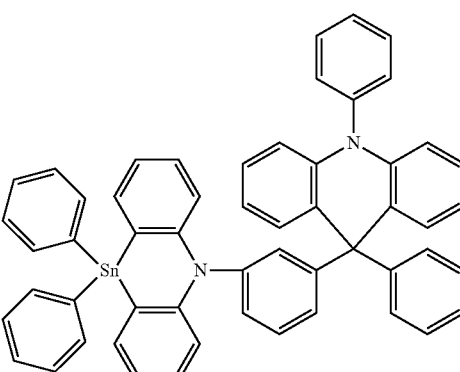
29
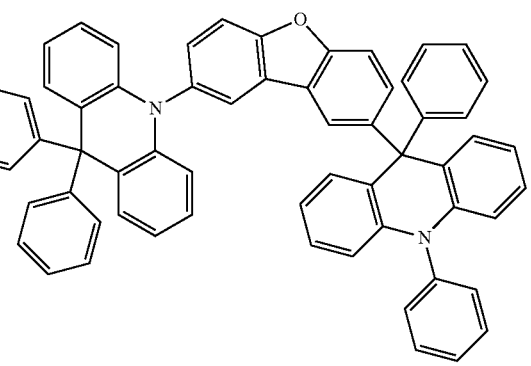

30
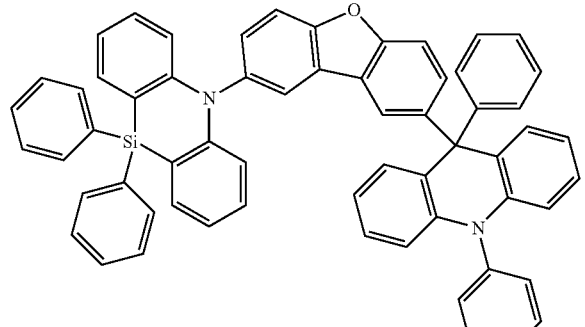
31
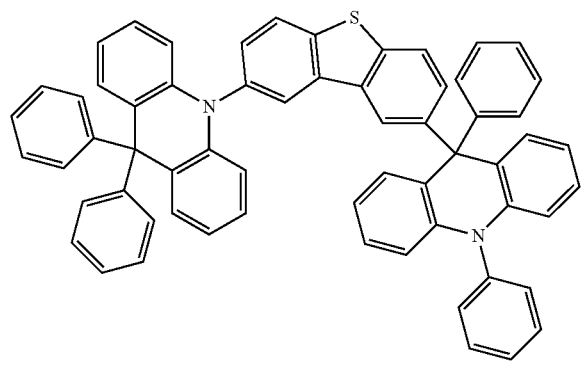
32
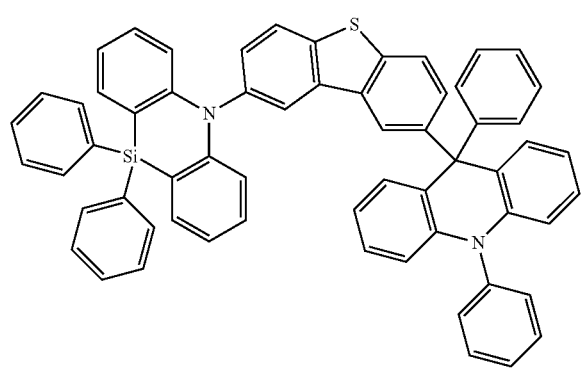
33
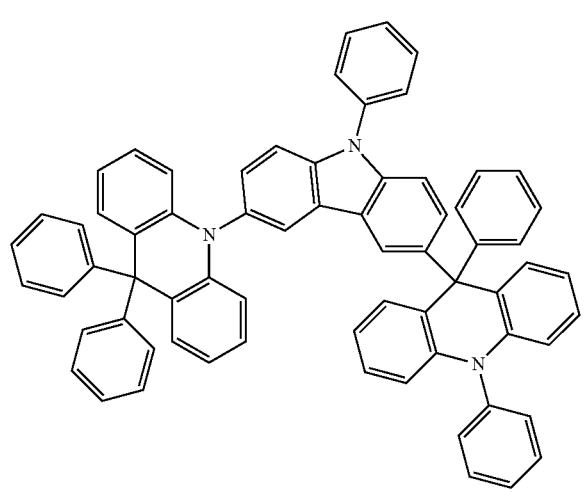
34
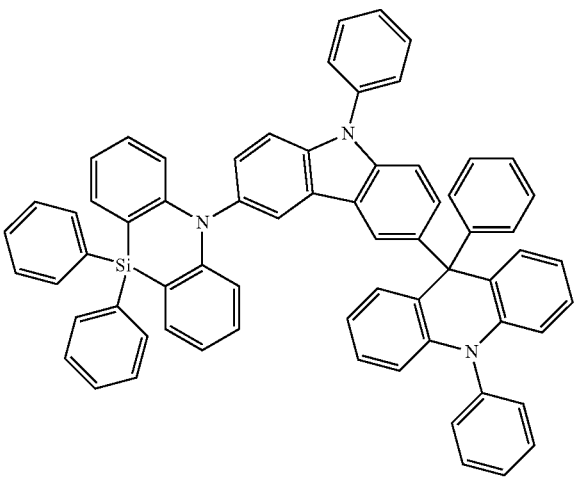
35
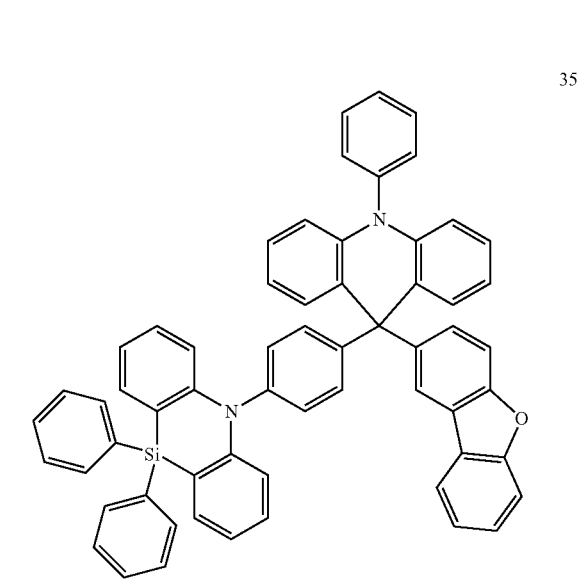
36
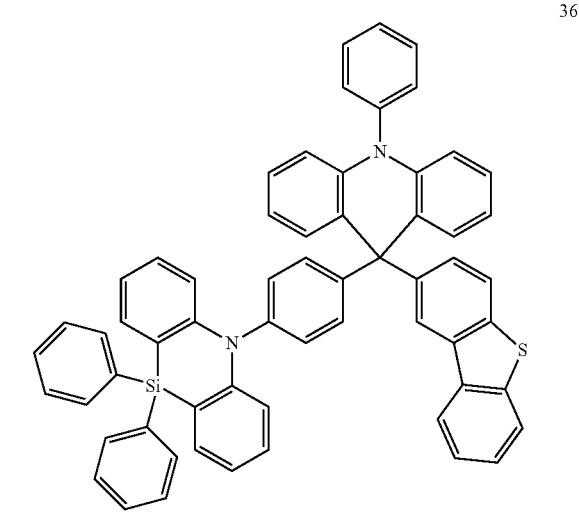

37

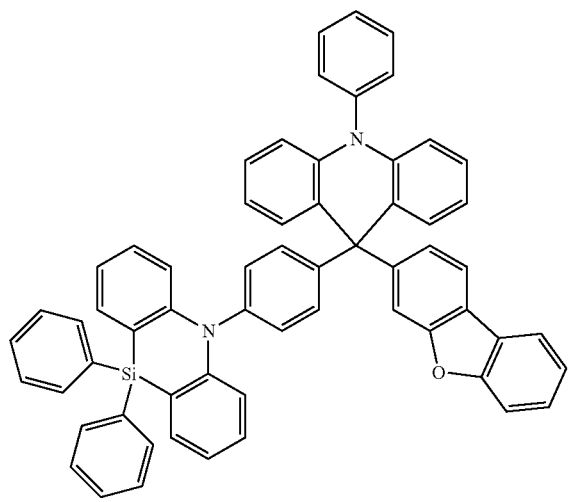

38

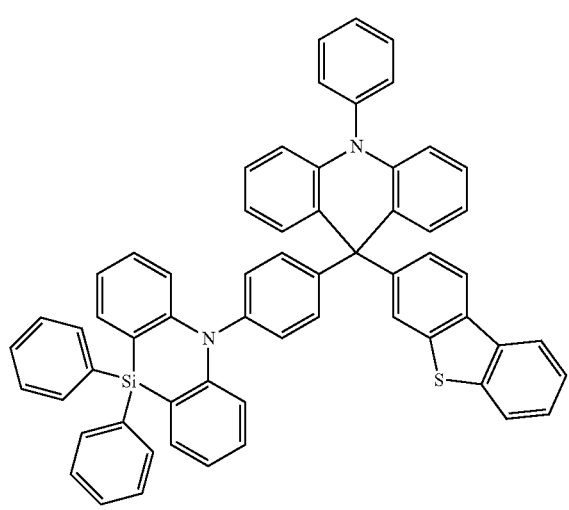

39

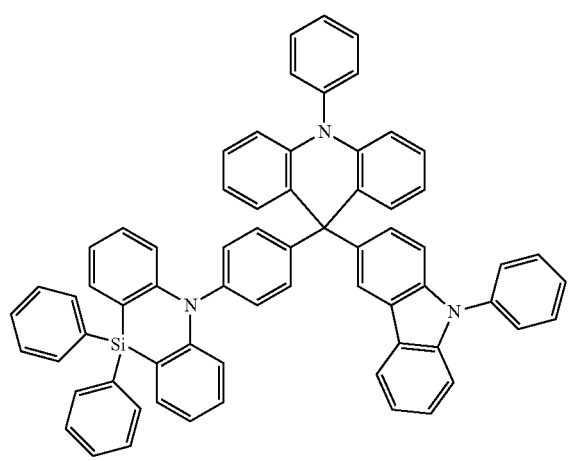

40

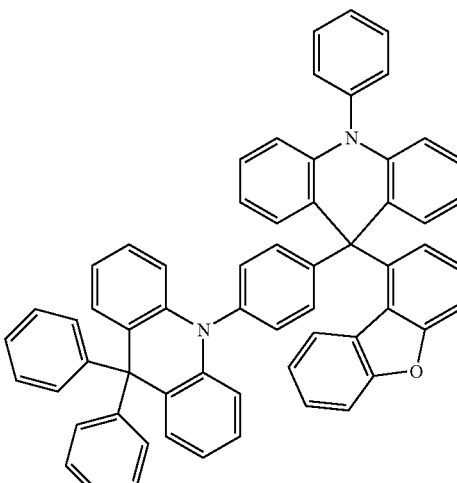

41

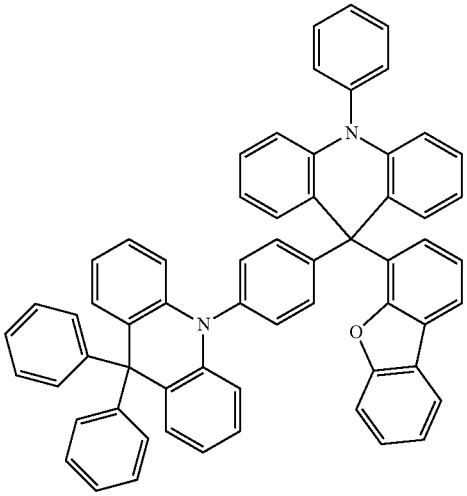

42

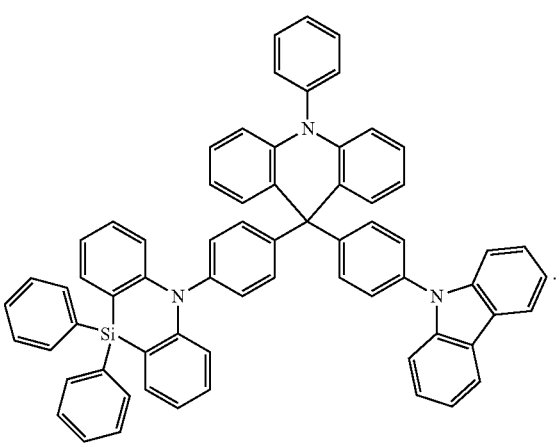

Embodiments are also directed to an organic electroluminescence device including a first electrode, a hole transport region on the first electrode, an emission layer on the hole transport region, an electron transport region disposed on the emission layer, and a second electrode on the electron transport region, wherein the hole transport region includes the polycyclic compound represented by Formula 1, as described above.

The hole transport region may include a hole injection layer and a hole transport layer between the hole injection layer and the emission layer, a the hole transport layer includes the polycyclic compound represented by Formula 1.

The hole transport region may include a hole injection layer, a hole transport layer on the hole injection layer, and an electron blocking layer between the hole transport layer and the emission layer, wherein the electron blocking layer includes the polycyclic compound represented by Formula 1.

The emission layer may emit blue light.

BRIEF DESCRIPTION OF THE FIGURES

Features will become apparent to those of skill in the art by describing in detail exemplary embodiments with reference to the attached drawings in which.

DETAILED DESCRIPTION

Figure 1:
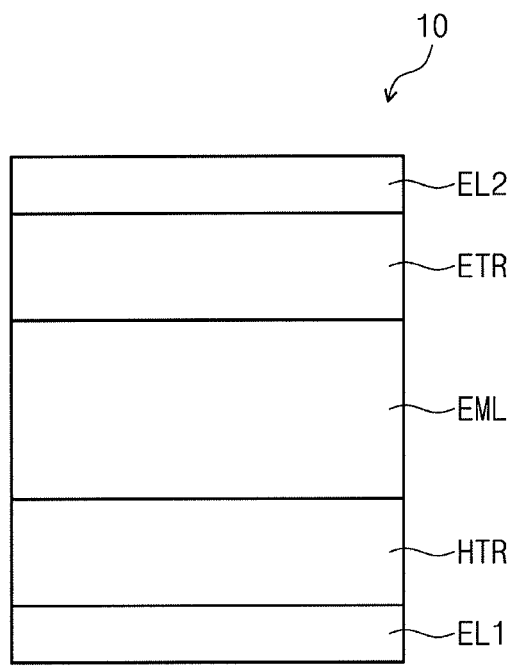
FIG. 1 illustrates a schematic cross-sectional view of an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference characters refer to like elements throughout.

In the present disclosure, ——* indicates a bond with an atom of an adjacent group.

In the present disclosure, "substituted or unsubstituted" may refer to a group being unsubstituted or substituted with at least one substituent, the at least one substituent being one of deuterium, a halogen, a nitro group, an amino group, a silyl group, boron, phosphine oxide, phosphine sulfide, an alkyl group, an alkenyl group, an aryl group, and a heterocycle group. In addition, in some instances, the substituents illustrated above may be substituted or unsubstituted. For example, a biphenyl group may be interpreted as an aryl group, or as a phenyl group substituted with phenyl group.

In the present disclosure, "forming a ring by combining adjacent groups with each other" may refer to forming a substituted or unsubstituted hydrocarbon ring or a substituted or unsubstituted heterocycle by combining adjacent groups with each other. The hydrocarbon ring may be an aliphatic hydrocarbon ring or an aromatic hydrocarbon ring. The term "heterocycle" includes an aliphatic heterocyclic group and an aromatic heterocyclic group. The hydrocarbon ring and heterocyclic group may be a monocyclic group or a polycyclic group. In addition, the ring formed by combining adjacent groups with each other may be connected with another ring to form a spiro structure.

In the present disclosure, the term "an adjacent group" may refer to a substituent at an atom that is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, a halogen atom may be, for example, a fluorine atom, a chlorine atom, a bromine atom, or an iodine atom.

In the present disclosure, the alkyl group may have a linear, branched or cyclic form. The carbon number of the alkyl group may be 1 to 50, 1 to 30, 1 to 20, 1 to 10 or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., groups.

In the present disclosure, the term "aryl group" refers to a functional group or substituent derived from an aromatic hydrocarbon ring. The aryl group may be a monocyclic aryl group or a polycyclic aryl group. The ring carbon number of the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylene, pyrenyl, benzofluoranthenyl, chrysenyl, etc., groups.

In the present disclosure, the fluorenyl group may be substituted, and two substituents may be combined with each other to form a spiro structure.

In the present disclosure, the heteroaryl group may include at least one of O, N, P, Si or S as a heteroatom. The ring carbon number of the heteroaryl group may be 2 to 30, or 2 to 20. The heteroaryl group may be a monoheteroaryl group or polycyclic heteroaryl group. The polycyclic heteroaryl group may have, for example, bicyclic or tricyclic structure. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilol, dibenzofuranyl, etc., groups.

In the present disclosure, the explanation regarding aryl groups may be applied to arylene groups, except that an arylene group is divalent.

In the present disclosure, the explanation regarding heteroaryl groups may be applied to heteroarylene groups, except that a heteroarylene is divalent.

In the present disclosure, the carbon number of the amino group is not specifically limited, and may be 1 to 30. The amino group may include alkyl amino and aryl amino groups. Examples of the amino group may include methylamino, dimethylamino, phenylamino, diphenylamino, naphthylamino, 9-methyl-anthracenylamino, triphenylamino, etc., groups.

Hereinafter, the polycyclic compound according to an embodiment will be explained.

The polycyclic compound according to an embodiment is represented by the following Formula 1.

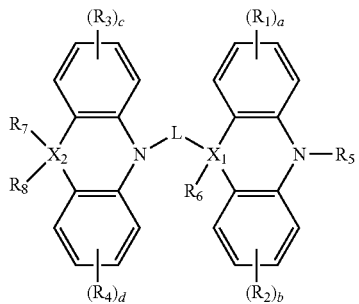

[Formula 1]

In Formula 1, $X_1$ and $X_2$ may be each independently any one of C, Si, Ge, or Sn. In the polycyclic compound represented by Formula 1, $X_1$ and $X_2$ may be the same or different from each other. As an example, when $X_1$ and $X_2$ are the same, both of $X_1$ and $X_2$ may be C.

In Formula 1, at least one of $X_1$ or $X_2$ may be Si. For example, any one of $X_1$ or $X_2$ may be Si. In some implementations, both of $X_1$ and $X_2$ may be Si. In some implementations, one of $X_1$ or $X_2$ may be Si, the other one of $X_1$ and $X_2$ may be C. Furthermore, in Formula 1, any one of $X_1$ or $X_2$ may be one of Si, Ge or Sn, and the other one of $X_1$ and $X_2$ may be C.

In the polycyclic compound represented by Formula 1, L may be a substituted or unsubstituted arylene group having 6 to 30 ring carbon atoms, or a substituted or unsubstituted heteroarylene group having 2 to 30 ring carbon atoms. In Formula 1, for example, L may be a linker connecting two acridine derivatives together. The linker L may connect the nitrogen atom of any one of two acridine derivatives with the other acridine derivative. For example, in Formula 1, L may be a linker connecting the nitrogen atom of any one of two acridine derivatives with $X_1$ of the other.

In Formula 1, L may be a substituted or unsubstituted phenylene group, or a substituted or unsubstituted divalent biphenyl group. For example, L may be an unsubstituted phenylene group, or an unsubstituted divalent biphenyl group.

L may be an arylene group represented by any one of the following L-1 to L-4.

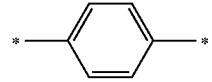

L-1

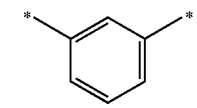

L-2

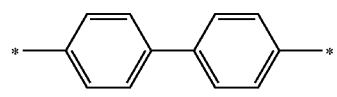

L-3

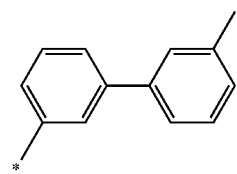

L-4

Even though no substituent is shown in the phenylene or divalent biphenyl groups represented by L1 to L4, it is to be understood that the phenylene or divalent biphenyl group represented by any one of L1 to L4 may be unsubstituted or substituted with at least one of a deuterium atom, a halogen atom, a nitro group, an amino group, a silyl group, boron, phosphine oxide, phosphine sulfide, an alkyl group, an alkenyl group, an aryl group, and heterocycle group.

Referring to L-1 and L-2, for example, two acridine derivatives in the polycyclic compound represented by Formula 1 may be substituted at para- or meta-position of the phenylene group.

In some implementations, in Formula 1, L may be a substituted or unsubstituted heteroarylene group including any one of N, O, or S as a hetero atom. For example, L may be a heteroarylene group represented by any one of the following L-5 to L-7:

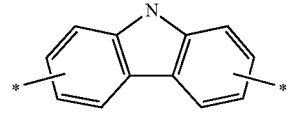

L-5

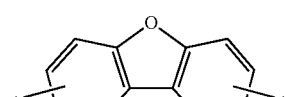

L-6

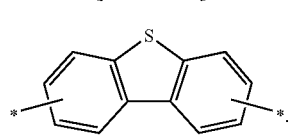

L-7

In the polycyclic compound of Formula 1, $R_1$ to $R_4$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. In addition, "a" to "d" may each independently be an integer of 1 to 4.

When "a" to "d" are an integer of 2 or more, a plurality of $R_1$ to $R_4$ may be the same or different from each other. For example, when "a" is an integer of 2 or more, a plurality of $R_1$ may be the same or different from each other. When "a" is an integer of 3 or more, all $R_1$ may be different from each other, or at least two $R_1$ may be the same. When "b" to "d" are an integer of 2 or more, the same explanation with respect to $R_1$ may be applied to $R_2$ to $R_4$.

Furthermore, when "a" to "d" are an integer of 2 or more, a plurality of $R_1$ to $R_4$ do not form a ring by combining with adjacent substituents. For example, when "a" is an integer of 2 or more, adjacent $R_1$'s of a plurality of $R_1$ do not combine with each other to form a ring. In addition, the substituents of adjacent $R_1$'s of a plurality of $R_1$ do not combine with each other to form a ring.

In Formula 1, $R_5$ may be a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. For example, $R_5$ may be a substituted or unsubstituted alkyl group having 1 to 20 carbon atoms, or a substituted or unsubstituted aryl group having 6 to 30 ring carbon atoms. For example, $R_5$ may be a methyl group or a substituted or unsubstituted phenyl group. In an embodiment, $R_5$ may be an unsubstituted phenyl group.

In the polycyclic compound represented by Formula 1, $R_6$ to $R_8$ are each independently a substituted or unsubstituted alkyl group having 1 to 20 carbon atoms, a substituted or unsubstituted alkoxy group having 1 to 20 carbon atoms, a substituted or unsubstituted aryloxy group having 6 to 30 ring carbon atoms, a substituted or unsubstituted aryl group having 6 to 30 ring carbon atoms, or a substituted or unsubstituted heteroaryl group having 2 to 30 ring carbon atoms, or may form a ring by combining adjacent groups with each other.

In Formula 1, $R_6$ may be a substituted or unsubstituted alkyl group having 1 to 20 carbon atoms, or a substituted or unsubstituted aryl group having 6 to 30 ring carbon atoms. For example, $R_6$ may be a methyl group or a substituted or unsubstituted phenyl group. In an embodiment, $R_6$ may be an unsubstituted phenyl group.

In Formula 1, $R_6$ may be a substituted or unsubstituted heteroaryl group having 2 to 30 ring carbon atoms. When $R_6$ is a substituted or unsubstituted heteroaryl group having 2 to 30 ring carbon atoms. However, a case where $R_6$ and L combine with each other to form a ring may be excluded. For example, a substituted or unsubstituted heteroaryl group $R_6$ does not combine with L, which is a substituted or unsubstituted arylene or a substituted or unsubstituted heteroarylene, to form a ring. For example, adjacent substituents of $R_6$ and L do not combine with each other to form a ring.

In the polycyclic compound represented by Formula 1, $R_7$ and $R_8$ are each independently a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, or may form a ring by combining adjacent groups with each other. For example, $R_7$ and $R_8$ may each independently be a methyl group or a substituted or unsubstituted phenyl group. In some implementations, $R_7$ and $R_8$ may combine with each other to form a substituted or unsubstituted fluorene ring.

The polycyclic compound represented by Formula 1 according to an embodiment may be, for example, any one of compounds represented in the following Compound Group 1.

[Compound Group 1]

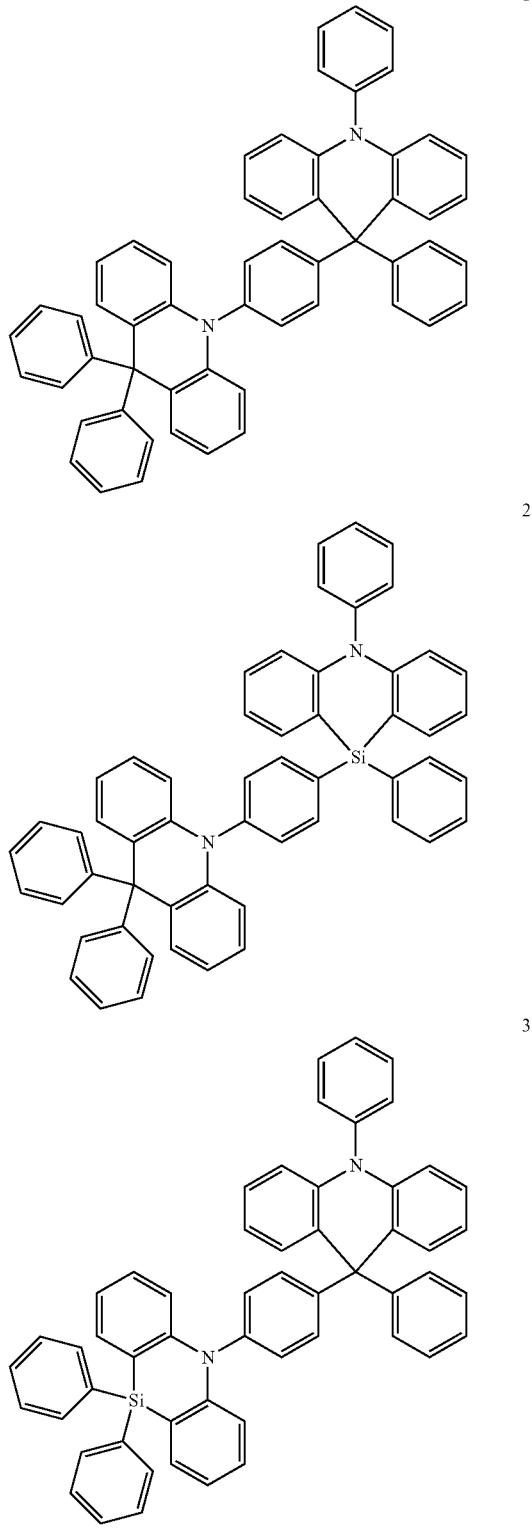

23
-continued
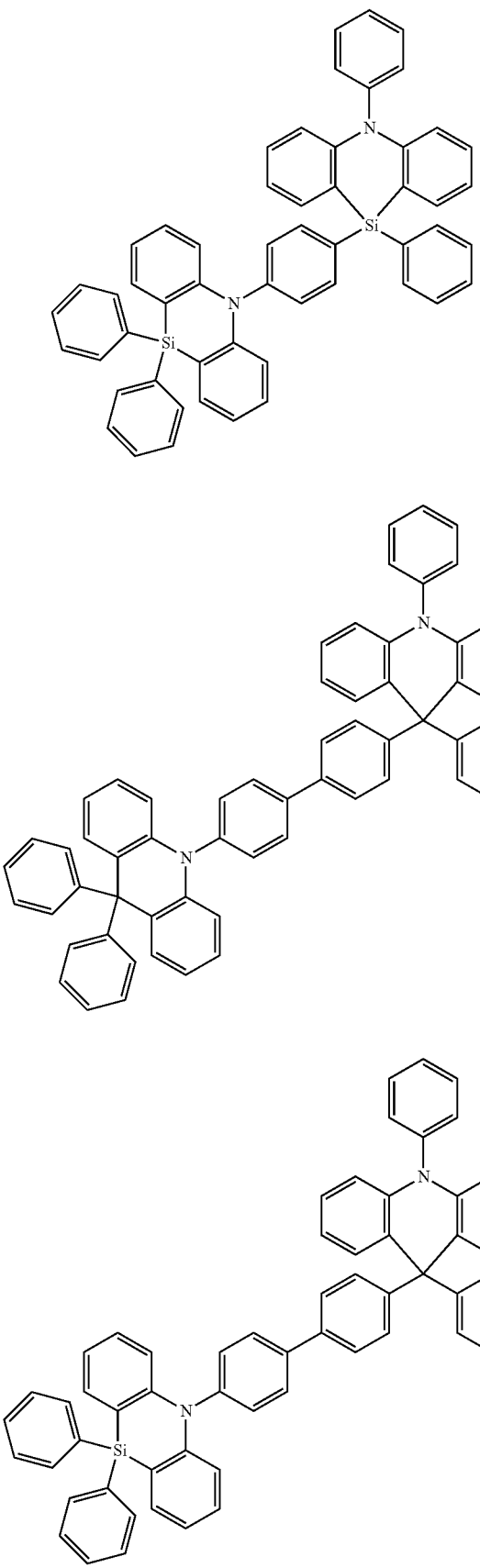
24
-continued
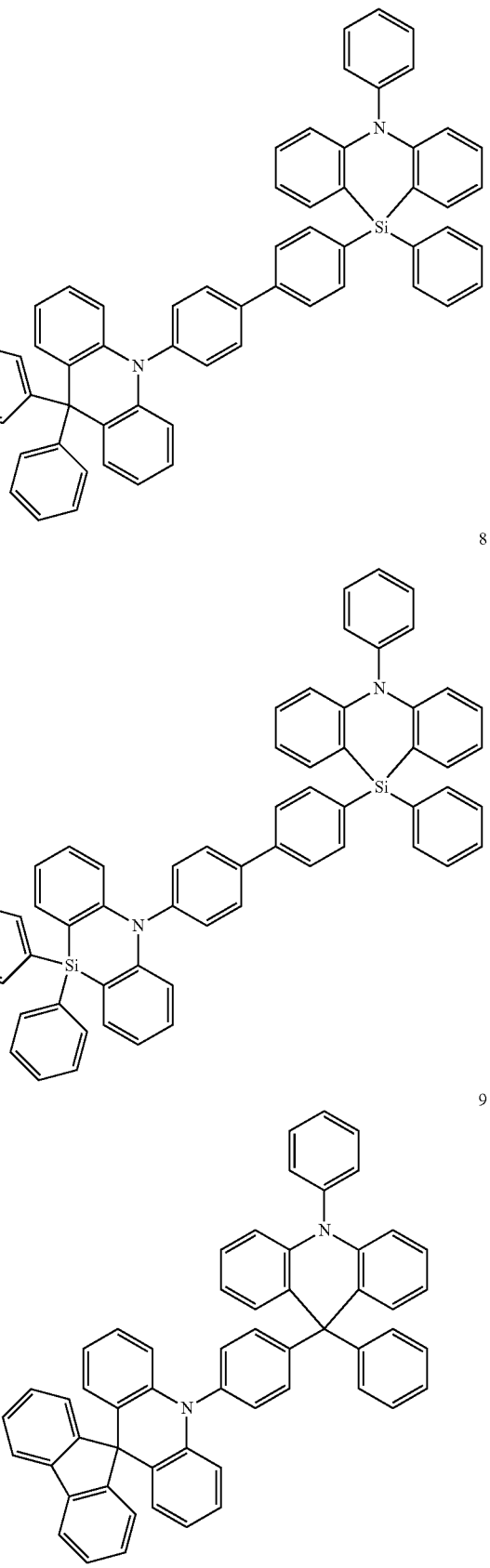

10
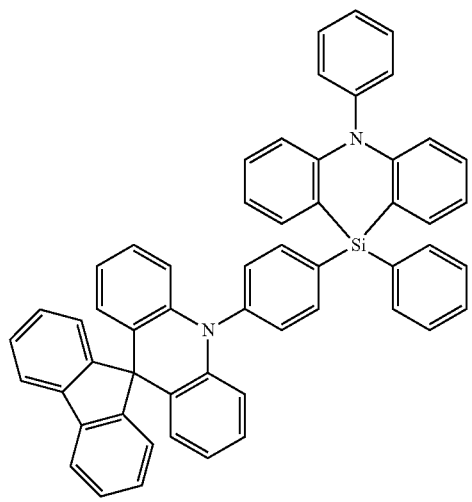
11
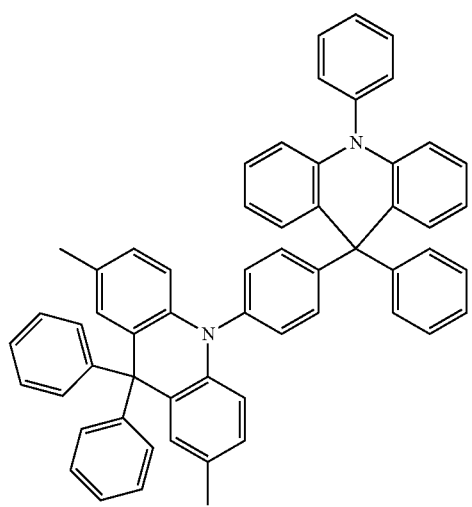
12
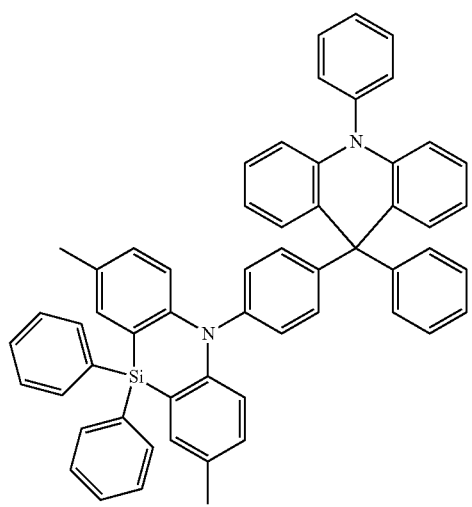
13
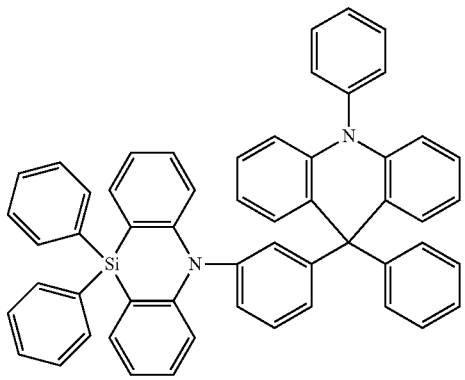
14
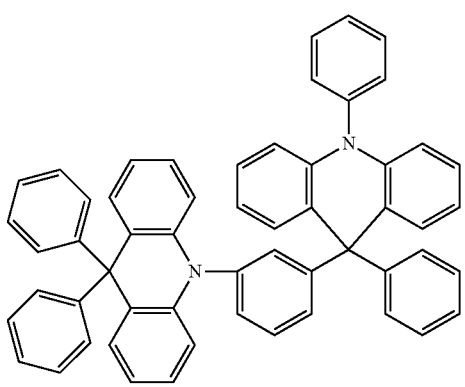
15
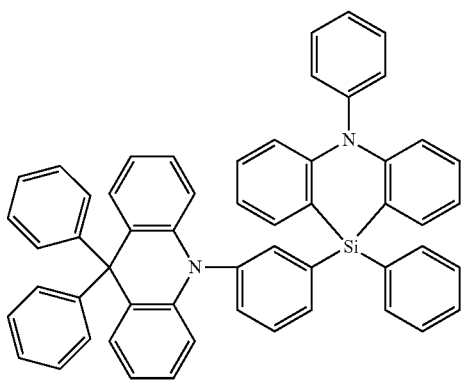
16
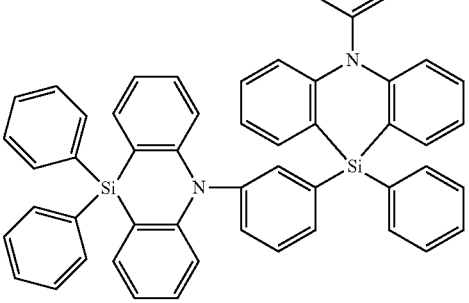

17
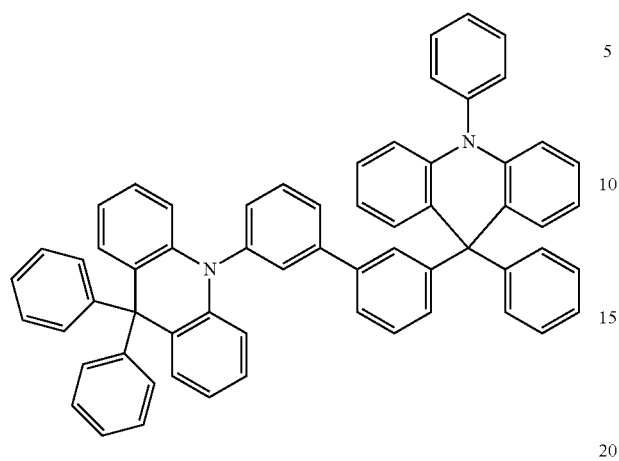
18
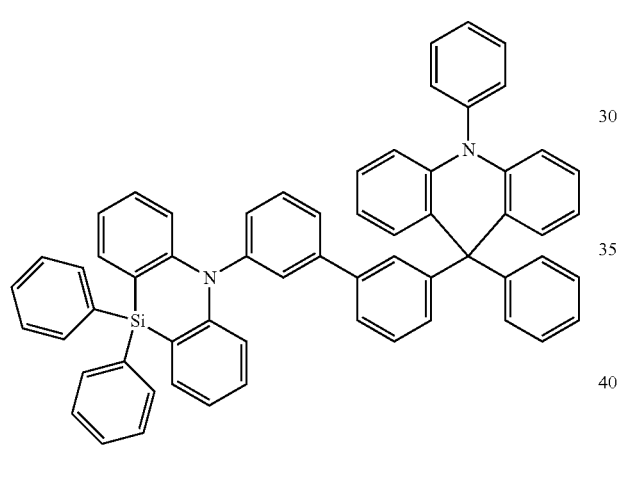
19
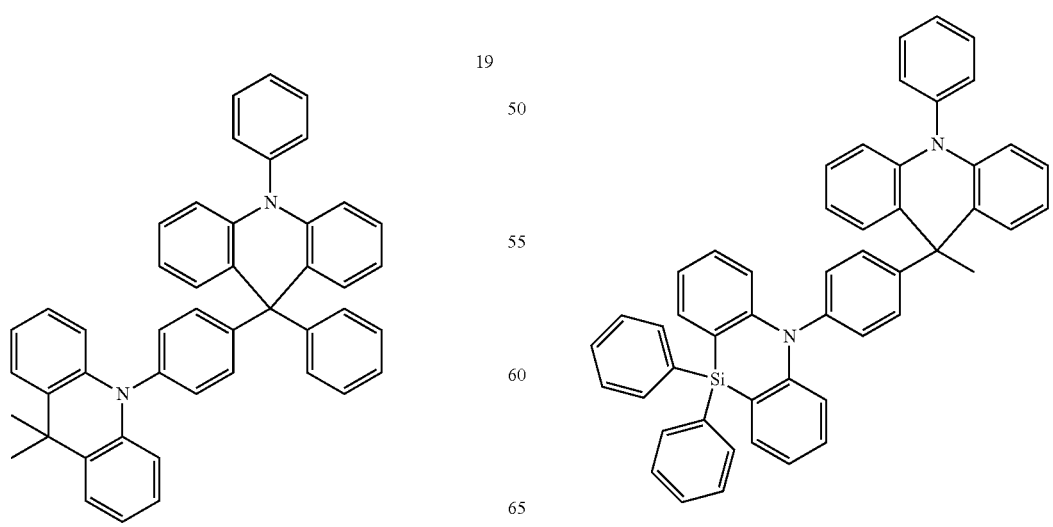
20
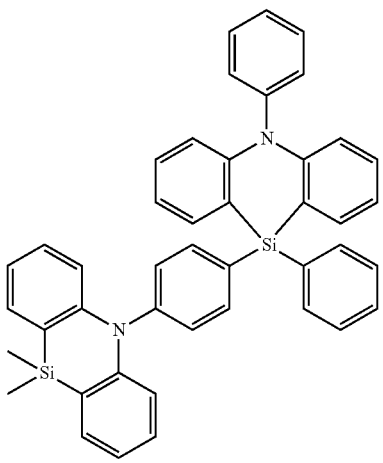
21
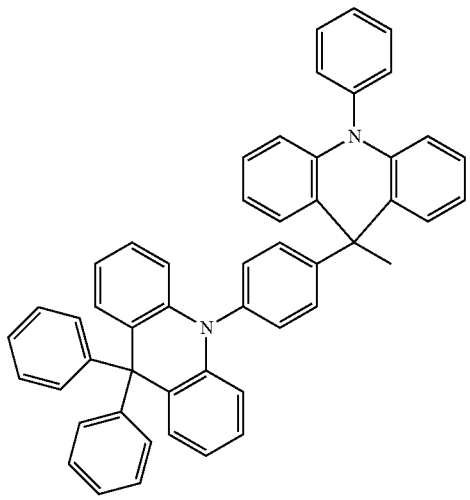
22

23
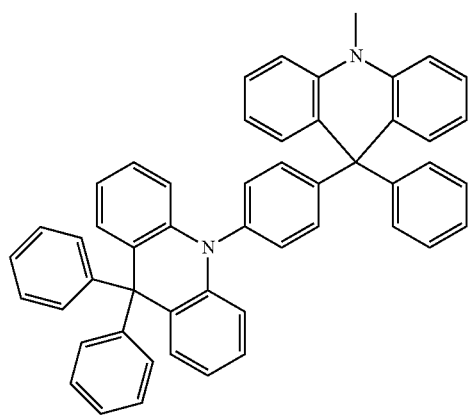
24
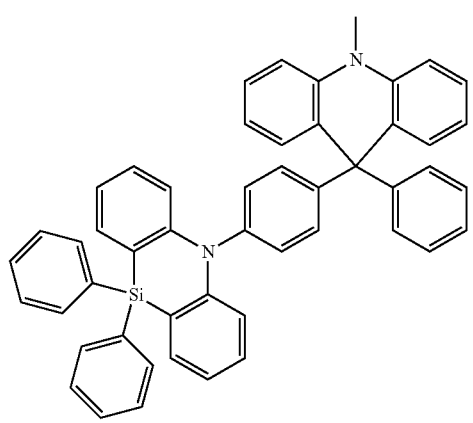
25
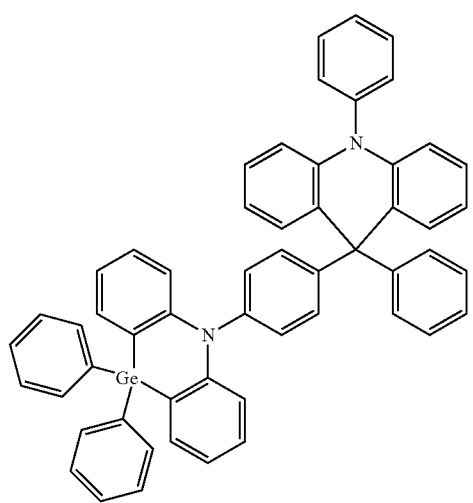
26
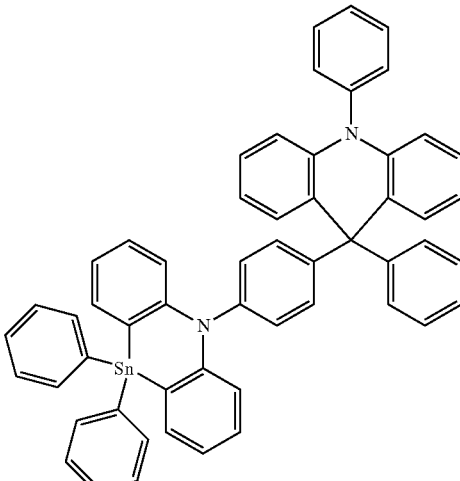
27
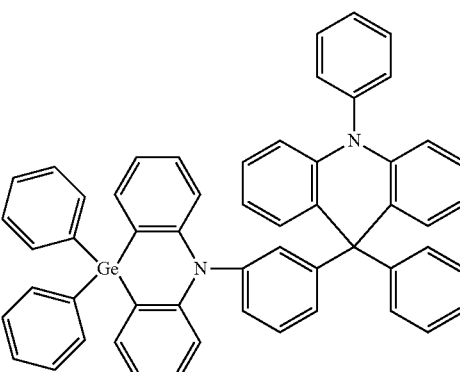
28
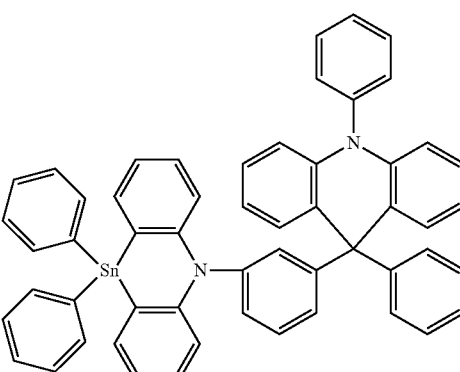
29
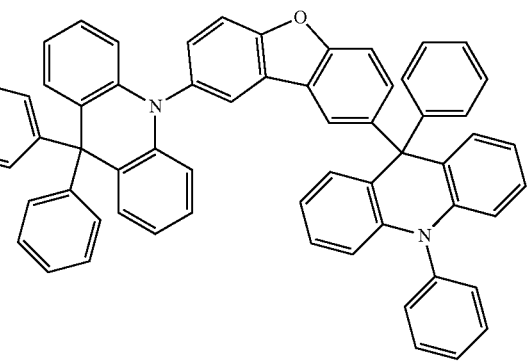

30
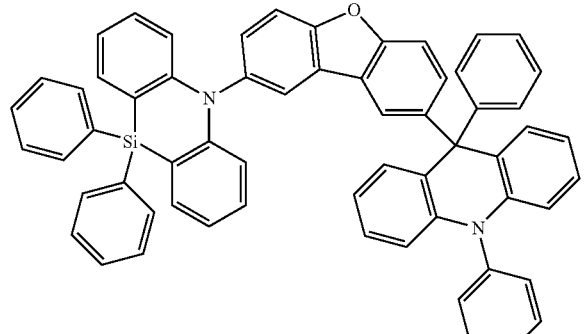
31
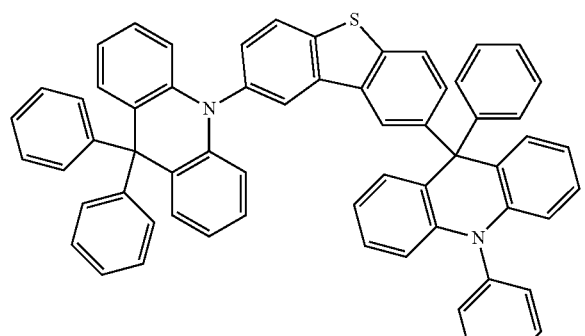
32
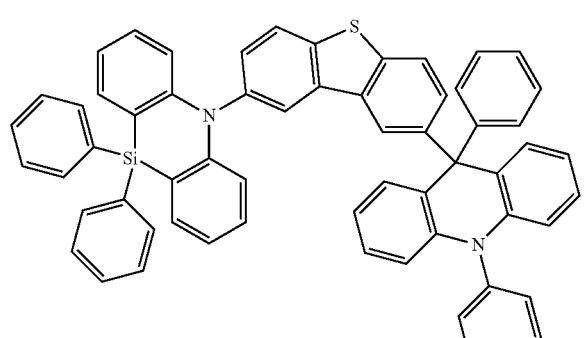
33
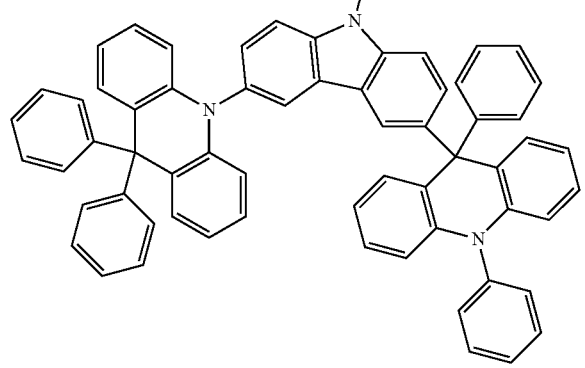
34
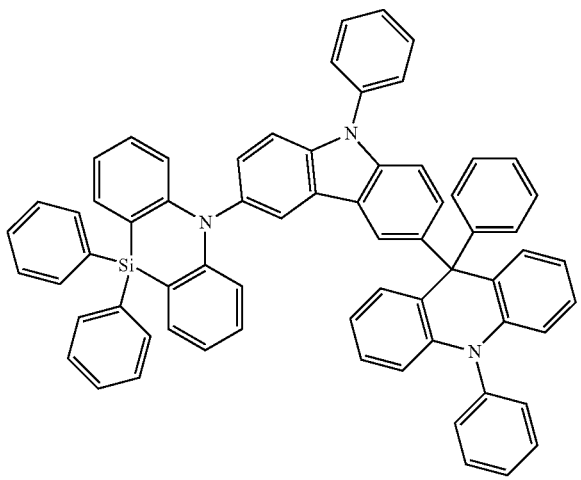
35
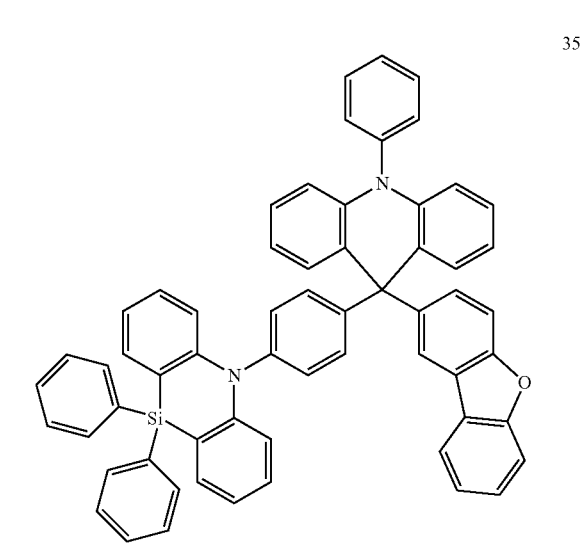
36
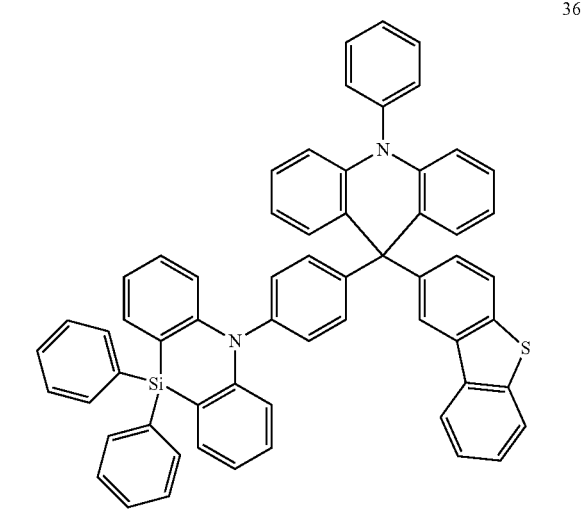

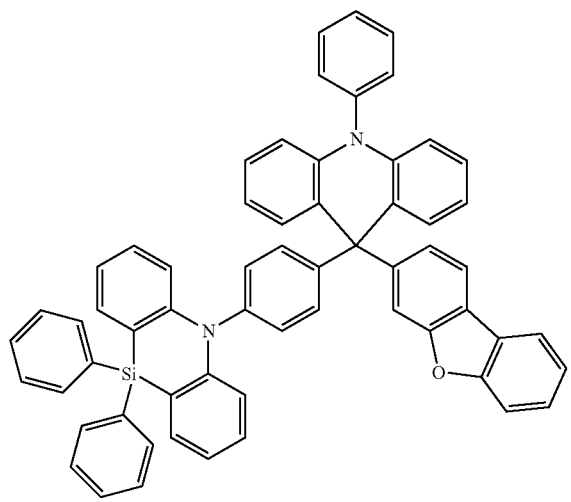

37

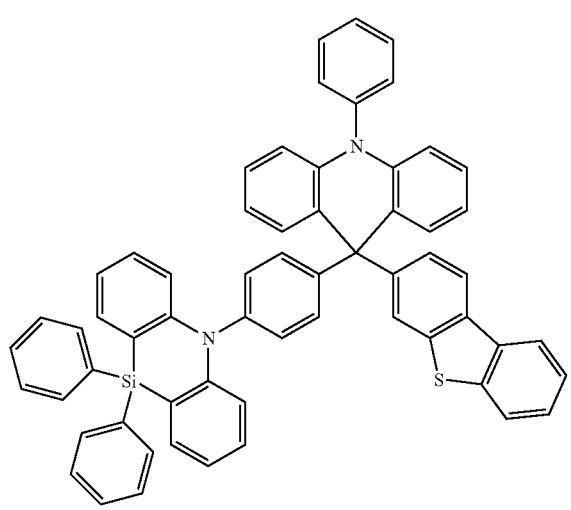

38

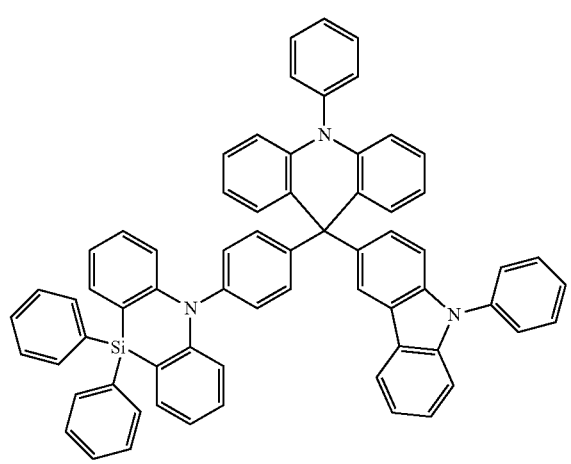

39

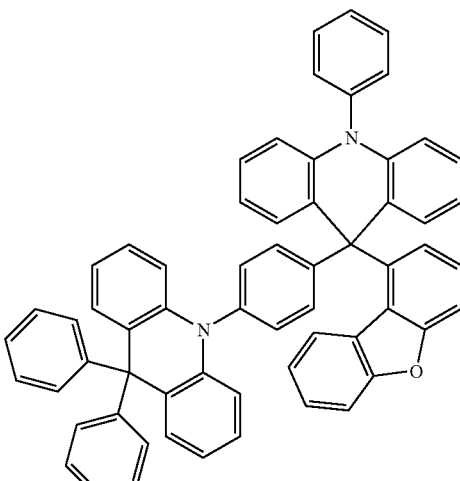

40

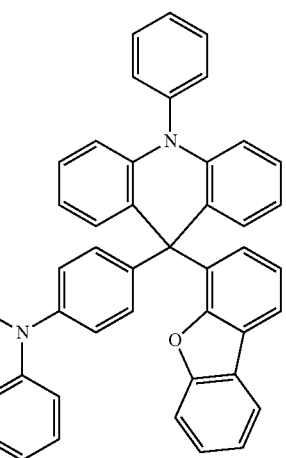

41

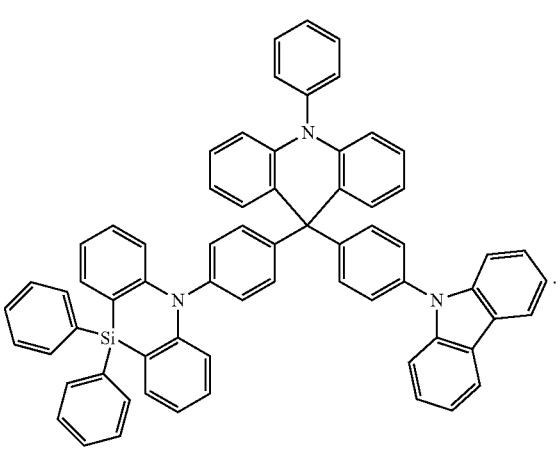

42

The polycyclic compound according to an embodiment may be used as a material for an organic electroluminescence device to improve the emission efficiency of the organic electroluminescence device. The polycyclic compound according to an embodiment may have a high level of the lowest triplet excitation energy (T1). When the polycyclic compound according to an embodiment has a high level of the lowest triplet excitation energy, diffusion of triplet excitons generated in an emission layer into a hole transport region may be inhibited. Thereby, emission efficiency of an organic electroluminescence device may be improved.

Hereinafter, an organic electroluminescence device according to an embodiment will be explained. Specific explanations regarding the above-described polycyclic compound will not be repeated.

Figure 2:
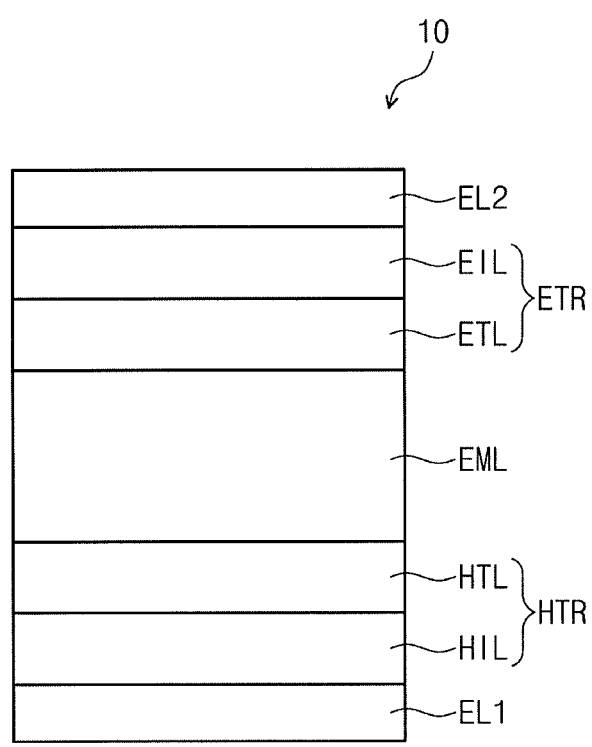
FIG. 2 illustrates a schematic cross-sectional view of an organic electroluminescence device according to an embodiment.
Figure 3:
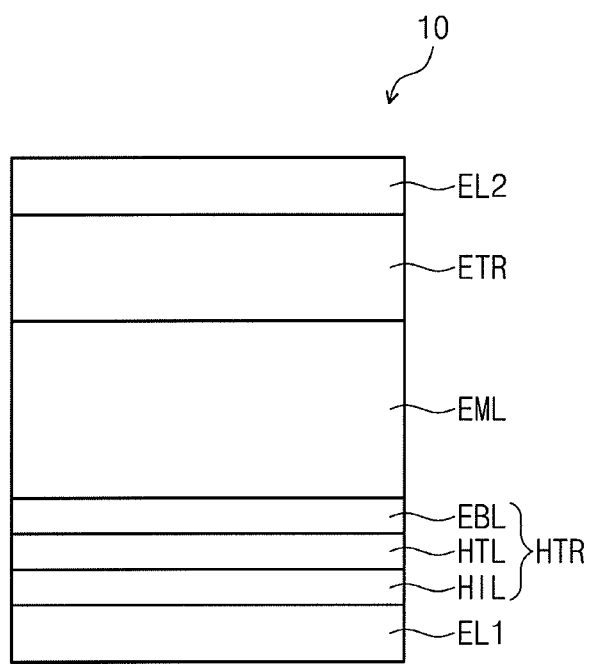
FIG. 3 illustrates a schematic cross-sectional view of an organic electroluminescence device according to an embodiment.

Each of FIGS. 1 to 3 illustrates a schematic cross-sectional view depicting an organic electroluminescence device according to an embodiment. Referring to FIGS. 1 to 3, an organic electroluminescence device 10 according to an embodiment may include a first electrode EL1, a hole transport region HTR, an emission layer EML, an electron transport region ETR, and a second electrode EL2, laminated in order. In the embodiment depicted in FIG. 2, a hole transport region HTR includes a hole injection layer HIL and a hole transport layer HTL, and an electron transport layer ETR includes an electron injection layer EIL and an electron transport layer ETL. In the embodiment depicted in FIG. 3, the hole transport region HTR of the organic electroluminescence device includes a hole injection layer HIL, a hole transport layer HTL and an electron blocking layer EBL.

The first electrode EL1 and the second electrode EL2 may be disposed oppositely, and a plurality of organic layers may be disposed between the first electrode EL1 and the second electrode EL2. The plurality of organic layers may include a hole transport region HTR, an emission layer EML and an electron transport region ETR.

The organic electroluminescence device 10 according to an embodiment may include the polycyclic compound according to an embodiment in a hole transport region HTR.

The first electrode EL1 has conductivity. The first electrode EL1 may be formed to include a metal alloy or a conductive compound. The first electrode EL1 may be an anode.

The first electrode EL1 may be a transmissive electrode, a transflective electrode, or a reflective electrode. When the first electrode EL1 is the transmissive electrode, the first electrode EL1 may be made of a transparent metal oxide such as indium tin oxide (ITO), indium zinc oxide (IZO), zinc oxide (ZnO), or indium tin zinc oxide (ITZO). When the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO.

Hereinafter, a case where the polycyclic compound according to an embodiment is included in a hole transport region HTR, will be explained. The polycyclic compound according to an embodiment may be included in at least one layer of one or more organic layers disposed between the first electrode EL1 and the second electrode EL2. For example, the polycyclic compound according to an embodiment may be included in an emission layer EML.

The organic electroluminescence device 10 according to an embodiment may include the polycyclic compound represented by Formula 1 in a hole transport region HTR.

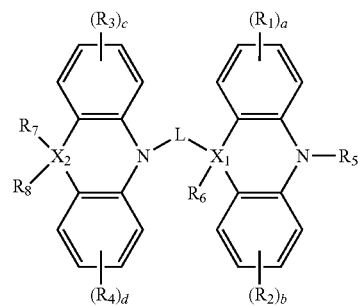

[Formula 1]

In Formula 1, $X_1$ and $X_2$ are each independently any one of C, Si, Ge, or Sn, and L may be a substituted or unsubstituted arylene group having 6 to 30 ring carbon atoms, or a substituted or unsubstituted heteroarylene group having 2 to 30 ring carbon atoms. $R_1$ to $R_4$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 1, $R_5$ may be a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 1, $R_6$ to $R_8$ are each independently a substituted or unsubstituted alkyl group having 1 to 20 carbon atoms, a substituted or unsubstituted alkoxy group having 1 to 20 carbon atoms, a substituted or unsubstituted aryloxy group having 6 to 30 ring carbon atoms, a substituted or unsubstituted aryl group having 6 to 30 ring carbon atoms, or a substituted or unsubstituted heteroaryl group having 2 to 30 ring carbon atoms, or form a ring by combining adjacent groups with each other, and "a" to "d" may be each independently an integer of 1 to 4.

In Formula 1, particular explanation on the polycyclic compound according to an embodiment as described above may be applied to $X_1$, $X_2$, L and $R_1$ to $R_8$.

The polycyclic compound represented by Formula 1 may have a high level of the lowest triplet excitation energy (T1). For example, the polycyclic compound represented by Formula 1 may have the lowest triplet excitation energy of about 3.2 eV or higher.

The hole transport region HTR may be disposed on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1.

The hole transport region HTR may be formed using a suitable such as a vacuum deposition method, a spin coating method, a cast method, a Langmuir-Blodgett (LB) method, an inkjet printing method, a laser printing method, or a laser induced thermal imaging (LITI) method.

The hole transport region HTR may include the above-described polycyclic compound according to an embodiment. The hole transport region HTR may include the above-described polycyclic compound according to an embodiment as a hole transport material.

The layer including the polycyclic compound according to an embodiment may be a layer adjacent to the emission layer EML. As shown in FIG. 2, when the hole transport layer HTL in the hole transport region HTR is adjacent to the emission layer EML, the hole transport layer HTL may include the polycyclic compound according to an embodiment. In some implementations, as shown in FIG. 3, when an electron blocking layer EBL is further included on the hole transport layer HTL in the hole transport region HTR, the electron blocking layer EBL may include the polycyclic compound according to an embodiment.

At least one of the hole transport layer HTL or the electron blocking layer EBL may include one or more of the polycyclic compound represented by Formula 1. The hole transport layer HTL and the electron blocking layer EBL may further include another suitable material in addition to the polycyclic compound represented by Formula 1.

When the hole transport layer HTL or the electron blocking layer EBL includes the polycyclic compound according to an embodiment, the hole injection layer HIL may include a suitable hole injection material. The hole injection material included in the hole injection layer HIL may include, for example, triphenylamine-containing polyether ketone (TPA-PEK), 4-isopropyl-4'-methyldiphenyliodiumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris(N,N-diphenylamino)triphenylamine (TDATA). 4,4',4''-tris {N,N'-2-naphthylphenylamino}-triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), etc.

When the hole transport layer HTL does not includes the polycyclic compound according to an embodiment, and the electron blocking layer EBL includes the polycyclic compound according to an embodiment, the hole transport layer HTL may include, for example, 1,1-bis[(di-4-tolylamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), N,N'-di(1-naphthyl)-N,N'-diphenylbenzidine (NPB), etc. The thickness of the hole transport region HTR may be from about 100 Å to about 10,000 Å, or, for example, from about 100 Å to about 1,000 Å. When the hole transport region HTR includes both of the hole injection layer HIL and the hole transport layer HTL, the thickness of the hole injection layer HIL may be from about 100 Å to about 10,000 Å, or, for example, from about 100 Å to about 1,000 Å, and the thickness of the hole transport layer HTL may be from about 30 Å to about 1,000 Å. When the thicknesses of the hole transport region HTR, the hole injection layer HIL and the hole transport layer HTL satisfy the above-described ranges, satisfactory hole transport properties may be obtained without a substantial increase of a driving voltage.

The hole transport region HTR may further include a charge generating material, in addition to the above-described materials, to improve conductivity. The charge generating material may be dispersed in the hole transport region HTR uniformly or non-uniformly. The charge generating material may be, for example, a p-dopant. The p-dopant may be one of a quinone derivative, a metal oxide, or a cyano group-containing compound, as examples. Examples of the p-dopant may include a quinone derivative such as tetracyanoquinodimethane (TCNQ) and 2,3,5,6-tetrafluoro-tetracyanoquinodimethane (F4-TCNQ), or a metal oxide such as tungsten oxide or molybdenum oxide.

The hole transport region HTR may further include at least one of the hole buffer layer and the electron blocking layer EBL in addition to the hole injection layer HIL and the hole transport layer HTL, as described above. The hole buffer layer may compensate an optical resonance distance according to the wavelength of light emitted from the emission layer EML and may increase light emission efficiency. Materials included in the hole transport region HTR may be used as materials included in the hole buffer layer. The electron blocking layer EBL is a layer preventing electron injection from the electron transport region ETR into the hole transport region HTR.

For example, in an embodiment, the hole transport region HTR may include the hole injection layer HIL, the hole transport layer HTL and the electron blocking layer EBL. In an embodiment, the polycyclic compound represented by Formula 1 may be included in at least one of the hole transport layer HTL and the electron blocking layer EBL. The polycyclic compound represented by Formula 1 may be included in any one of the hole transport layer HTL and the electron blocking layer EBL, or may be included in both of the hole transport layer HTL and the electron blocking layer EBL.

The hole transport region HTR of the organic electroluminescence device 10 according to an embodiment may include one or more of the polycyclic compound represented by Formula 1. For example, the organic electroluminescence device 10 according to an embodiment may include at least one of compounds represented in the following Compound Group 1 in the hole transport region HTR:

[Compound Group 1]
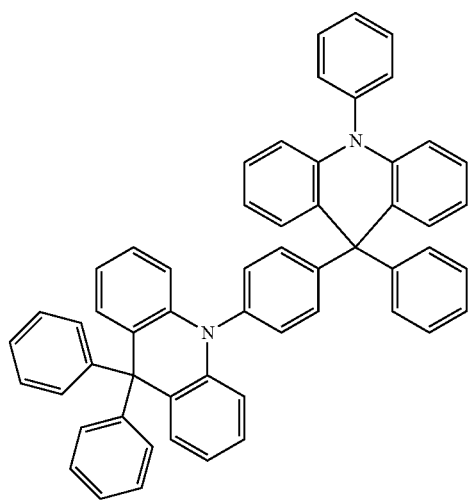
1
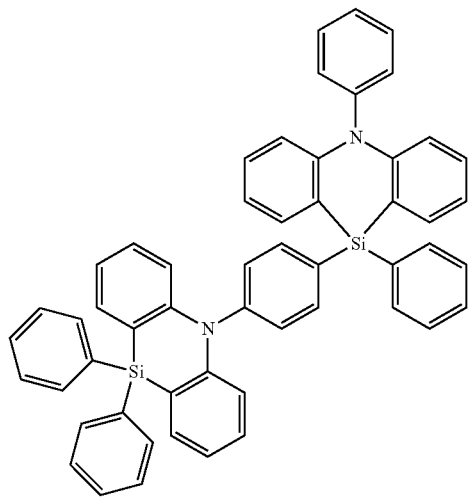
4
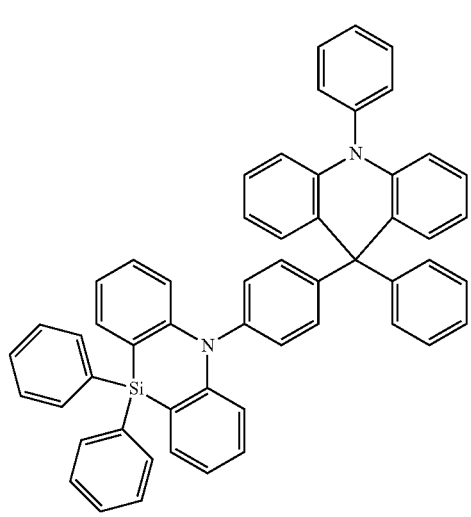
2
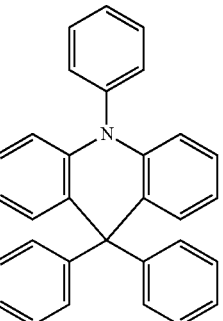
5
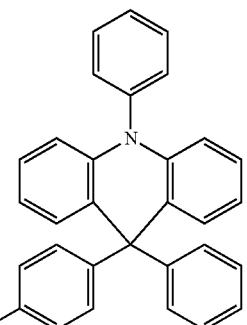
3
6

7
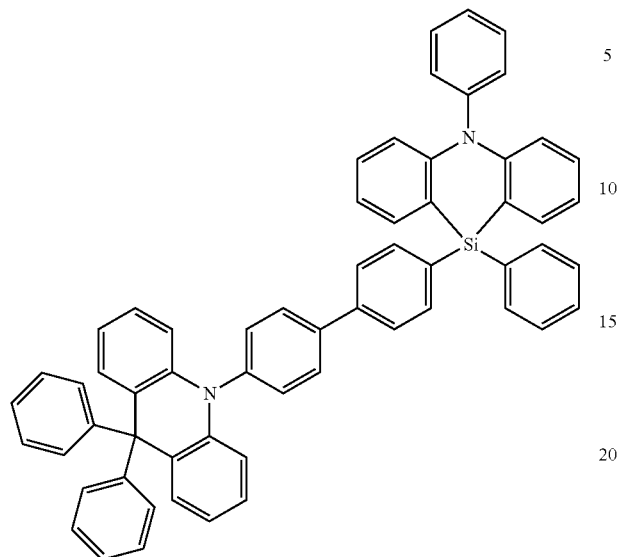
10
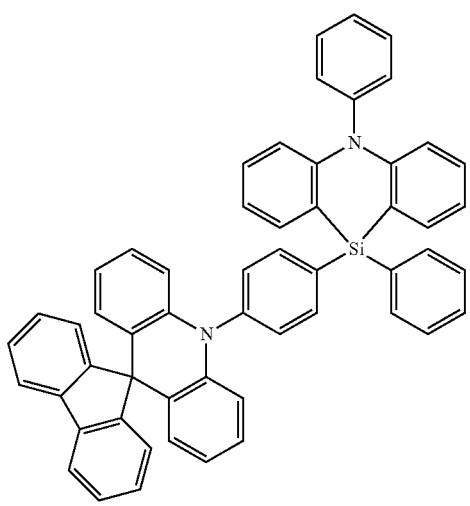
8
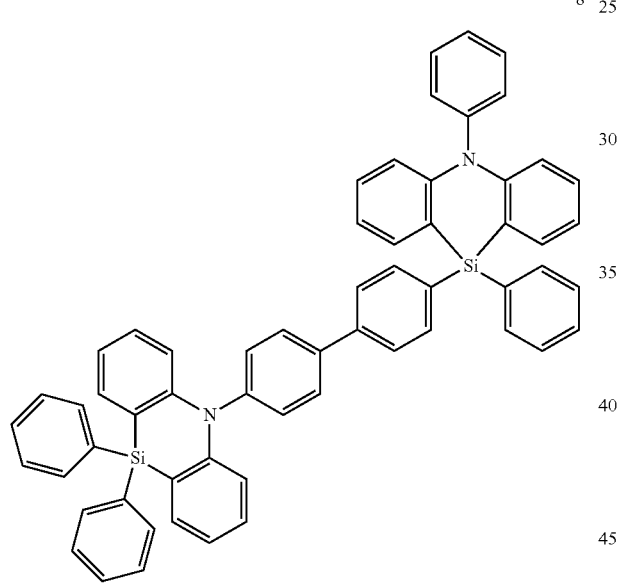
11
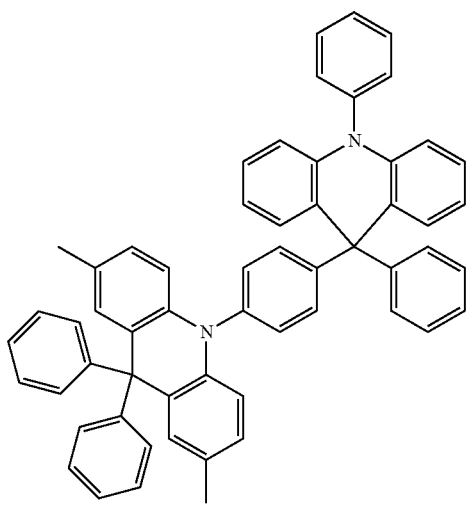
9
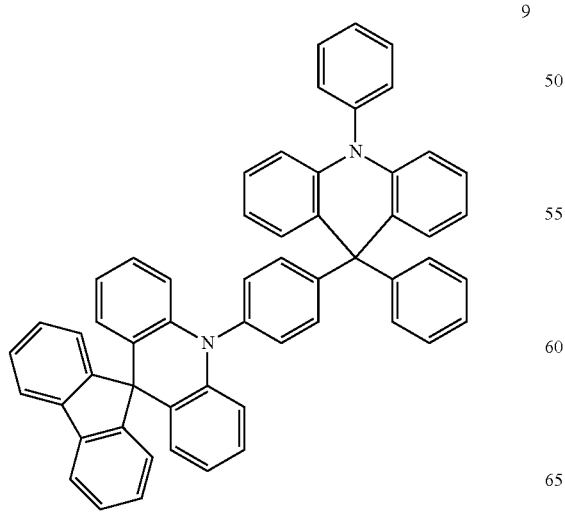
12
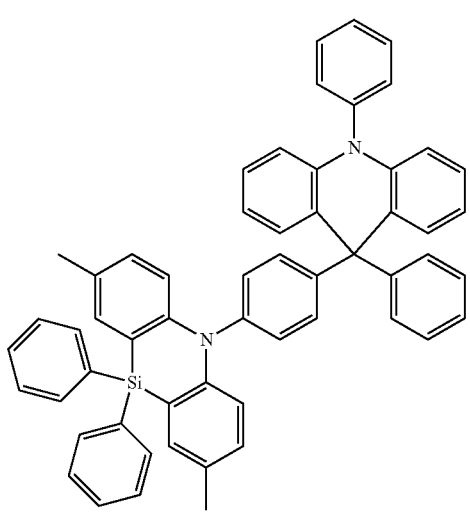

13
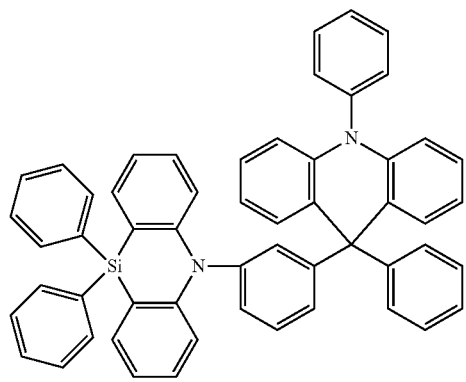
14
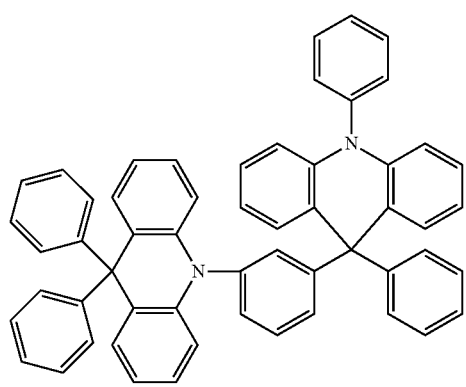
15
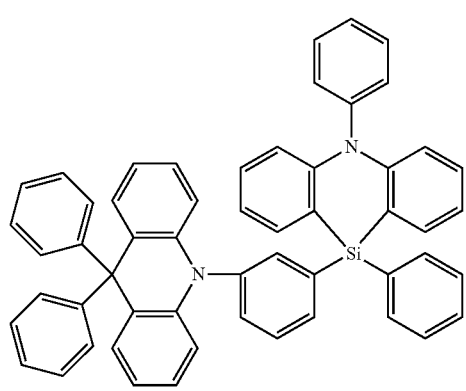
16
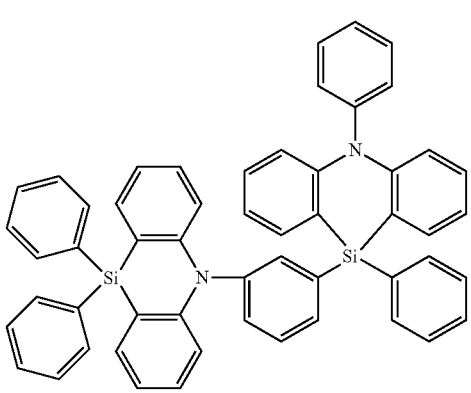
17
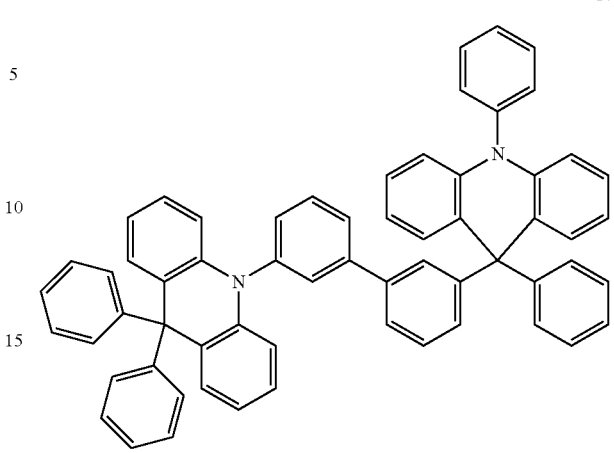
18
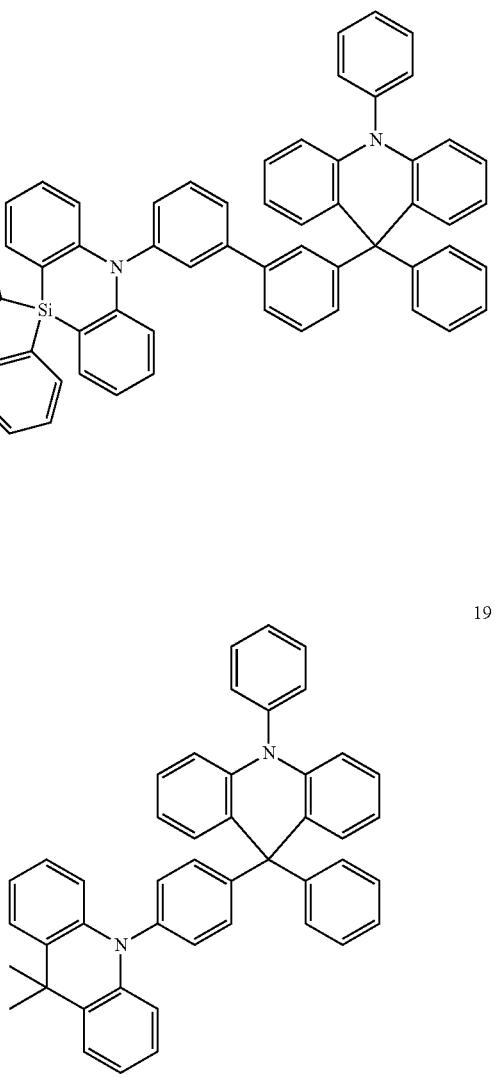
19

20
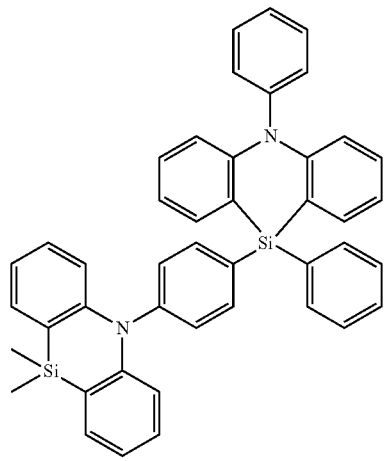
21
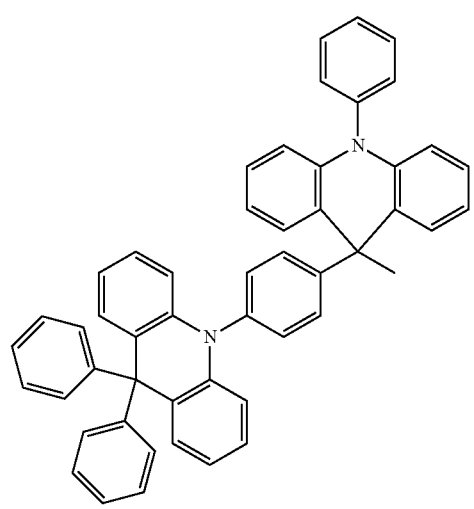
22
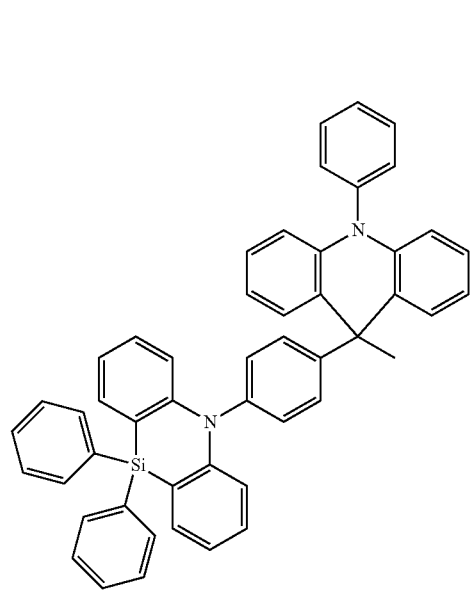
23
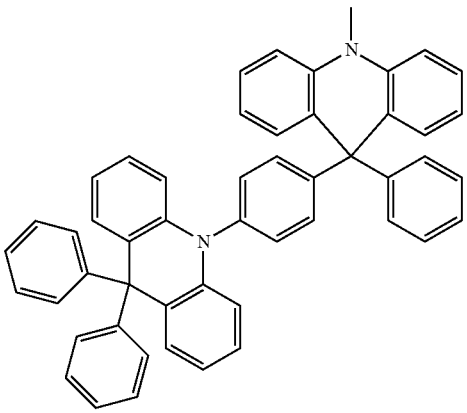
24
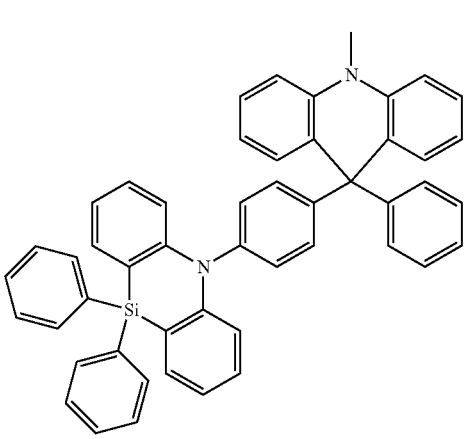
25
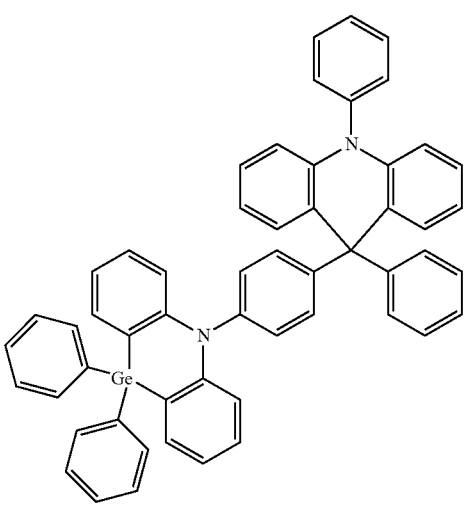

26
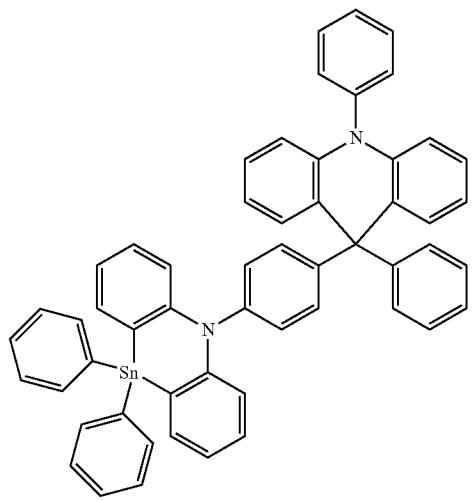
27
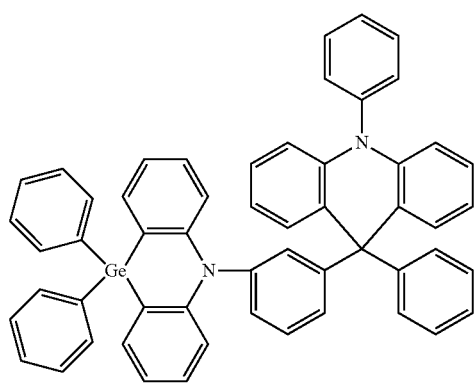
28
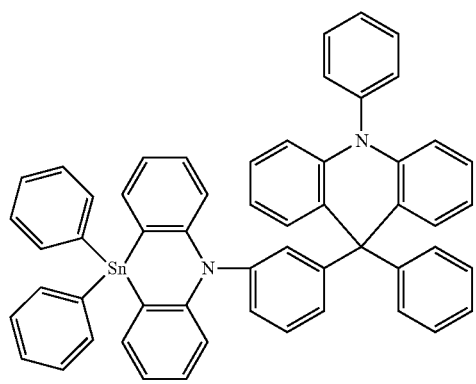
29
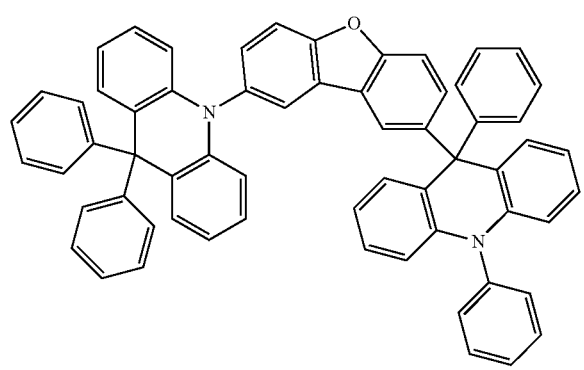
30
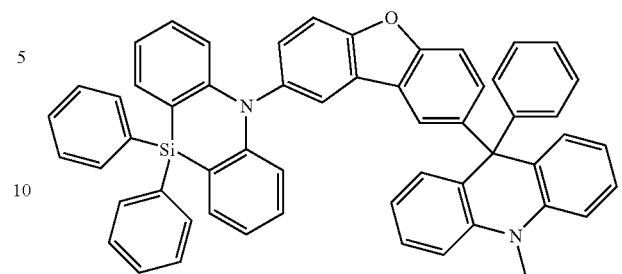
31
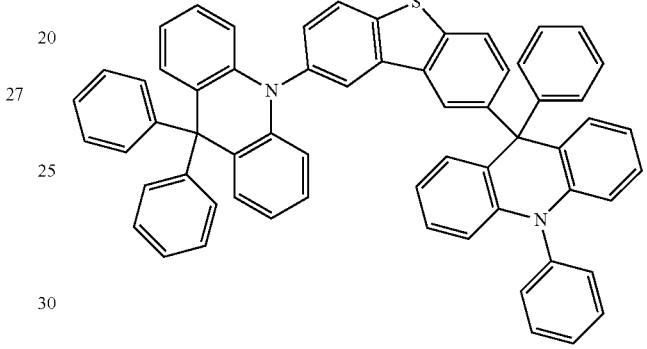
32
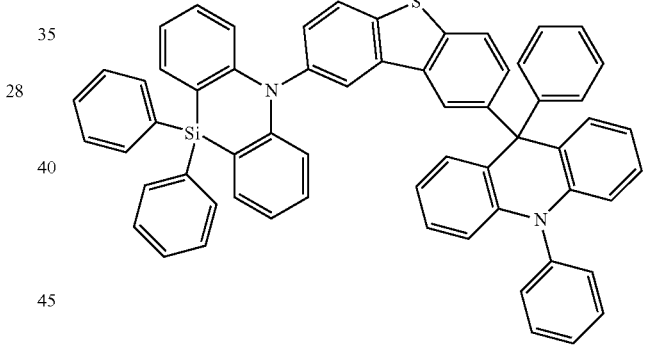
33
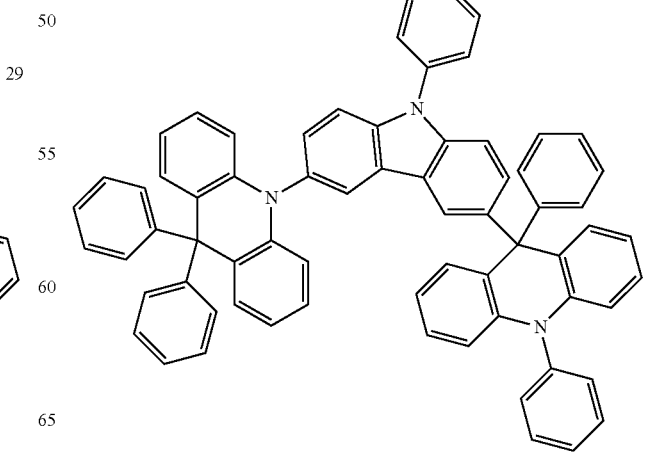

34
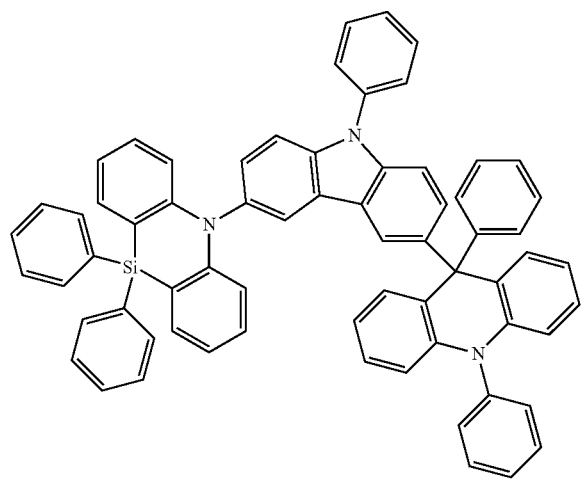
35
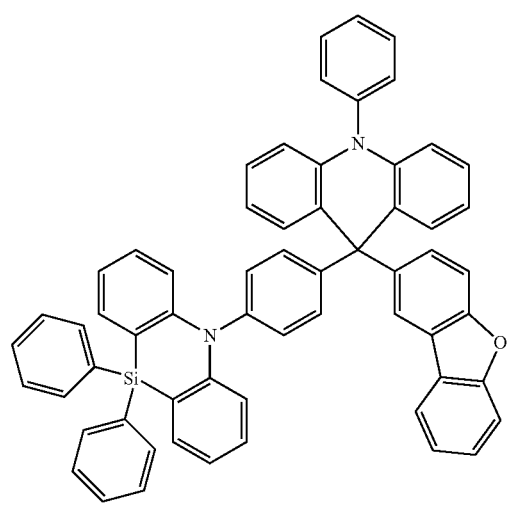
36
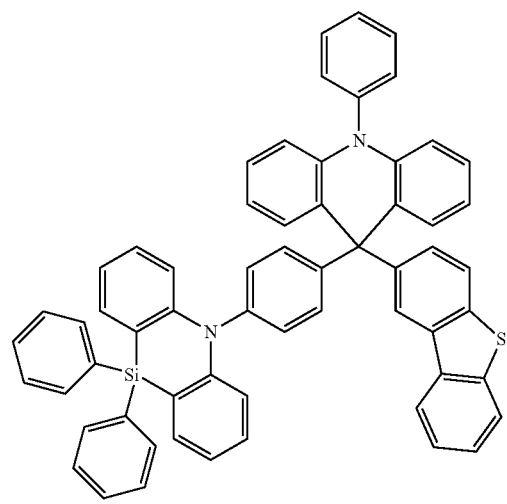
37
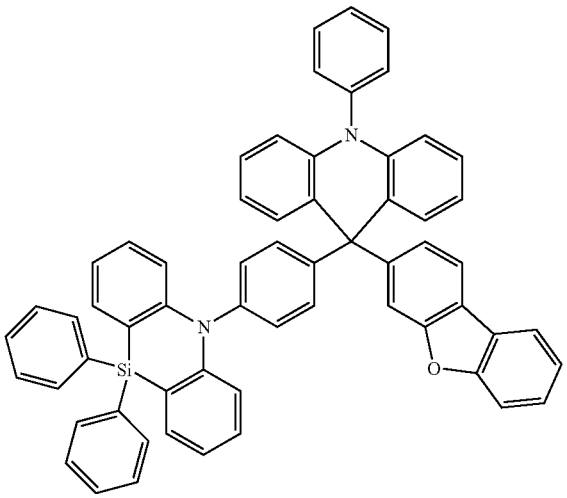
38
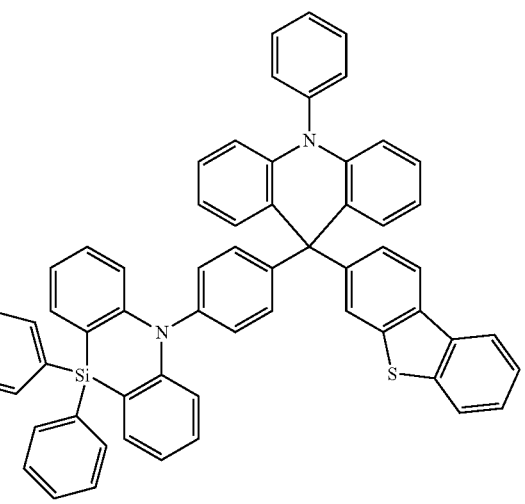
39
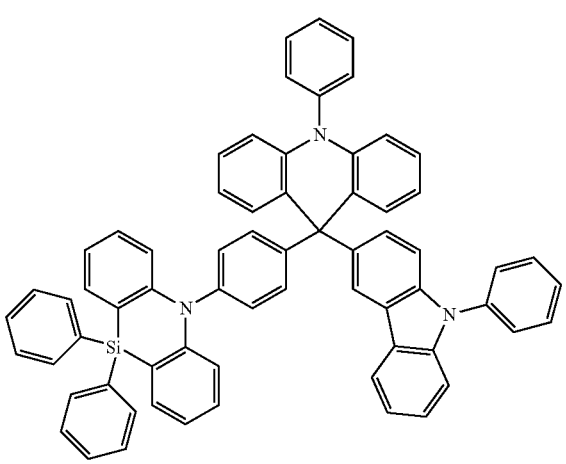

-continued

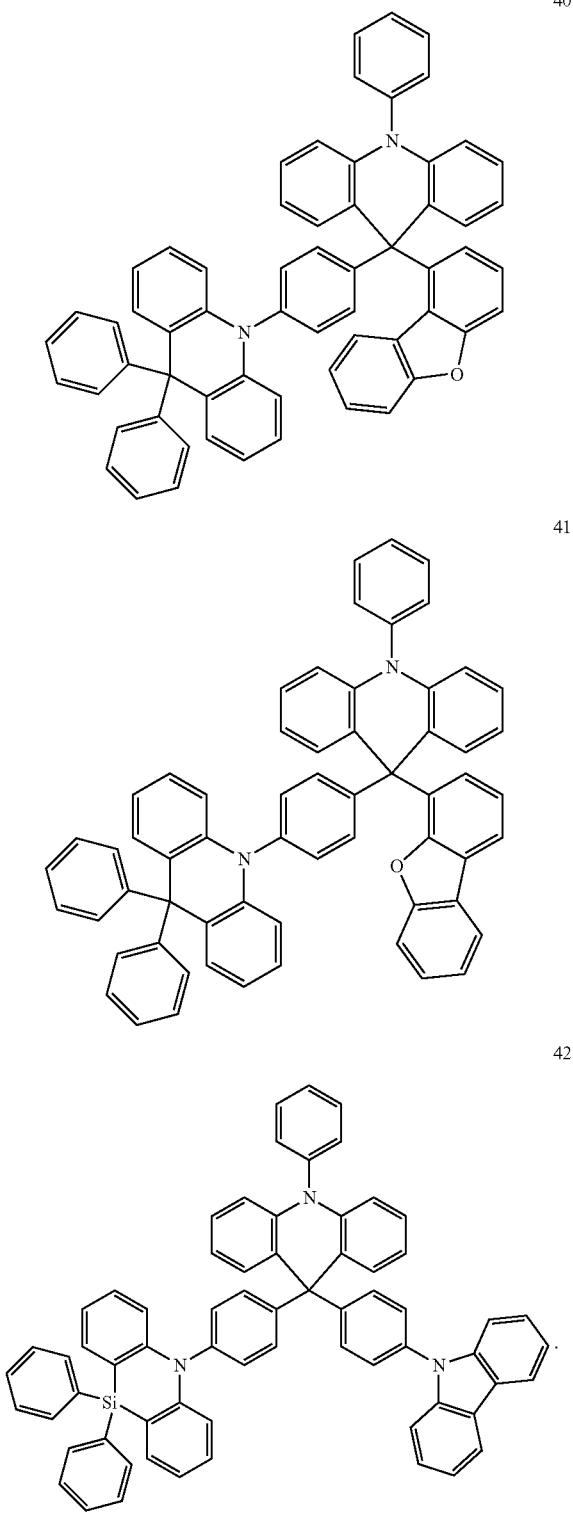

The organic electroluminescence device 10 according to an embodiment may have improved emission efficiency by including the polycyclic compounds represented by Formula 1 in the hole transport region HTR. Furthermore, the organic electroluminescence device 10 according to an embodiment may have improved external quantum efficiency by including the polycyclic compounds represented by Formula 1 according to an embodiment in the hole transport region HTR.

The emission layer EML may be disposed on the hole transport region HTR. The thickness of the emission layer EML may be, for example, from about 100 Å to about 600 Å. The emission layer EML may have a single layer formed using a single material, a single layer formed using a plurality of different materials, or a multilayer structure having a plurality of layers formed using a plurality of different materials.

The emission layer EMI, may emit one of red light, green light, blue light, white light, yellow light, or cyan light. For example, the emission layer EML of the organic electroluminescence device 10 according to an embodiment may emit blue light.

The emission layer EMI, may include a fluorescent material or a phosphorescent material. The emission layer EML may include a host and a dopant.

The emission layer EML may include a host. The host may be a suitable host material such as, for example, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4', 4"-tris(carbazol-9-yl)-triphenylamine (TCTA), 1,3,5-tris(N-phenylbenzimidazole-2-yl)benzene (TPBi), 3-tert-butyl-9, 10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO₃), octaphenylcyclotetrasiloxane (DPSiO₄), 2,8-bis(diphenylphosphoryl)dibenzofuran (PPF), etc.

The dopant may include, for example, a styryl derivative (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl) naphthalen-2-yl)vinyl)phenyl)-N-phenylbenzenamine (N-BDAVBi)), perylene and a derivative thereof (for example, 2,5,8,11-tetra-tert-butylperylene (TBP)), pyrene and a derivative thereof (for example, 1,1-dipyrene, 1,4-dipyrenylbenzene, 1,4-bis(N,N-diphenylamino)pyrene), etc.

When the emission layer EML is to emit red light, the emission layer EML may further include, for example, tris(dibenzoylmethanato)phenanthroline europium (PBD:Eu (DBM)₃(Phen)), or a fluorescent material including perylene. When the emission layer EML emits red light, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, and 4-dicyanomethylene-2-(p-dimethylaminostyryl)-6-methyl-4H-pyran (DCM) and the derivatives thereof.

When the emission layer EML is to emit green light, the emission layer EML may further include a fluorescent material including, for example, tris(8-hydroxyquinolino) aluminum (Alq3). When the emission layer EML is to emit green light, the dopant included in the emission layer EML may be selected from, for example, a metal complex or organometallic complex such as fac-tris(2-phenylpyridine) iridium (Ir(ppy)3), coumarin, and a derivative thereof.

When the emission layer EML is to emit blue light, the emission layer EML may further include a fluorescent material including any one of, for example, spiro-DPVBi, spiro-6P, distyryl-benzene (DSB), distyryl-arylene (DSA), a polyfluorene (PFO)-based polymer, and a poly(p-phenylene vinylene) (PPV)-based polymer. When the emission layer EML is to emit blue light, the dopant included in the emission layer EML may be selected from a metal complex or an organometallic complexes such as (4,6-F2ppy)2Irpic, perylene and a derivative thereof, etc.

The electron transport region ETR may be disposed on the emission layer EML. The electron transport region ETR may include at least one of a hole blocking layer, an electron transport layer ETL and an electron injection layer EIL.

The electron transport region ETR may be a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In addition, the electron transport region ETR may have a single layer structure having a plurality of different materials, or a laminated structure of electron transport layer ETL/electron injection layer EIL, or hole blocking layer/electron transport layer ETL/electron injection layer EIL, laminated in order from the emission layer EML, as examples. The thickness of the electron transport region ETR may be, for example, from about 1,000 Å to about 1,500 Å.

The electron transport region ETR may be formed using a suitable method such as a vacuum deposition method, a spin coating method, a cast method, a Langmuir-Blodgett (LB) method, an inkjet printing method, a laser printing method, and a laser induced thermal imaging (LITI) method.

When the electron transport region ETR includes the electron transport layer ETL, the electron transport region ETR may include a suitable material. For example, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2.9-dimethyl-4,7-diphenyl-1, 10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof.

When the electron transport region ETR includes the electron transport layer ETL, the thickness of the electron transport layer ETL may be from about 100 Å to about 1,000 Å, or, for example, from about 150 Å to about 500 Å. If the thickness of the electron transport layer ETL satisfies the above-described range, satisfactory electron transport properties may be obtained without a substantial increase of the driving voltage.

When the electron transport region ETR includes the electron injection layer EIL, the electron injection layer EIL may include a suitable electron injection material. For example, the electron transport region ETR may include LiF, lithium quinolate (Liq), Li$_2$O, BaO, NaCl, CsF, a lanthanoide metal i such as Yb, or a metal halide such as RbCl and RbI. The electron injection layer EIL also may be formed using a mixture material of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate.

When the electron transport region ETR includes the electron injection layer EIL, the thickness of the electron injection layer EIL may be from about 1 Å to about 100 Å, or, for example, from about 3 Å to about 90 Å. When the thickness of the electron injection layer EIL satisfies the above described range, satisfactory electron injection properties may be obtained without inducing a substantial increase of the driving voltage.

The electron transport region ETR may include a hole blocking layer, as described above. The hole blocking layer may include, for example, at least one of 2,9-dimethyl-4,7-diphenyl-1,10-phenanthroline (BCP) or 4,7-diphenyl-1,10-phenanthroline (Bphen).

The second electrode EL2 may be disposed on the electron transport region ETR. The second electrode EL2 has conductivity. The second electrode EL2 may be formed using a metal alloy or a conductive compound. The second electrode EL2 may be a cathode. The second electrode EL2 may be a transmissive electrode, a transflective electrode or a reflective electrode. When the second electrode EL2 is the transmissive electrode, the second electrode EL2 may be formed using transparent metal oxides, for example, ITO, IZO, ZnO, ITZO, etc.

When the second electrode EL2 is the transflective electrode or the reflective electrode, the second electrode EL2 may include Ag, Mg, Cu, Al, Pt. Pd. Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected to an auxiliary electrode. When the second electrode EL2 is connected to the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

When the organic electroluminescence device 10 is a top emission type, the first electrode EL1 may be a reflective electrode, and the second electrode EL2 may be a transmissive electrode or a transflective electrode. When the organic electroluminescence device 10 is a bottom emission type, the first electrode EL1 may be a transmissive electrode or a transflective electrode, and the second electrode EL2 may be a reflective electrode.

The organic electroluminescence device according to an embodiment includes the polycyclic compound according to an embodiment, thereby securing high emission efficiency.

Furthermore, in the organic electroluminescence device according to an embodiment including the above-described polycyclic compound having a high level of the lowest triplet energy in the hole transport region, the diffusion of triplet excitons generated in the emission layer may be inhibited. Thereby, high external quantum efficiency may be obtained.

The organic electroluminescence device according to an embodiment may be a blue light emitting device, a green light emitting device, a red light emitting device or a white light emitting device. An organic electroluminescence device that is a blue light emitting device according to an embodiment may have high emission efficiency, when it.

The following Examples and Comparative Examples are provided in order to highlight characteristics of one or more embodiments, but it is to be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Polycyclic Compounds

The synthetic method of polycyclic compounds according to embodiments will be explained in more detail by illustrating the synthetic method of Compounds 1, 3, 9 and 13 in Compound Group 1, as exemplary embodiments.

(Synthesis of Compound 3)

Compound 3, a polycyclic compound according to an embodiment, may be synthesized, for example, by the following reaction.

Under an argon atmosphere, 200 mL of toluene was added to 6.0 g of 10,10-diphenyl-phenazasiline, 4.48 g of 4-bromobenzophenone, 1.40 g of [1,1'-bis(diphenylphosphino)ferrocene]dichloropalladium (II) and 4.95 g of sodium-tert-butoxide, and the mixture was heated to reflux for about 8 hours. After cooling to room temperature, the resulting solution was filtered and 100 mL of ethanol was added thereto. Precipitated crystals were filtered and washed sequentially with 50 mL of water and 100 mL of ethanol to obtain 7.1 g (yield 78%) of Intermediate 1 (M1) as a pale yellow powder.

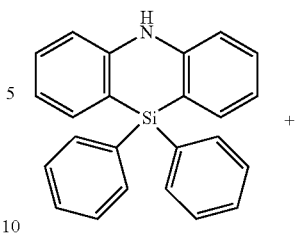

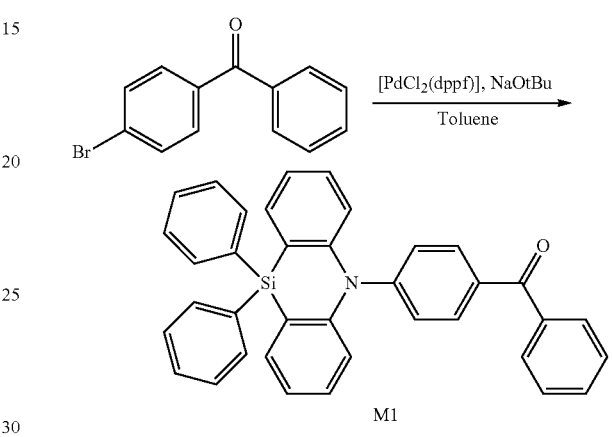

Under an argon atmosphere, 20 mL n-BuLi 15% hexane solution was added to 100 mL of THF solution containing 4.13 g of o-bromotriphenylamine cooled to about −78° C. The temperature was elevated to room temperature, and the resultant was stirred for about 3 hours. 100 mL of THE solution containing 16.75 g of Intermediate 1 was added thereto dropwisely for about 3 hour at about −78° C. The resultant was stirred at room temperature for about 1 day, and then concentrated. Precipitated crystals were purified by column chromatography (toluene:hexane 1:1) and recrystallized with toluene/ethanol to obtain 7.9 g (yield 80%) of Intermediate 2 (M2) as a white powder.

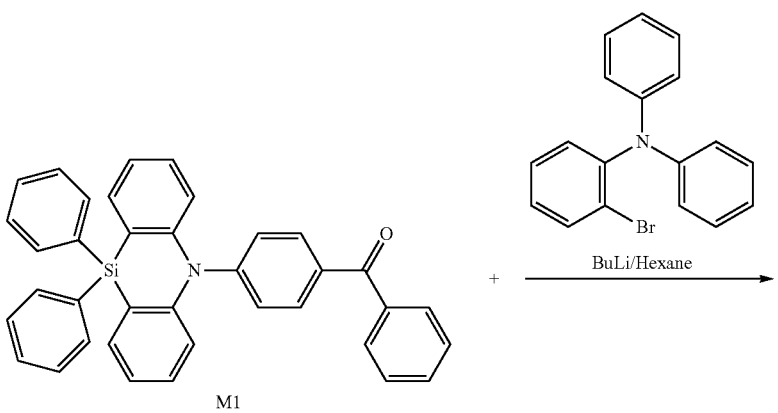

-continued

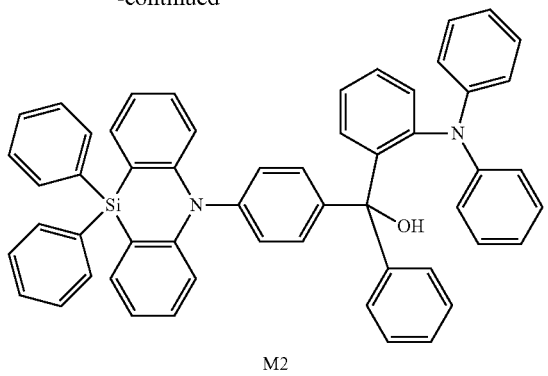

M2

6.75 g of Intermediate 2 (M2) was refluxed with 1 g of Eaton reagent and 100 mL of toluene for about 12 hour. After cooling to room temperature, precipitated crystals were filtered and washed sequentially with 100 mL of water and 100 mL of ethanol to obtain 4.6 g (yield 70%) of Compound 3 as a white solid. The structure of product was identified using FAB-MS. (m/z 756.3 (M+), 757.3 (MH+))

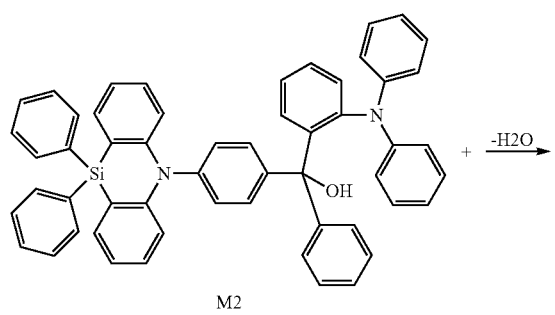

M2

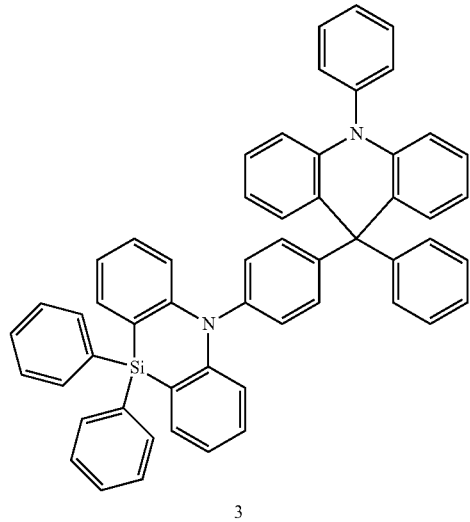

3

(Synthesis of Compound 1)

Compound 1 was synthesized by conducting the same synthetic method used to form Compound 3, except for using 5.7 g of 9,9-diphenyl-9,10-dihydroacridine instead of 6.0 g of 10,10-diphenyl-phenazasiline in the synthetic method. 4.4 g (yield 67%) of Compound 1 was obtained as a white solid. The structure of product was identified using FAB-MS. (m/z 740.3 (M+), 741.3 (MH+))

(Synthesis of Compound 9)

Compound 9 was synthesized by conducting the same synthetic method used to form Compound 3, except for using 6.0 g of spiro[acridine-9(10H),9'-[9H]fluorene] instead of 6.0 g of 10,10-diphenyl-phenazasiline in the synthetic method. 5.1 g (yield 78%) of Compound 9 was obtained as a white solid. The structure of product was identified using FAB-MS. (m/z 738.3 (M+), 739.3 (MH+))

(Synthesis of Compound 13)

Compound 13 was synthesized by conducting the same synthetic method used to form Compound 3 except for using 4.48 g of 3-bromobenzophenone instead of 4.48 g of 4-bromobenzophenone in the synthetic method. 3.1 g (yield 47%) of Compound 13 was obtained as a white solid. The structure of product was identified using FAB-MS. (m/z 756.3 (M+), 757.3 (MH+))

2. Manufacturing of Organic Electroluminescence Devices Including Polycyclic Compounds and Evaluation Thereof (Manufacturing of Organic Electroluminescence Devices)

Organic electroluminescence devices according to an embodiment including the polycyclic compounds according to embodiments in the hole transport region were manufactured by the following method. The devices were manufactured separately as Configuration 1 and Configuration 2. In the following examples, Configuration 1 represents the organic electroluminescence devices including the polycyclic compound in the electron blocking layer of the hole transport region, and Configuration 2 represents the organic electroluminescence devices including the polycyclic compound in the hole transport layer of the hole transport region.

For example, in Configuration 1, the organic electroluminescence devices of Examples 1 to 4 were manufactured by using Compounds 1, 3, 9 and 13 as electron blocking layer materials. The organic electroluminescence devices of Examples 5 and 6 correspond to Configuration 2, in which Compounds 3 and 9, were used respectively, as hole transport layer materials.

In the organic electroluminescence devices of Configuration 1, the electron blocking layer including he polycyclic compound according to an embodiment may be a thin layer. In the organic electroluminescence devices of Configuration 2, the hole transport layer including the polycyclic compound may be a thick layer. In Configuration 2, the hole transport layer may also serve as an electron blocking layer. In this case, a process of forming an electron blocking layer separately may be omitted, thereby increasing productivity.

The organic electroluminescence devices of Examples and Comparative Examples were manufactured by the following method.

For the organic electroluminescence devices of Configuration 1, ITO was patterned on a glass substrate to a thickness of about 1,500 Å, followed by washing with ultrapure water and performing a UV ozone treatment for about 10 minutes. After that, a hole injection layer was formed using HAT-CN to a thickness of about 100 Å, and then a hole transport layer HTL was formed using α-NPD to a thickness of about 800 Å. Next, an electron blocking layer EBL was formed using an Example Compound or a Comparative Compound to a thickness of about 50 Å.

Next, an emission layer was formed using bis{2-[di (phenyl) phosphino]phenyl}ether oxide (DPEPO) doped with a dopant to a thickness of about 200 Å. As a dopant in the emission layer, 18% 10-phenyl-10H,10'H-spiro[acridine-9,9'-anthracen]-10'-one (ACRSA) was used in Examples 1 to 4 and Comparative Examples 1, 4 and 5, and 25% 2,5,8,11-tetra-tert-butylperylene (TBPe) was used in Comparative Example 2.

A hole blocking layer was formed using DPEPO to a thickness of about 100 Å, an electron transport layer was formed using 1,3,5-tris(1-phenyl-1H-benzimidazol-2-yl) benzene (TPBi) to a thickness of about 300 Å, and an electron injection layer was formed using LiF to a thickness of about 5 Å. A second electrode was formed using Al to a thickness of about 1,000 Å.

In the Examples, the hole injection layer, hole transport layer, electron blocking layer, emission layer, hole blocking layer, electron transport layer, electron injection layer and second electrode were formed by a vacuum deposition method.

The organic electroluminescence devices of Comparative Examples 1 and 2 were manufactured by the same manufacturing method of the organic electroluminescence devices of Examples except for using mCP in the electron blocking layer. The organic electroluminescence devices of Comparative Examples 4 and 5 were manufactured by the same manufacturing method as the organic electroluminescence devices of Examples except for using Comparative Compounds C2 and C3 in the respective electron blocking layers.

For the organic electroluminescence devices of Configuration 2, ITO was patterned on a glass substrate to a thickness of about 1,500 Å, followed by washing with ultrapure water and performing a UV ozone treatment for about 10 minutes. After that, a hole injection layer was formed using HAT-CN to a thickness of about 100 Å. Next, a hole transport layer HTL was formed using an Example Compound or a Comparative Compound to a thickness of about 1,000 Å.

Next, an emission layer was formed using bis{2-[di (phenyl) phosphino]phenyl}ether oxide (DPEPO) doped with a dopant to a thickness of about 200 Å. As a dopant in the emission layer, 18% 10-phenyl-10H,10'H-spiro[acridine-9,9'-anthracen]-10'-one (ACRSA) was used in Examples 5 and 6 and Comparative Example 3.

A hole blocking layer was formed using DPEPO to a thickness of about 100 Å, an electron transport layer was formed using 1,3,5-tris(1-phenyl-1H-benzimidazol-2-yl) benzene (TPBi) to a thickness of about 300 Å, and an electron injection layer was formed using LiF to a thickness of about 5 Å. A second electrode was formed using Al to a thickness of about 1000 Å.

In Examples, the hole injection layer, hole transport layer, electron blocking layer, emission layer, hole blocking layer, electron transport layer, electron injection layer and second electrode were formed by a vacuum deposition method.

The organic electroluminescence device of Comparative Example 3 was manufactured by the same manufacturing method as the organic electroluminescence devices of Examples except for using Comparative Compound C1 in the hole transport layer.

The compounds used for manufacturing organic electroluminescence devices are shown as follows.

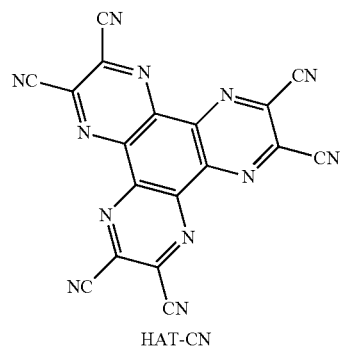
HAT-CN

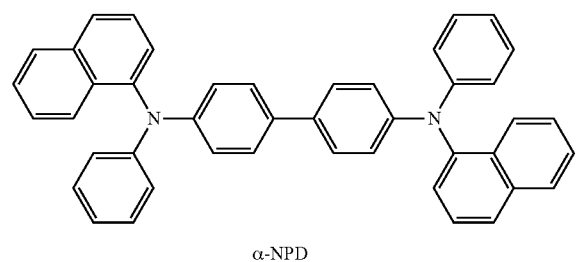
α-NPD

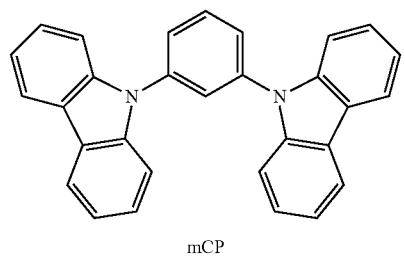
mCP

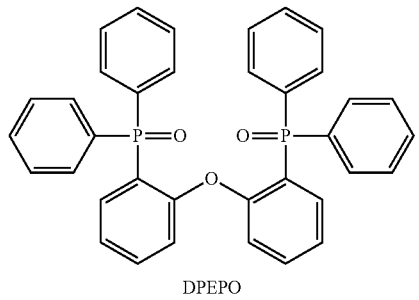
DPEPO

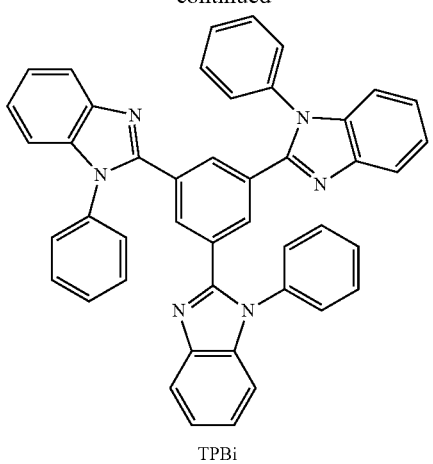

TPBi

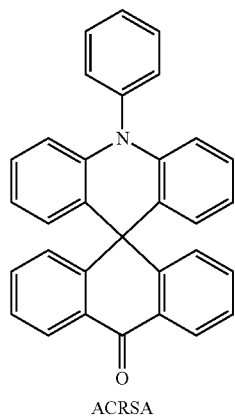

ACRSA

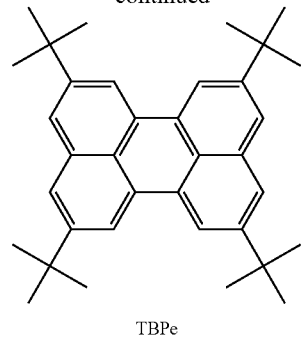

TBPe

Table 1 shows the configuration of organic electroluminescence devices used in Examples and Comparative Examples.

TABLE 1

| Examples | Configuration | HTL | EBL | Dopant |
|---|---|---|---|---|
| Example 1 | Configuration 1 | a-NPD | Compound 1 | ACRSA |
| Example 2 | Configuration 1 | a-NPD | Compound 3 | ACRSA |
| Example 3 | Configuration 1 | a-NPD | Compound 9 | ACRSA |
| Example 4 | Configuration 1 | a-NPD | Compound 13 | ACRSA |
| Example 5 | Configuration 2 | Compound 3 | — | ACRSA |
| Example 6 | Configuration 2 | Compound 9 | — | ACRSA |
| Comparative Example 1 | Configuration 1 | a-NPD | mCP | ACRSA |
| Comparative Example 2 | Configuration 1 | a-NPD | mCP | TBPe |
| Comparative Example 3 | Configuration 2 | Comparative Compound C1 | — | ACRSA |
| Comparative Example 4 | Configuration 1 | a-NPD | Comparative Compound C2 | ACRSA |
| Comparative Example 5 | Configuration 1 | a-NPD | Comparative Compound C3 | ACRSA |

Table 2 shows the compounds used in the electron blocking layer and the hole transport layer for Examples 1 to 6 and Comparative Examples 3 to 5.

TABLE 2

Compound 1

TABLE 2-continued
Compound 3
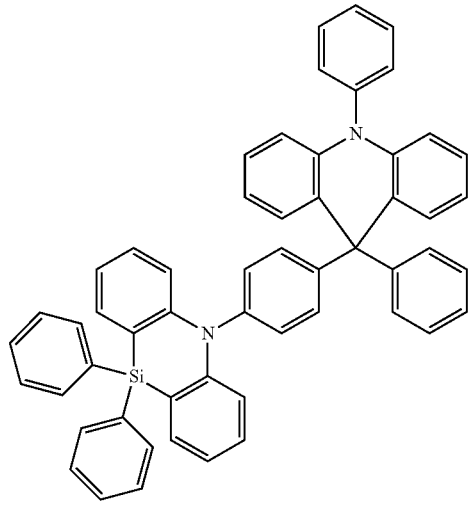
3
Compound 9
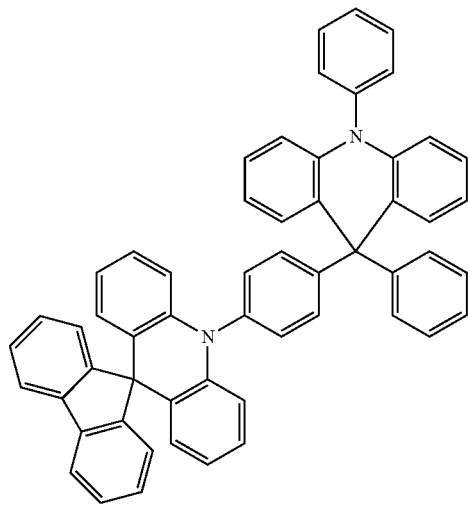
9
Compound 13
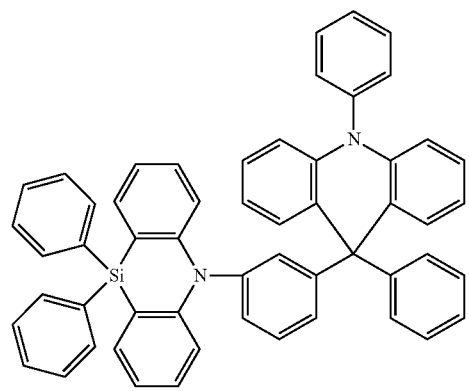
13

TABLE 2-continued

| | |
|---|---|
| Comparative Compound C1 | 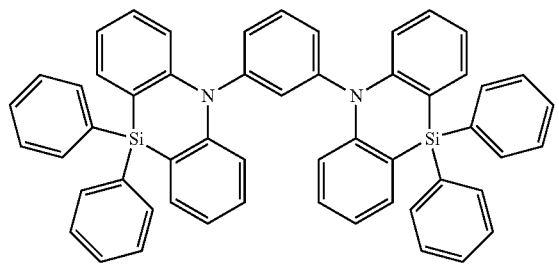<br>C1 |
| Comparative Compound C2 | 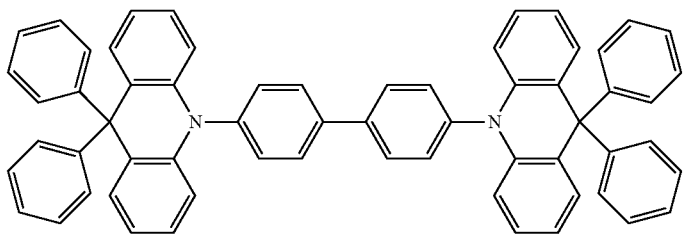<br>C2 |
| Comparative Compound C3 | 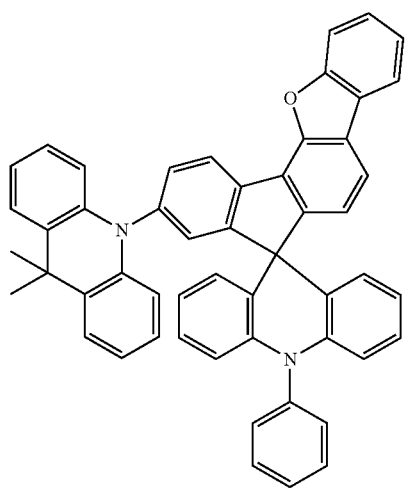<br>C3 |

(Property Evaluation of Organic Electroluminescence Devices)

The external quantum efficiency (EQE) and driving voltage at a current density of 10 mA/cm² were measured to evaluate the properties of the organic electroluminescence devices manufactured in the Examples and Comparative Examples. The voltage and current density were measured by using a source meter (Keithley Instruments, 2400 series), and the external quantum efficiency was measured by using a brightness light distribution characteristics measurement system C9920-11 (Hamamatsu Photonics, Japan). In the evaluation of external quantum efficiency, a brightness/current density were measured using a luminance meter with calibrated wavelength sensitivity, and the external quantum efficiency was calculated by assuming angular luminance distribution (Lambertian) with a postulated perfect reflecting diffuser.

Property evaluation results of the organic electroluminescence devices are shown in Table 3 below.

TABLE 3

| Examples | Driving voltage (10 mA/cm², V) | External quantum efficiency (%) |
|---|---|---|
| Example 1 | 6.4 | 17.7 |
| Example 2 | 6.6 | 17.3 |
| Example 3 | 6.2 | 16.0 |
| Example 4 | 6.8 | 16.4 |
| Example 5 | 7.6 | 18.5 |
| Example 6 | 7.2 | 17.2 |
| Comparative Example 1 | 6.6 | 15.0 |
| Comparative Example 2 | 9 | 0.4 |
| Comparative Example 3 | 8.3 | 17.1 |
| Comparative Example 4 | 6.8 | 14.5 |
| Comparative Example 5 | 6.2 | 12.6 |

The configuration of organic electroluminescence devices of Examples 1 to 6 and Comparative Examples 1 to 5 corresponds to that shown in Table 1.

Referring to the results in Table 3, it may be seen that the organic electroluminescence devices of Examples 1 to 6 have enhanced external quantum efficiency when compared with those of Comparative Examples 1, 2, 4 and 5. Furthermore, it may be seen that while the organic electroluminescence devices of Examples 1 to 6 have an external quantum efficiency similar to that of Comparative Example 3, the organic electroluminescence devices of Examples 1 to 6 have a decreased driving voltage at a current density of 10 mA/cm$^2$.

According to the above results, it may be concluded that the organic electroluminescence device including a polycyclic compound according to embodiments in the hole transport region may attain a low driving voltage as well as high emission efficiency.

Table 4 shows the lowest triplet excitation energy (T1) of Compounds 1, 3, 9 and 13 used in the electron blocking layer of Examples, of mCP used in the electron blocking layer of Comparative Examples, and of Comparative Compounds C1, C2 and C3. The lowest triplet excitation energy (T1) is a value calculated theoretically by simulation program Gaussian 09.

TABLE 4

| Compound | Lowest triplet excitation energy (eV) |
| --- | --- |
| Compound 1 | 3.29 |
| Compound 3 | 3.31 |
| Compound 9 | 3.20 |
| Compound 13 | 3.30 |
| mCP | 3.18 |
| Comparative Compound C1 | 3.30 |
| Comparative Compound C2 | 3.13 |
| Comparative Compound C3 | 2.81 |

Referring to the results in Table 4, it may be seen that Compounds 1, 3, 9 and 13, as the polycyclic compounds used in the Examples, have the lowest triplet excitation energy (T1) of 3.2 eV or higher, which is higher than the lowest triplet excitation energy (T1) of mCP, and of Comparative Compounds C2 and C3 used in Comparative Examples 1 and 2, and Comparative Examples 4 and 5, respectively. It may also be seen that Comparative Compound C1 used in Comparative Example 3 has the lowest triplet excitation energy similar to those of Example Compounds.

Accordingly, referring to the results in Tables 3 and 4, it may be seen that the organic electroluminescence devices using Example Compounds 1, 3, 9 and 13 with a relatively high level of the lowest triplet excitation energy showed higher external quantum efficiency, by the effect of the high level of the lowest triplet excitation energy, when compared with the organic electroluminescence devices of Comparative Examples 1, 2, 4 and 5. It may also be seen that the organic electroluminescence device of Comparative Example 3 using Comparative Compound C1 with the lowest triplet excitation energy similar to those of Example Compounds 1, 3, 9 and 13 showed external quantum efficiency similar to those of Examples while requiring a higher driving voltage when compared with the organic electroluminescence devices of the Examples.

Furthermore, it may be seen that the organic electroluminescence devices of Configuration 1 in the Examples, which includes a polycyclic compound according to an embodiment in the electron blocking layer showed higher emission efficiency and lower driving voltage when compared with organic electroluminescence devices using the general materials of the Comparative Examples in an electron blocking layer. It is believed that such results are due to a higher level of the lowest triplet excitation energy and higher hole transport property of the polycyclic compound according to an embodiment when compared with the level of the lowest triplet excitation energy and hole transport property of the materials used in Comparative Examples. The organic electroluminescence device according to an embodiment may attain high emission efficiency by including the polycyclic compound according to an embodiment in a hole transport region. The polycyclic compound according to an embodiment may be included in a hole transport region, and therefore, may improve the external quantum efficiency of an organic electroluminescence device, and may attain a lower driving voltage when compared with the case of similar external quantum efficiency.

By way of summation and review, in an application of an organic electroluminescence device to a display, a decrease of a driving voltage, an increase of emission efficiency and an extension of life for the organic electroluminescence device are desirable. The development of materials that may stably implement these characteristics in an organic electroluminescence is also continuously desired.

Embodiments relate to a polycyclic compound that may be used in a hole transport region of an organic electroluminescence device to provide high efficiency.

The polycyclic compound according to an embodiment may improve the emission efficiency of an organic electroluminescence device.

The organic electroluminescence device according to an embodiment may attain high efficiency by including the polycyclic compound according to an embodiment in a hole transport region.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. A polycyclic compound represented by the following Formula 1:

[Formula 1]

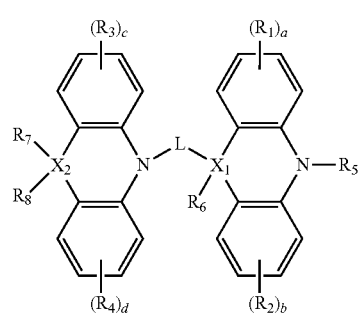

where $X_1$ and $X_2$ are each independently any one of C, Si, Ge, or Sn,

L is a substituted or unsubstituted arylene group having 6 to 30 ring carbon atoms, or a substituted or unsubstituted heteroarylene group having 2 to 30 ring carbon atoms, $R_1$ to $R_4$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_5$ is a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_6$ to $R_8$ are each independently a substituted or unsubstituted alkyl group having 1 to 20 carbon atoms, a substituted or unsubstituted alkoxy group having 1 to 20 carbon atoms, a substituted or unsubstituted aryloxy group having 6 to 30 ring carbon atoms, a substituted or unsubstituted aryl group having 6 to 30 ring carbon atoms, or a substituted or unsubstituted heteroaryl group having 2 to 30 ring carbon atoms, or $R_6$ to $R_8$ may form a ring by combining adjacent groups with each other, and a to d are each independently an integer of 1 to 4.

2. The polycyclic compound as claimed in claim 1, wherein at least one of $X_1$ or $X_2$ is Si.

3. The polycyclic compound as claimed in claim 1, wherein one of $X_1$ or $X_2$ is any one of Si, Ge, or Sn, and the other one of $X_1$ or $X_2$ is C.

4. The polycyclic compound as claimed in claim 1, wherein L is a substituted or unsubstituted phenylene group, or a substituted or unsubstituted divalent biphenyl group.

5. The polycyclic compound as claimed in claim 4, wherein L is represented by any one of the following L-1 to L-4:

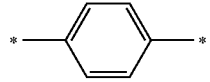

L-1

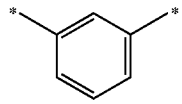

L-2

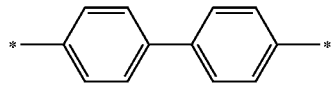

L-3

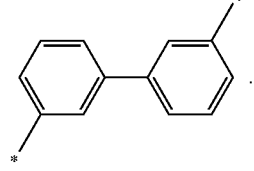

L-4

6. The polycyclic compound as claimed in claim 1, wherein L is a substituted or unsubstituted heteroarylene group including one of N, O, or S as a hetero atom.

7. The polycyclic compound as claimed in claim 6, wherein L is represented by one of the following L-5 to L-7:

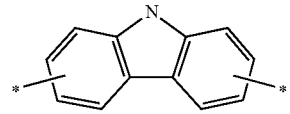

L-5

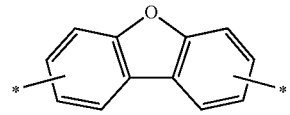

L-6

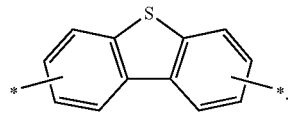

L-7

8. The polycyclic compound as claimed in claim 1, wherein $R_5$ is a methyl group, or a substituted or unsubstituted phenyl group.

9. The polycyclic compound as claimed in claim 1, wherein $R_6$ is a methyl group, or a substituted or unsubstituted phenyl group.

10. The polycyclic compound as claimed in claim 1, wherein $R_7$ and $R_8$ are each independently a methyl group, or a substituted or unsubstituted phenyl group, or combine with each other to form a substituted or unsubstituted fluorene ring.

11. The polycyclic compound as claimed in claim 1, wherein the polycyclic compound represented by Formula 1 is any one selected from the group consisting of compounds represented in the following Compound Group 1:

[Compound Group 1]

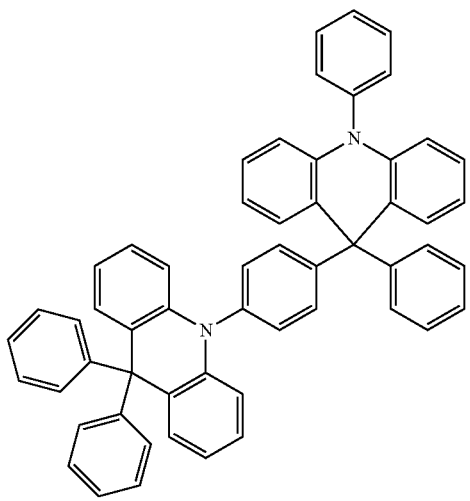

1

2
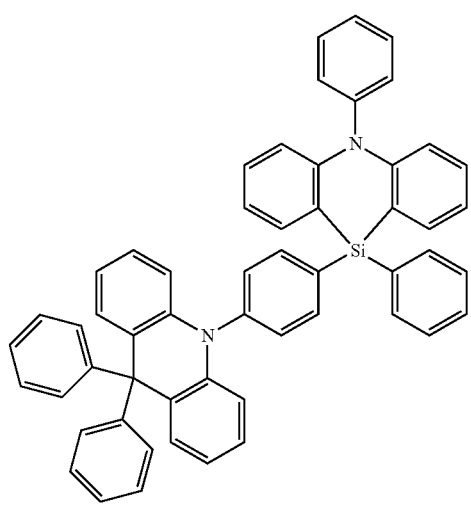
3
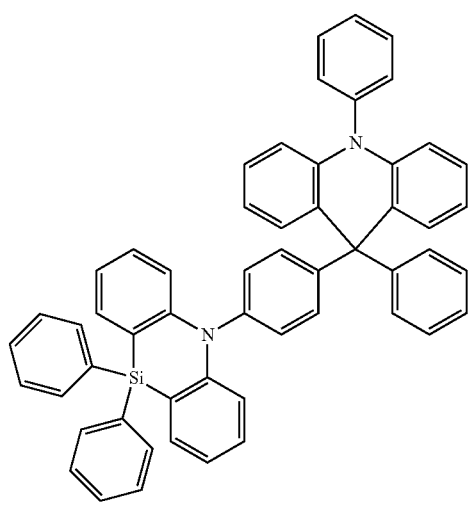
4
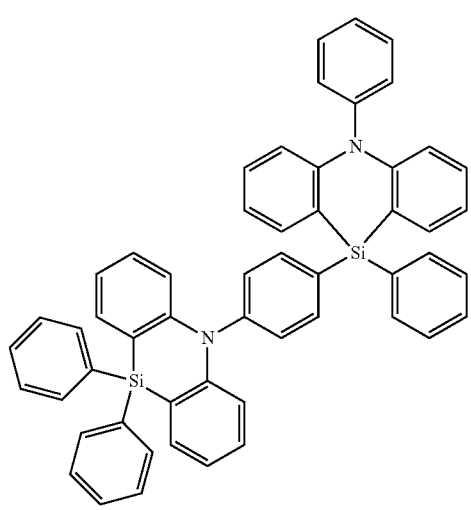
5
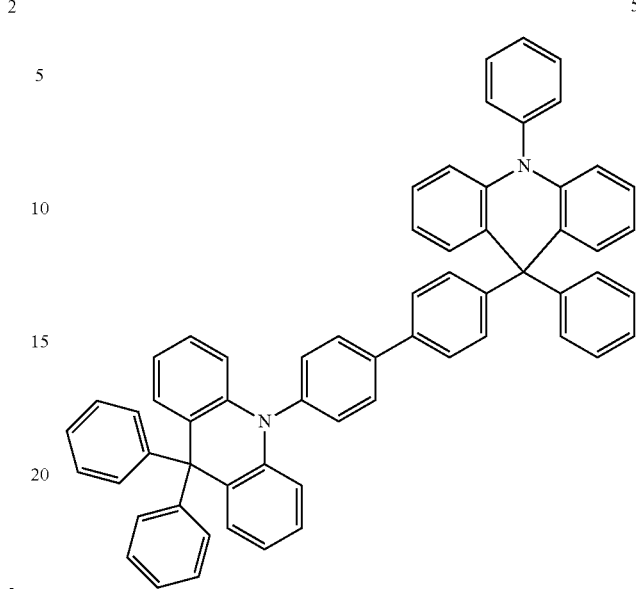
6
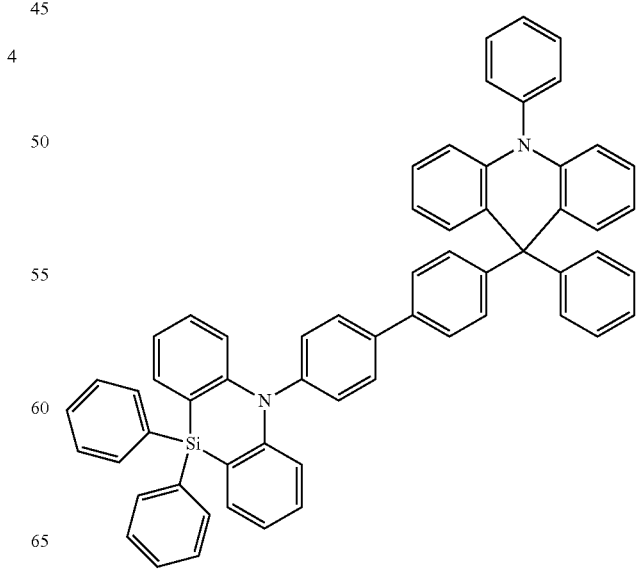

-continued
7
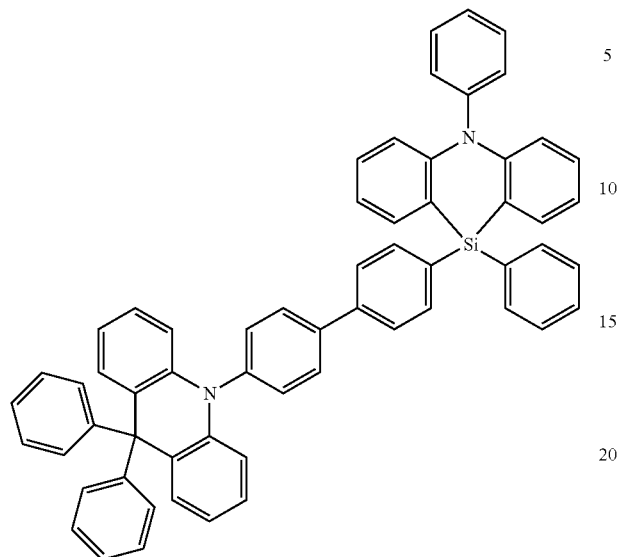
8
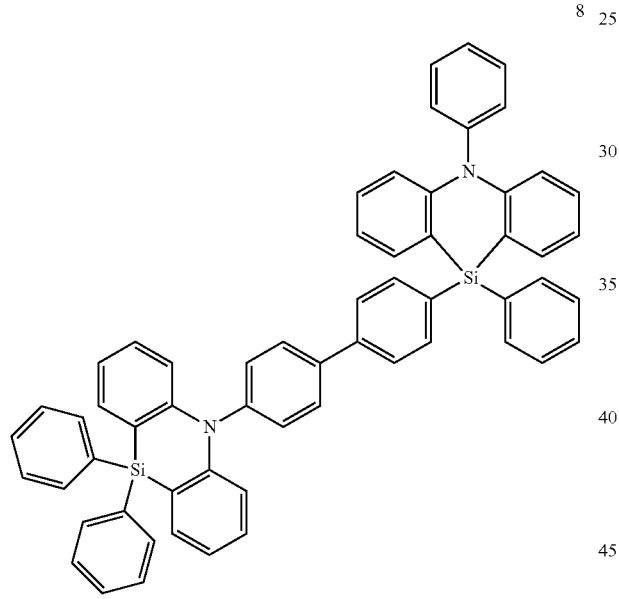
9
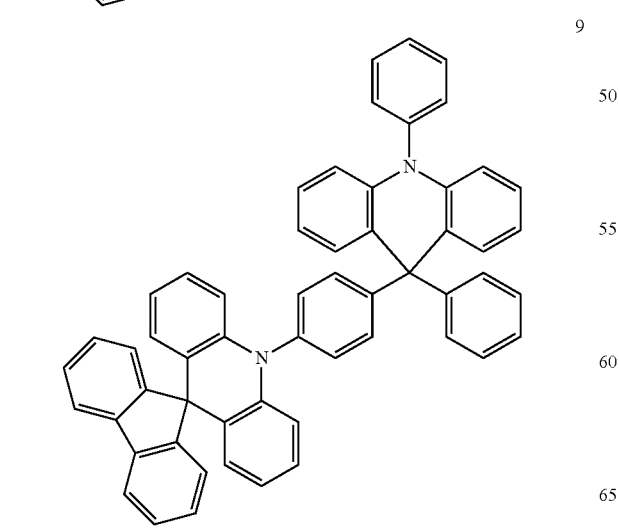
-continued
10
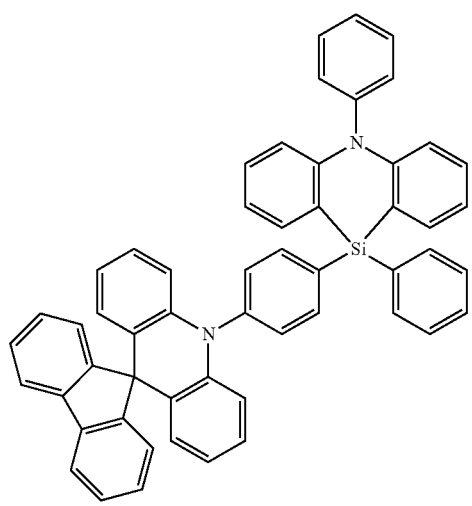
11
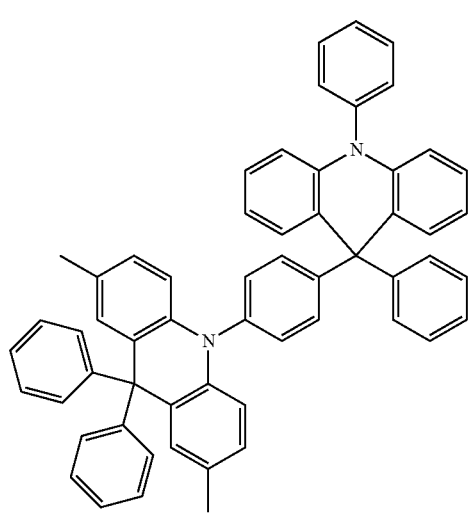
12
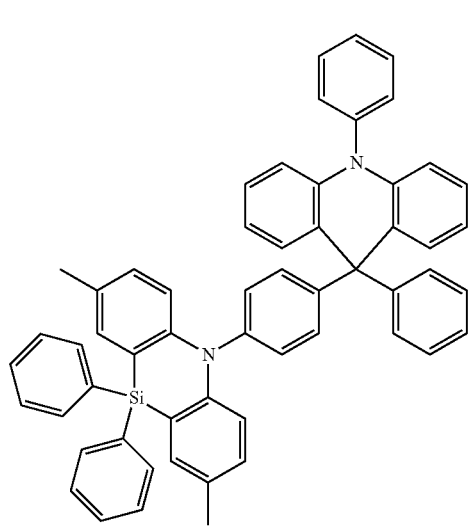

13
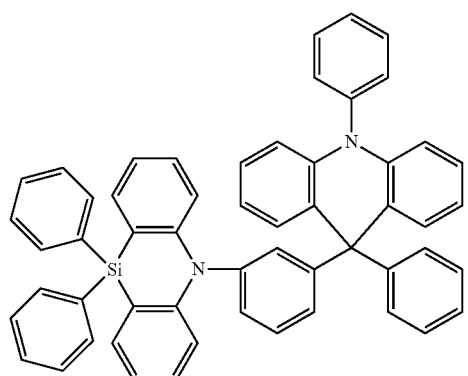
14
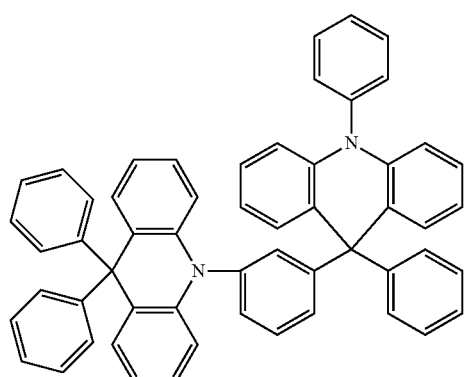
15
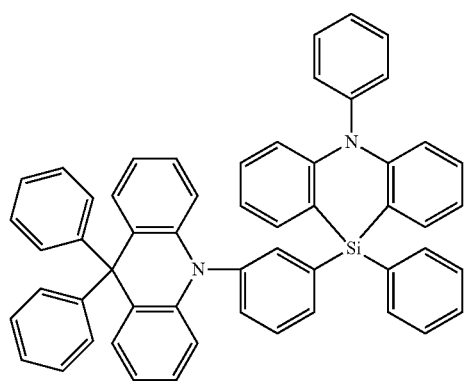
16
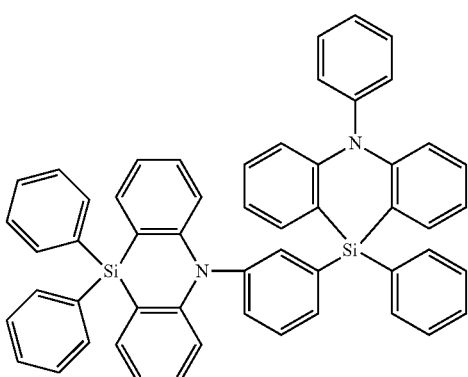
17
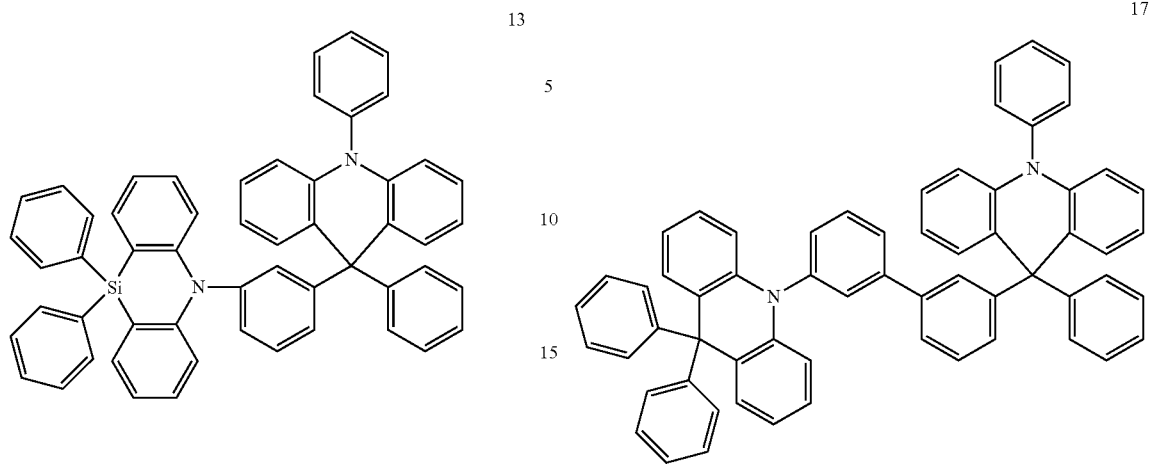
18
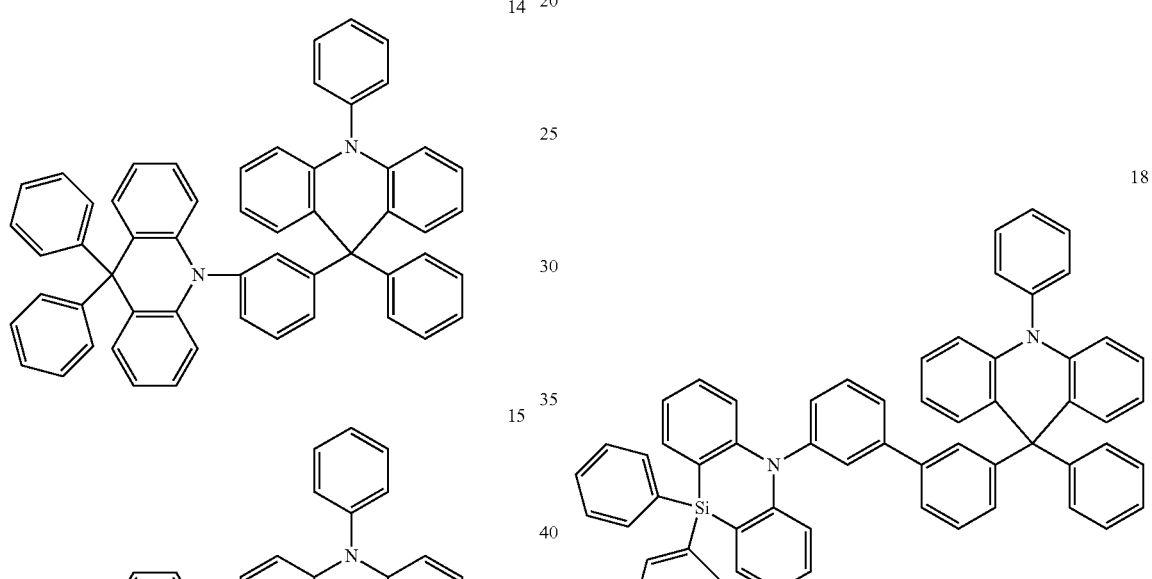
19
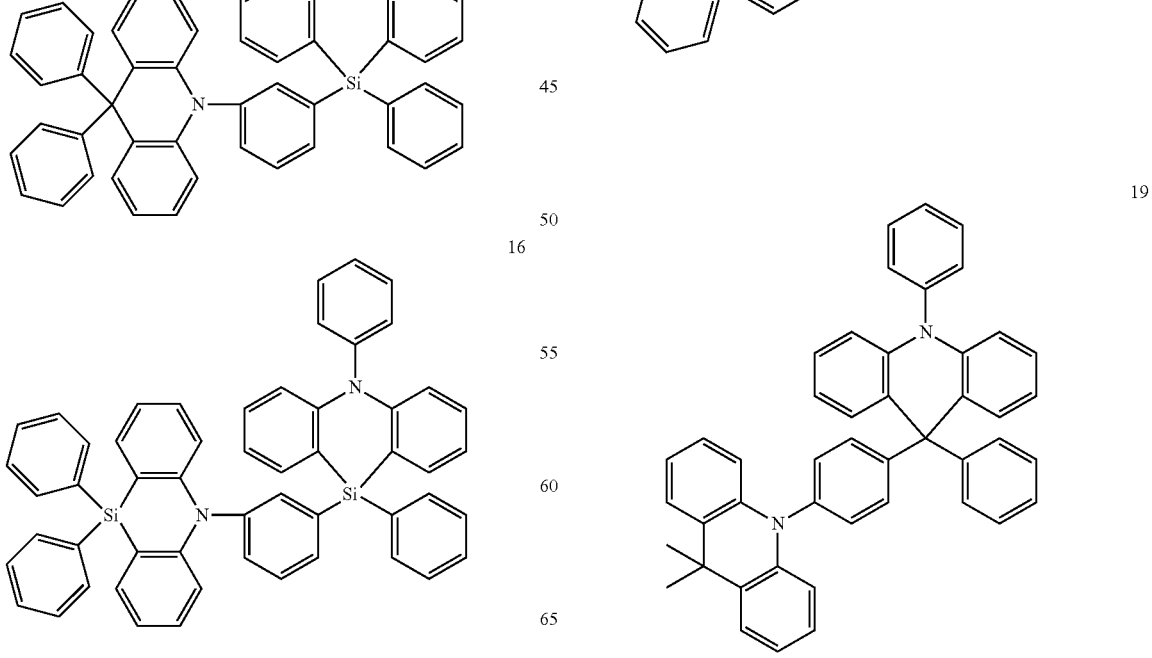

77
-continued
20
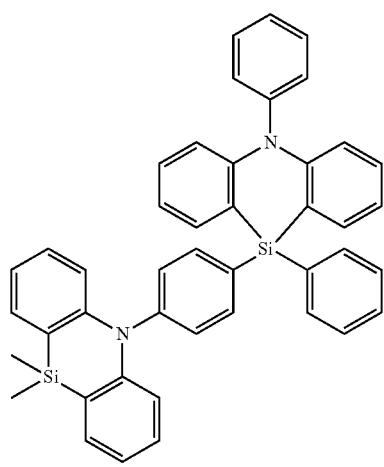
21
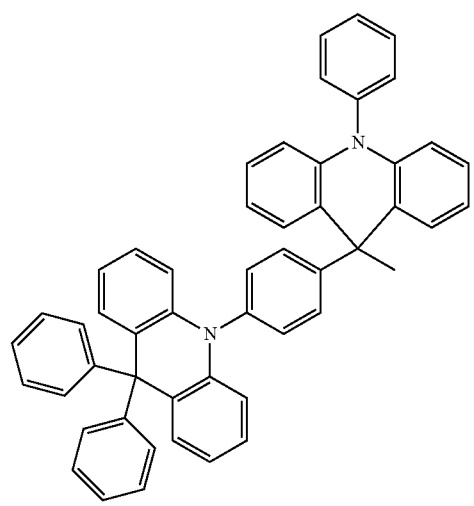
22
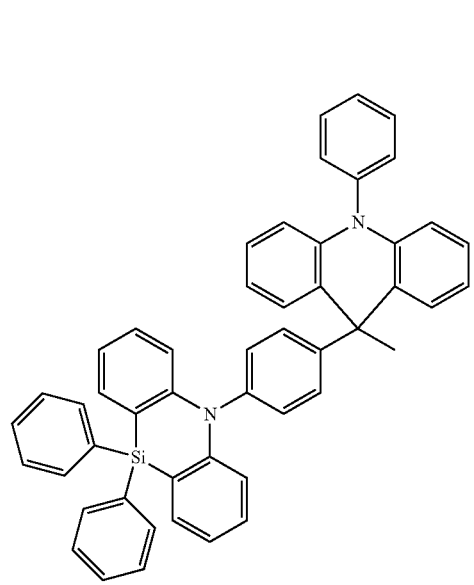
78
-continued
23
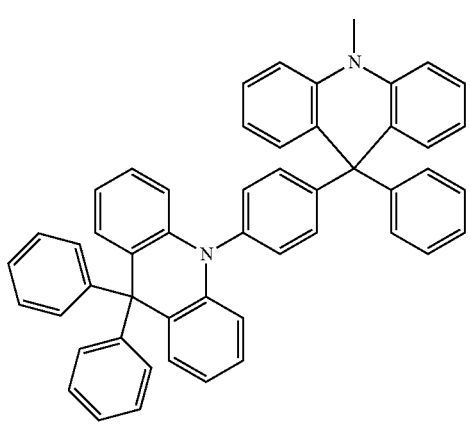
24
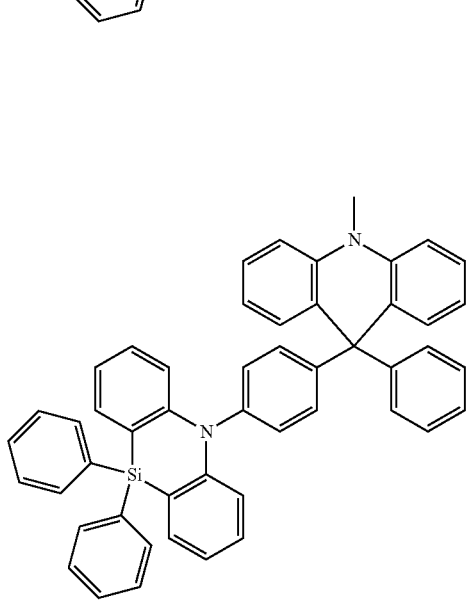
25
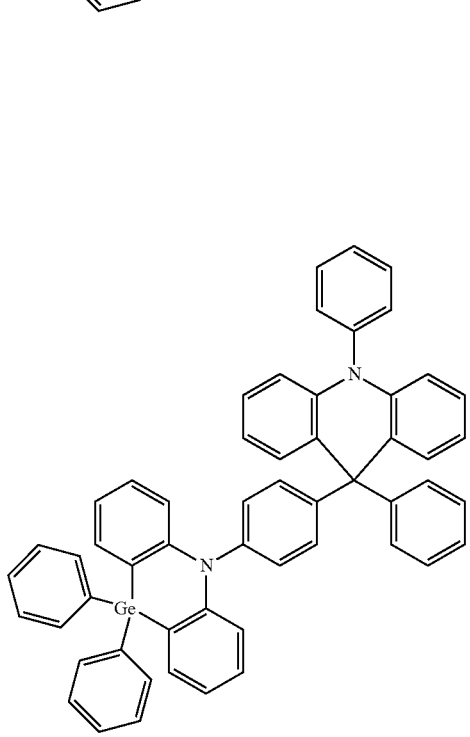

26
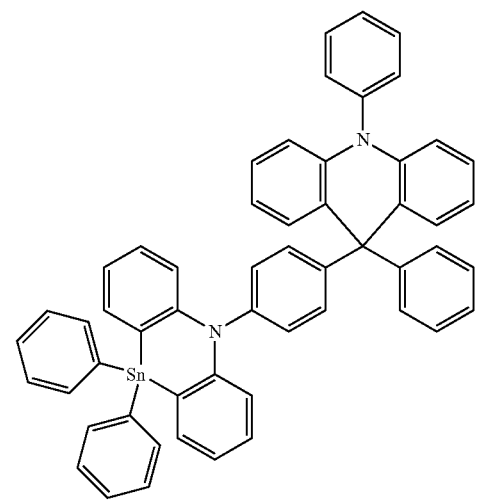
27
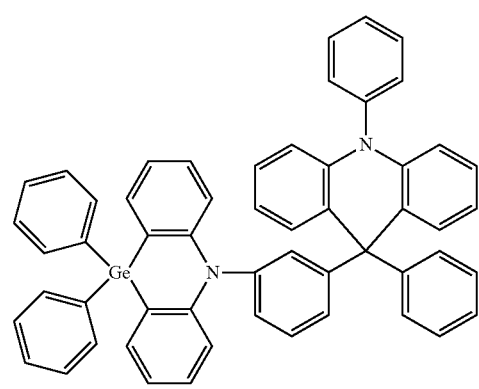
28
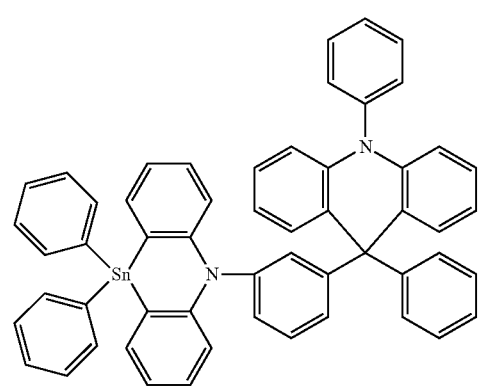
29
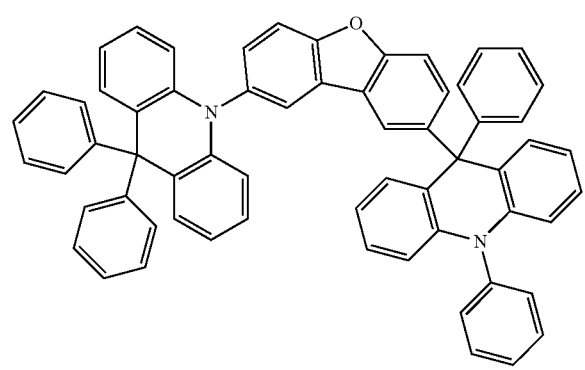
30
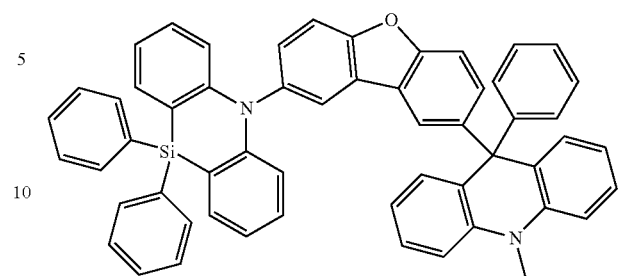
31
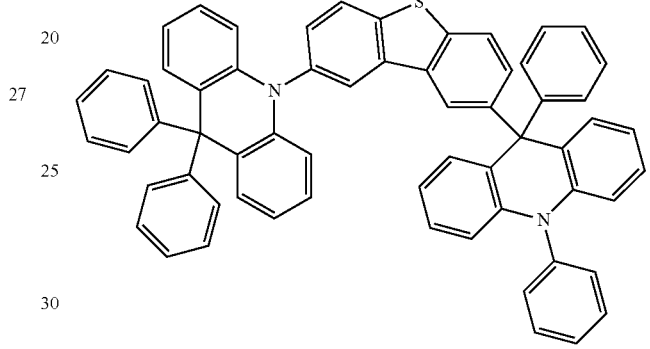
32
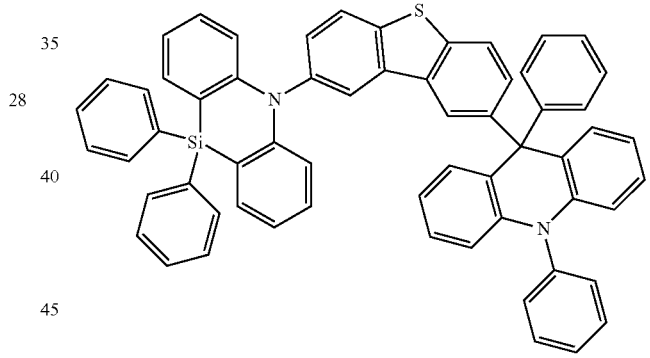
33
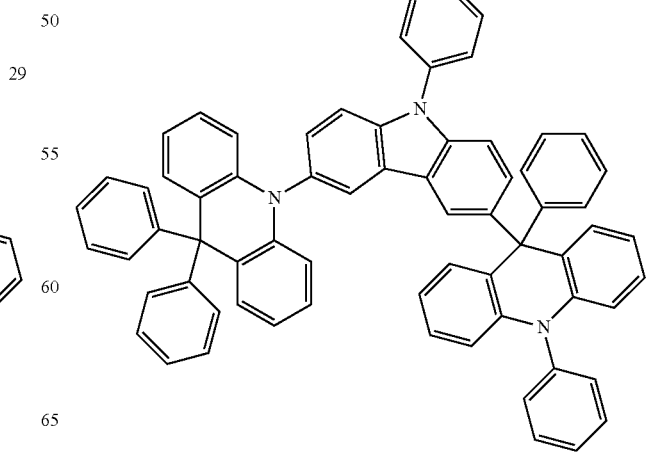

-continued
34
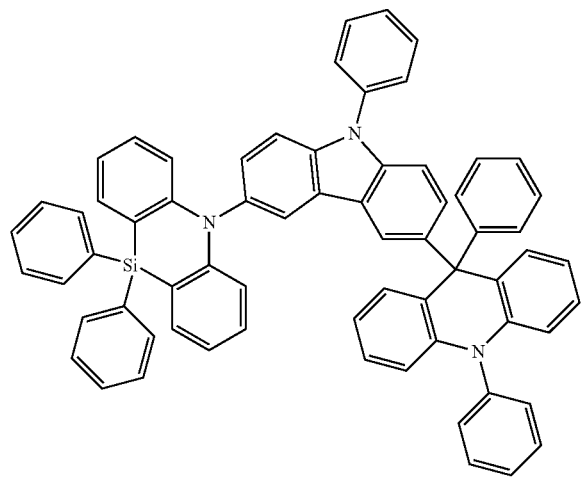
35
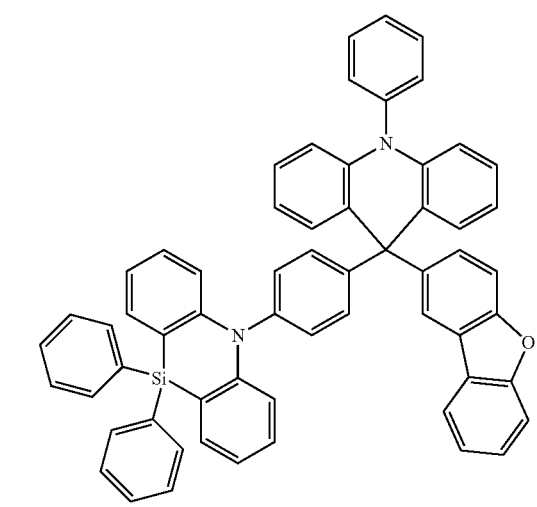
36
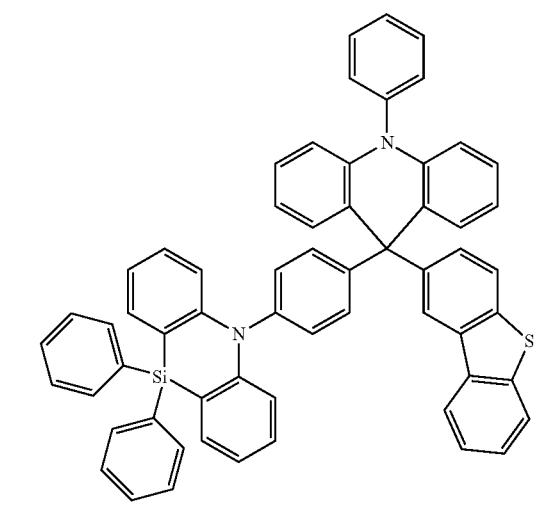
-continued
37
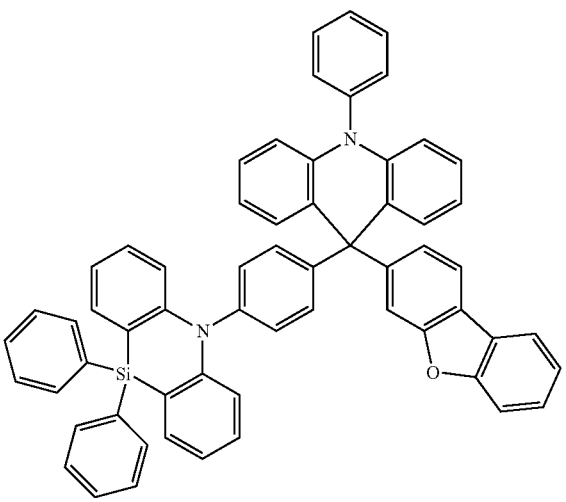
38
39

-continued

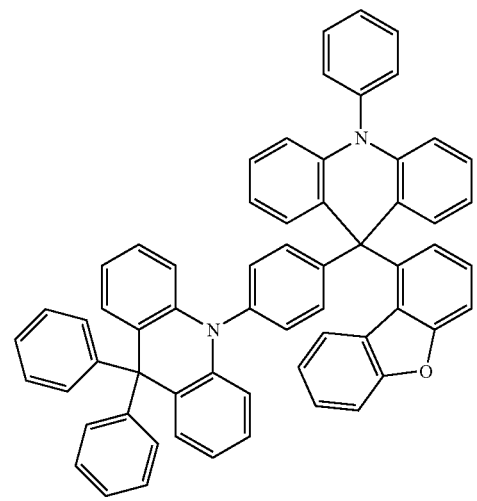

40

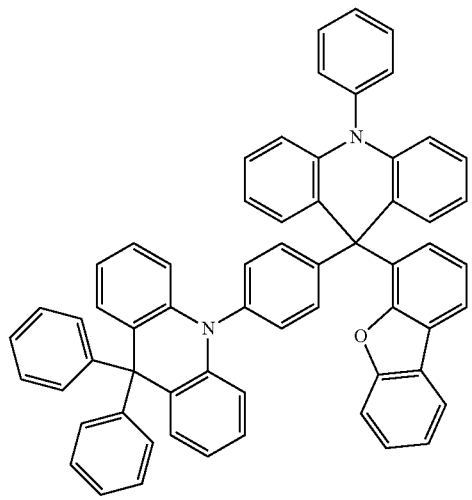

41

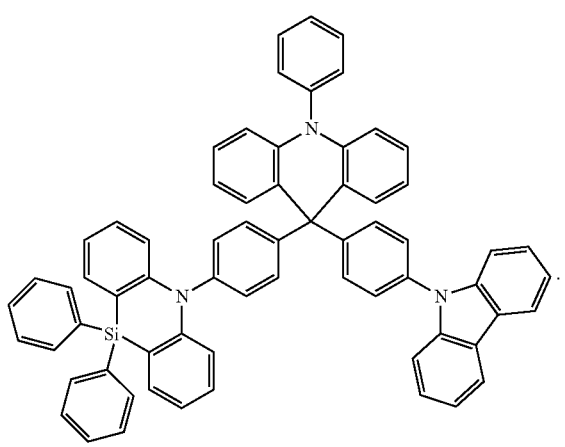

42

12. An organic electroluminescence device, comprising:
a first electrode;
a hole transport region on the first electrode;
an emission layer on the hole transport region;
an electron transport region disposed on the emission layer; and
a second electrode on the electron transport region,
wherein the hole transport region includes a polycyclic compound represented by the following Formula 1:

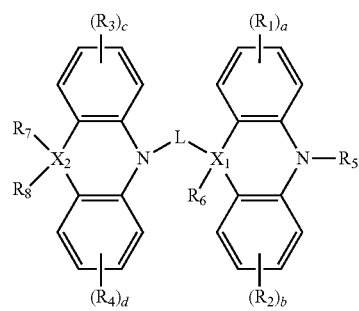

[Formula 1]

where $X_1$ and $X_2$ are each independently any one of C, Si, Ge, or Sn,
L is a substituted or unsubstituted arylene group having 6 to 30 ring carbon atoms, or a substituted or unsubstituted heteroarylene group having 2 to 30 ring carbon atoms,
$R_1$ to $R_4$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having ring 6 to 30 ring carbon atoms, or a substituted or unsubstituted heteroaryl group having 2 to 30 ring carbon atoms,
$R_5$ is a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms,
$R_6$ to $R_8$ are each independently a substituted or unsubstituted alkyl group having 1 to 20 carbon atoms, a substituted or unsubstituted alkoxy group having 1 to 20 carbon atoms, a substituted or unsubstituted aryloxy group having 6 to 30 ring carbon atoms, a substituted or unsubstituted aryl group having 6 to 30 ring carbon atoms, or a substituted or unsubstituted heteroaryl group having 2 to 30 ring carbon atoms, or $R_6$ to $R_8$ may form a ring by combining adjacent groups with each other, and
a to d are each independently an integer of 1 to 4.

13. The organic electroluminescence device as claimed in claim 12, wherein the hole transport region comprises:
a hole injection layer; and
a hole transport layer between the hole injection layer and the emission layer, and
the hole transport layer includes the polycyclic compound represented by Formula 1.

14. The organic electroluminescence device as claimed in claim 12, wherein the hole transport region includes:
a hole injection layer;
a hole transport layer on the hole injection layer; and
an electron blocking layer between the hole transport layer and the emission layer, and
the electron blocking layer includes the polycyclic compound represented by Formula 1.

15. The organic electroluminescence device as claimed in claim 12, wherein the emission layer emits blue light.

16. The organic electroluminescence device as claimed in claim 12, wherein at least one of $X_1$ or $X_2$ is Si.

17. The organic electroluminescence device as claimed in claim 12, wherein L is a substituted or unsubstituted phenylene group, a substituted or unsubstituted divalent biphenyl group, or a substituted or unsubstituted heteroarylene group including any one of N, O or S as a hetero atom.

18. The organic electroluminescence device as claimed in claim 17, wherein L is represented by any one of the following L-1 to L-7:

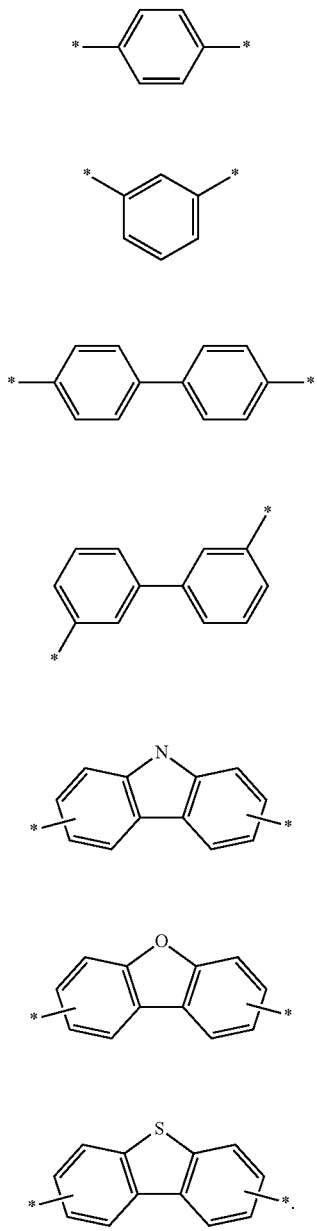

19. The organic electroluminescence device as claimed in claim 12, wherein $R_6$ is a methyl group, or a substituted or unsubstituted phenyl group.

20. The organic electroluminescence device as claimed in claim 12, wherein the hole transport region includes at least one of compounds represented in the following Compound Group 1:

[Compound Group 1]

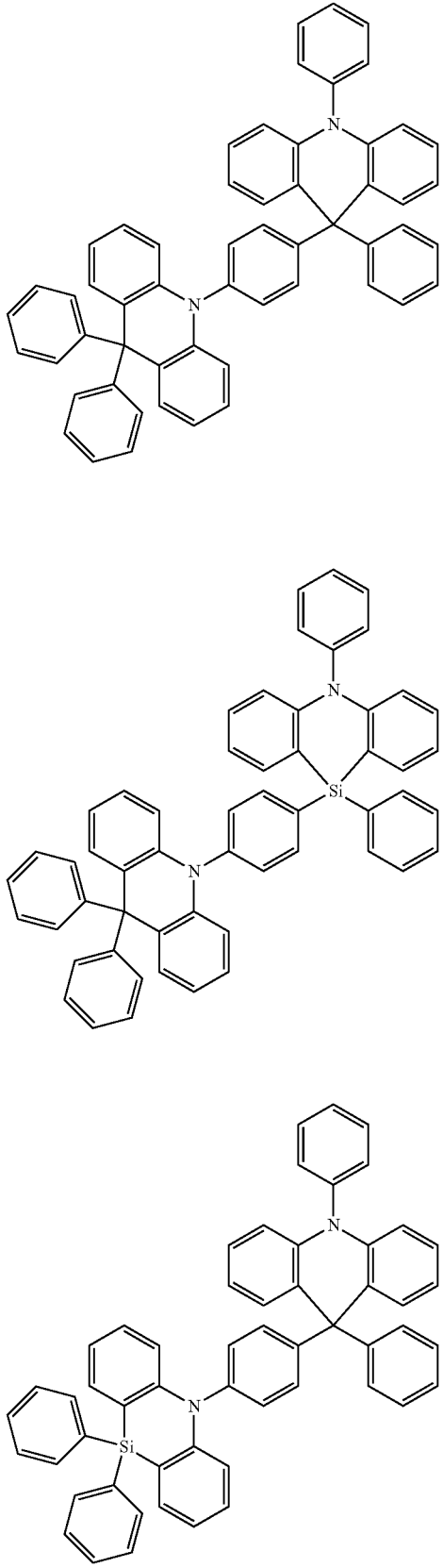

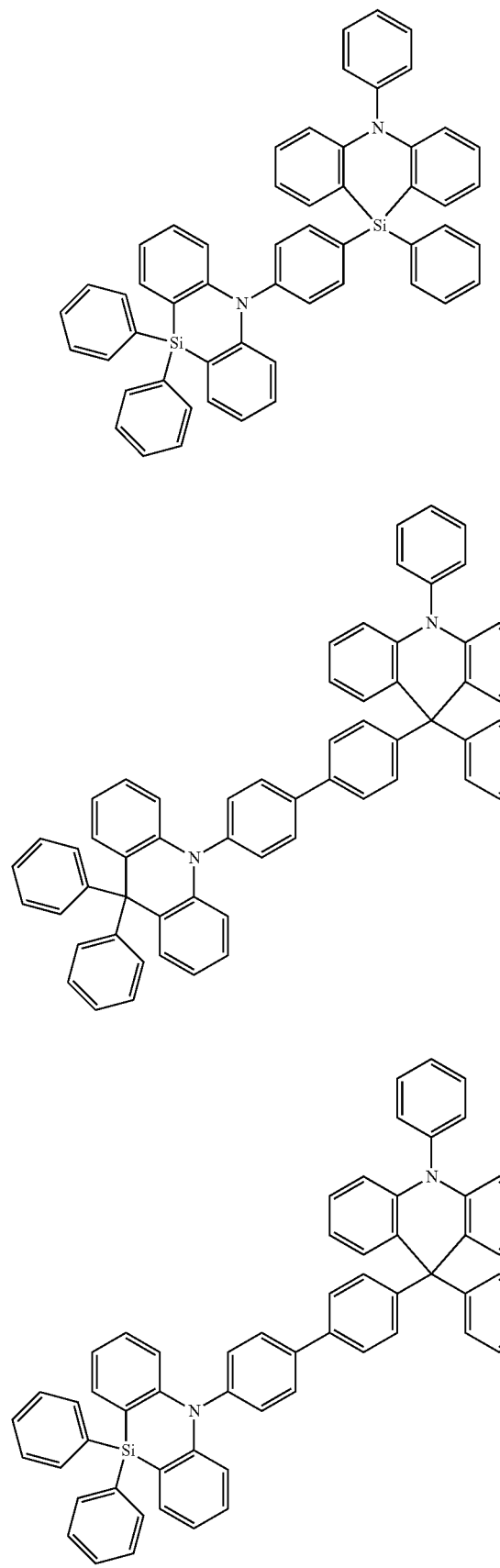
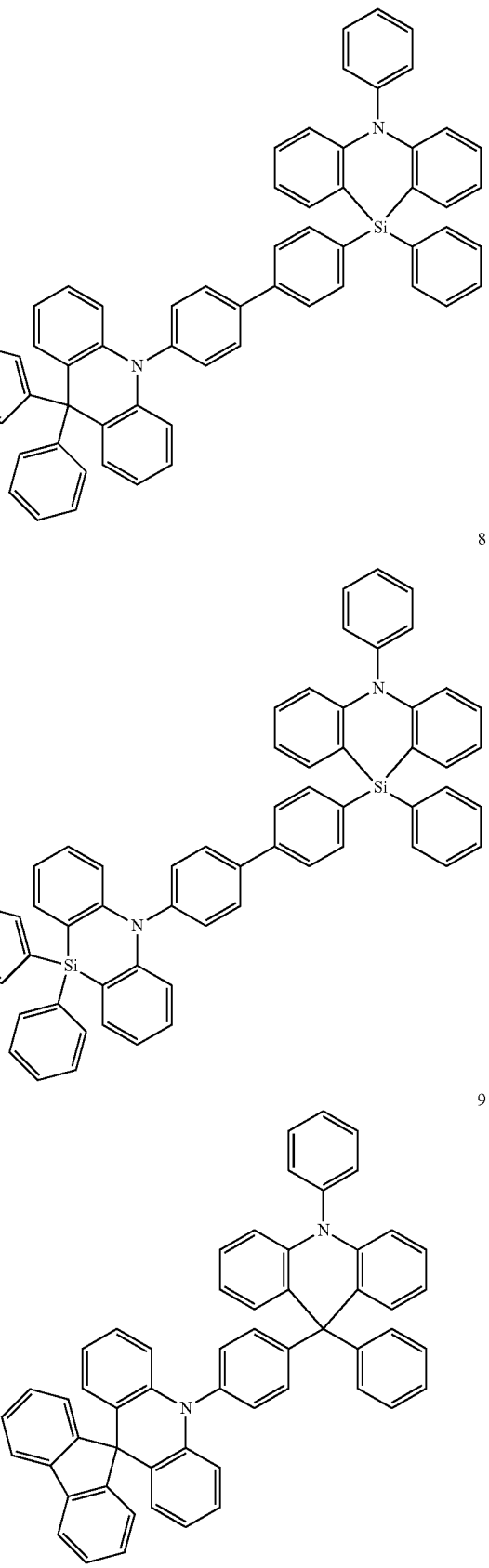

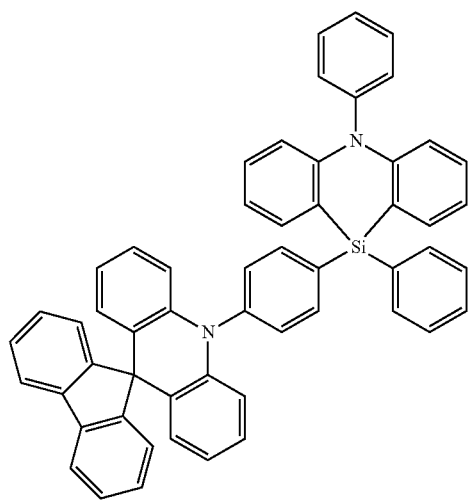
10
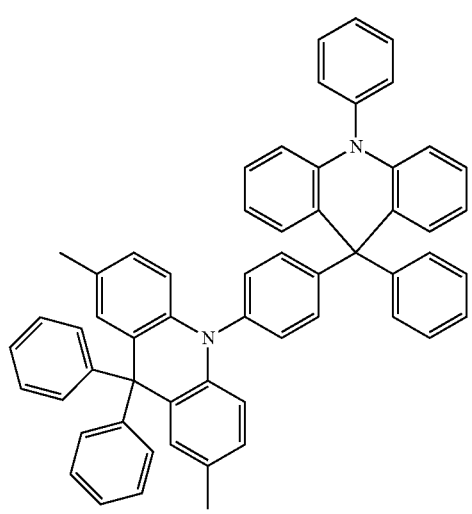
11
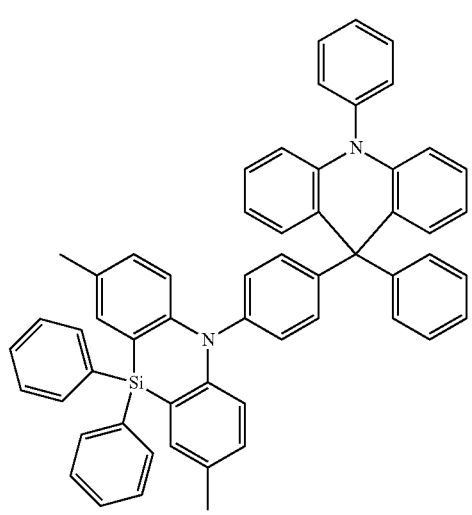
12
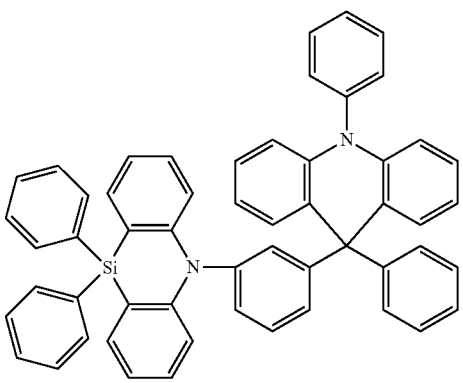
13
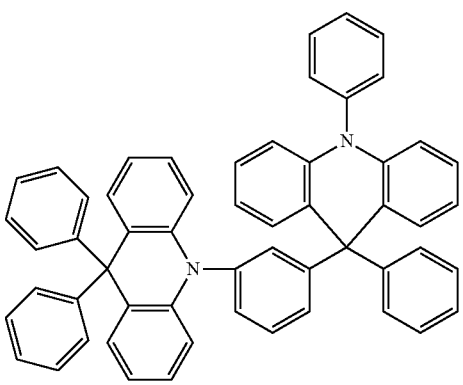
14
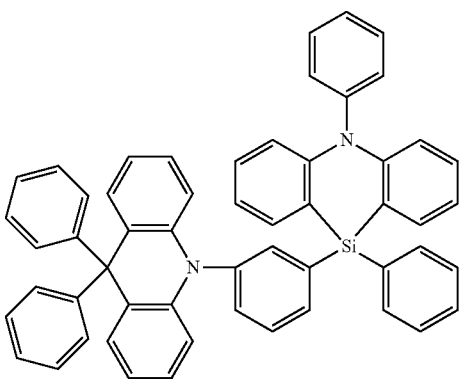
15
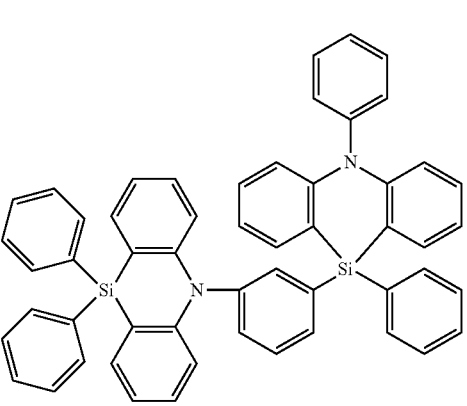
16

17
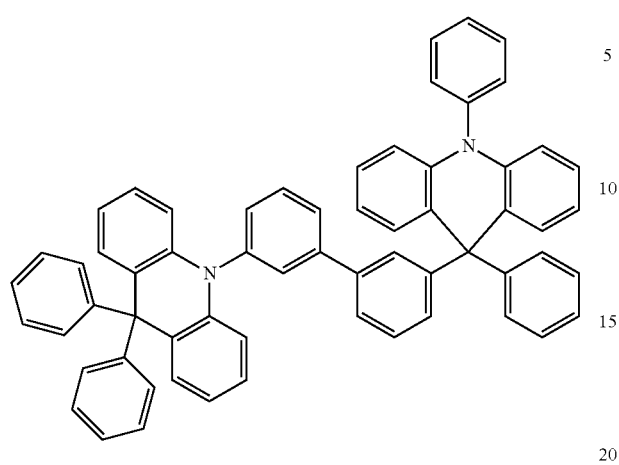
18
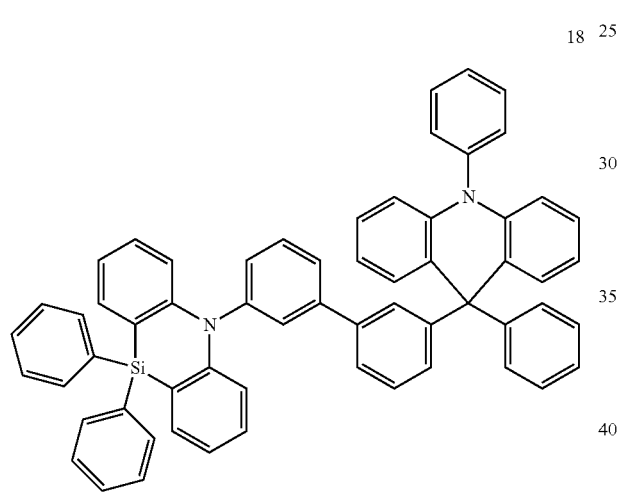
19
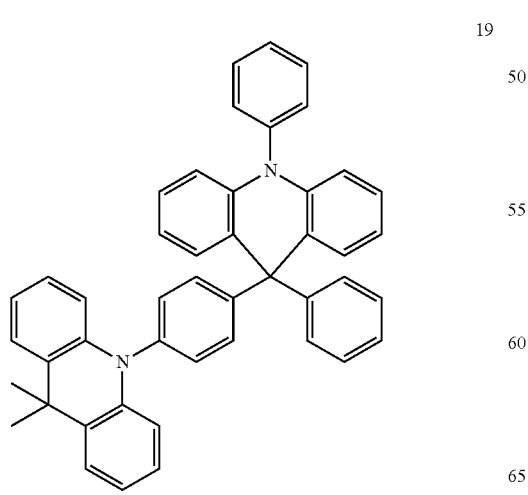
20
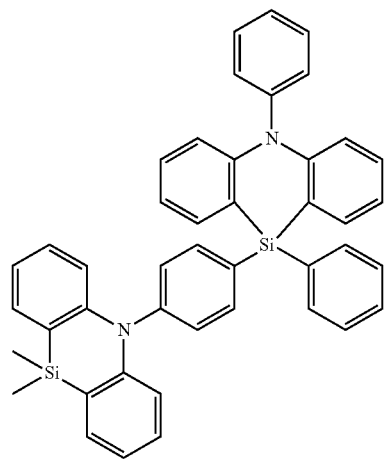
21
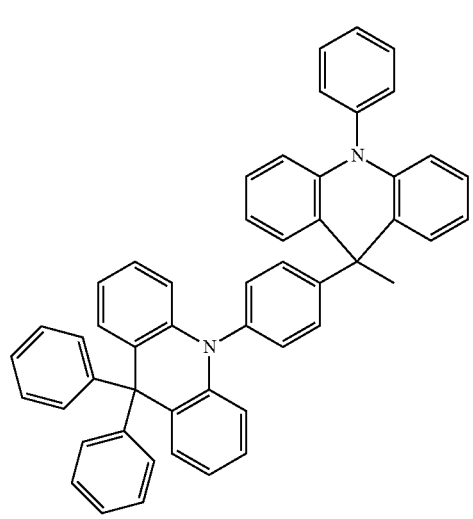
22
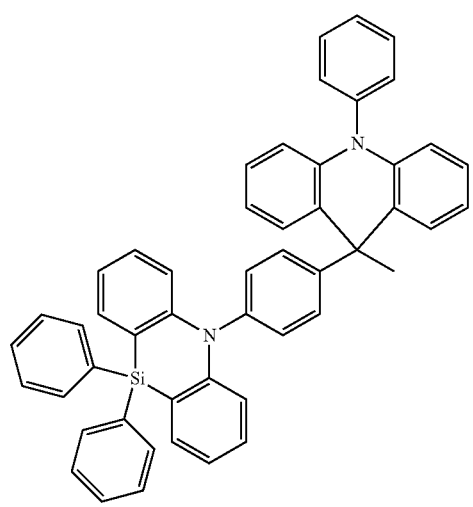

23
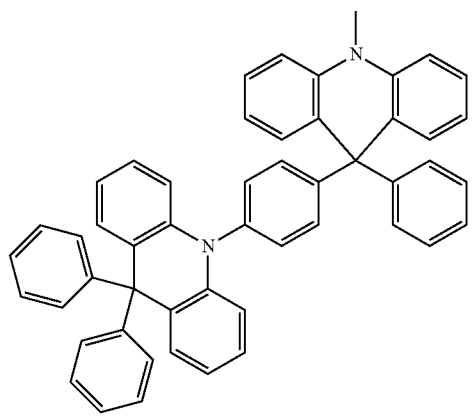
24
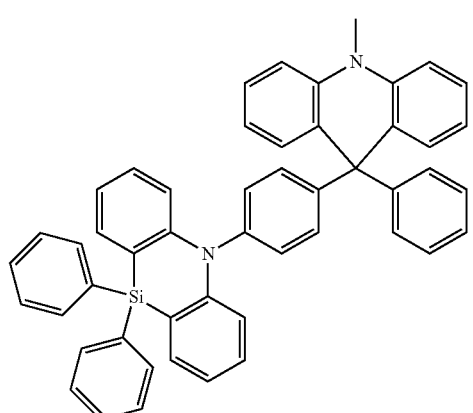
25
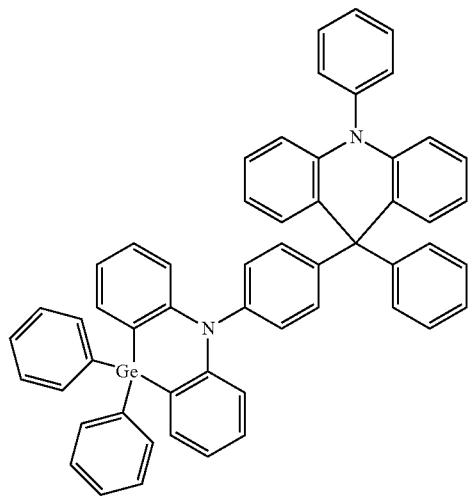
26
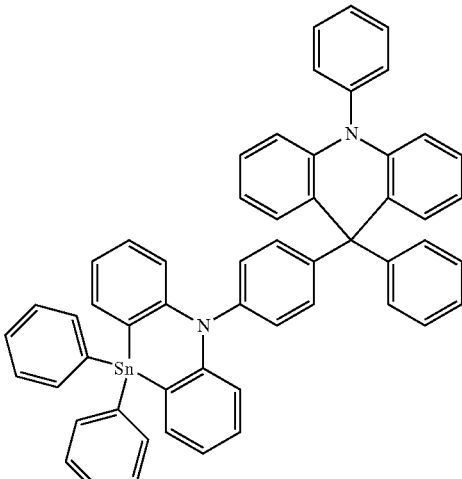
27
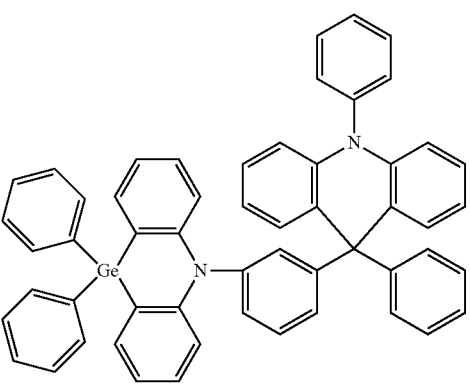
28
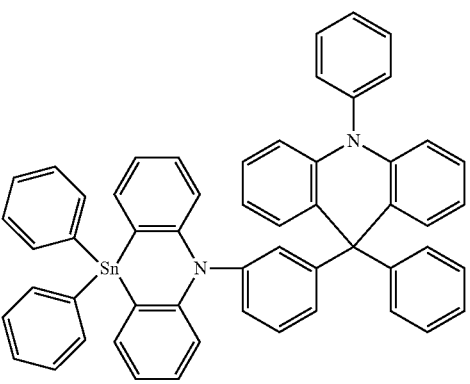
29
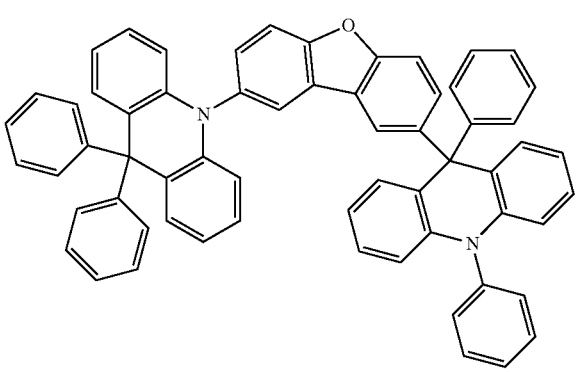

30
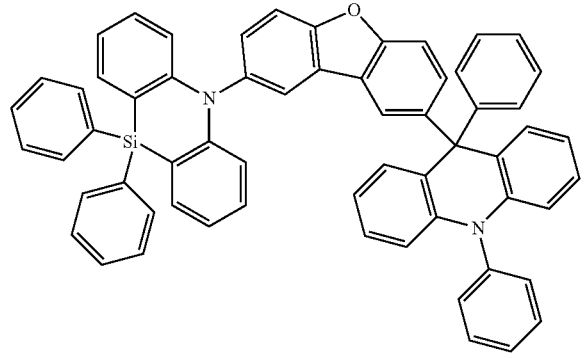
31
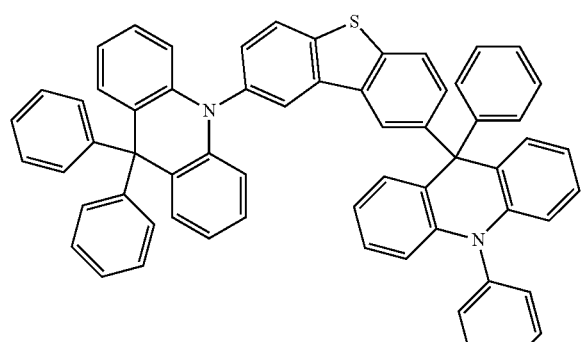
32
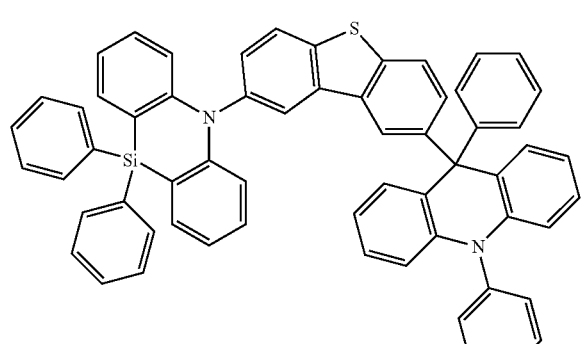
33
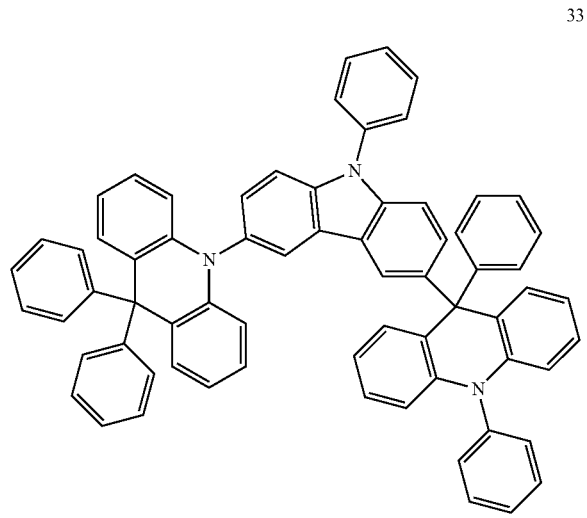
34
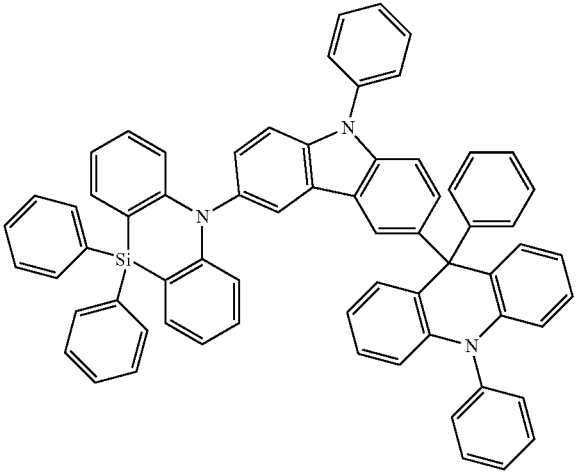
35
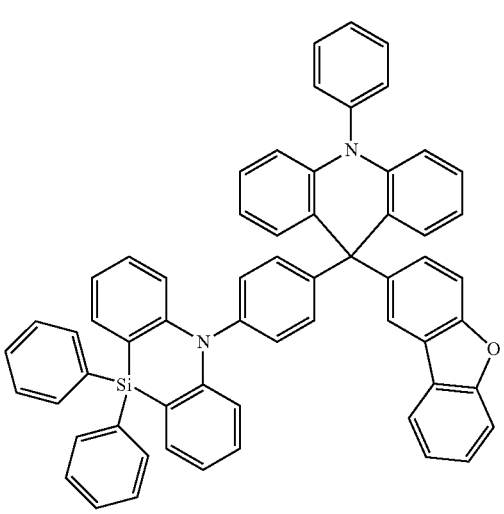
36
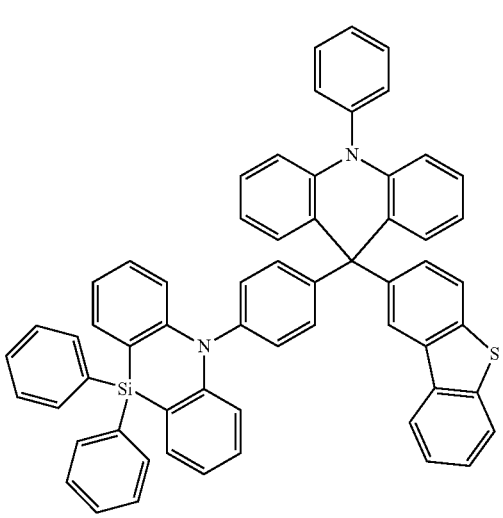

37
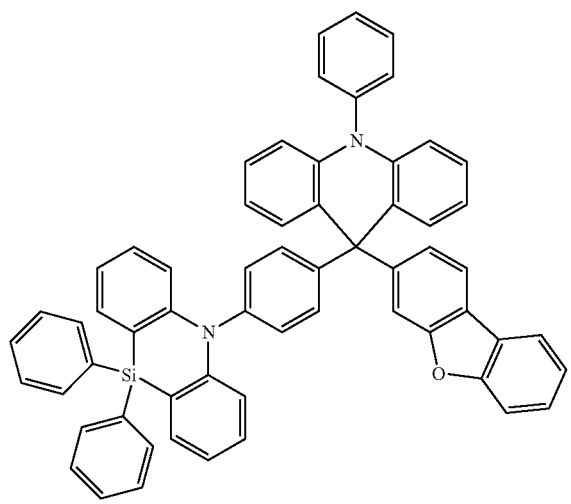
38
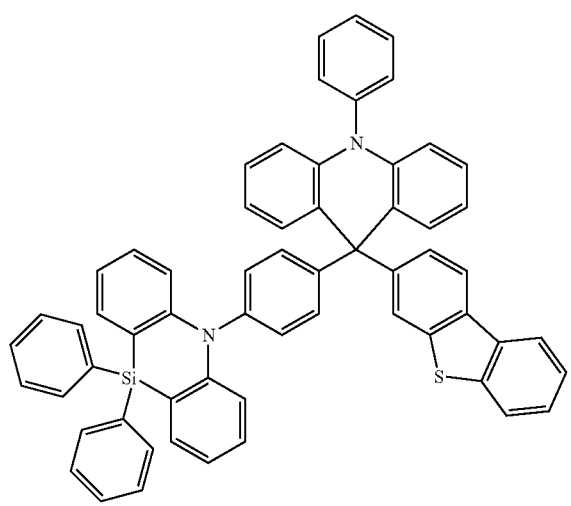
39
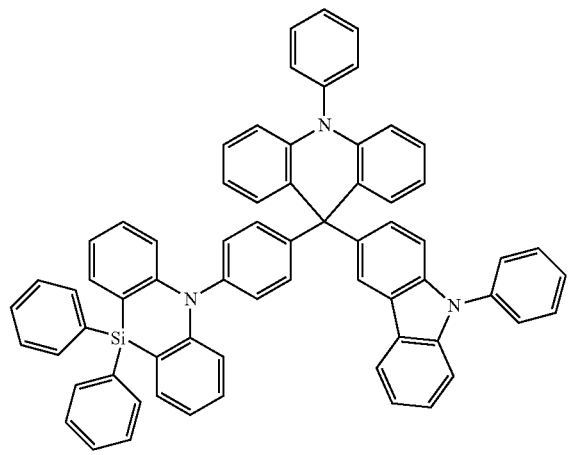
40
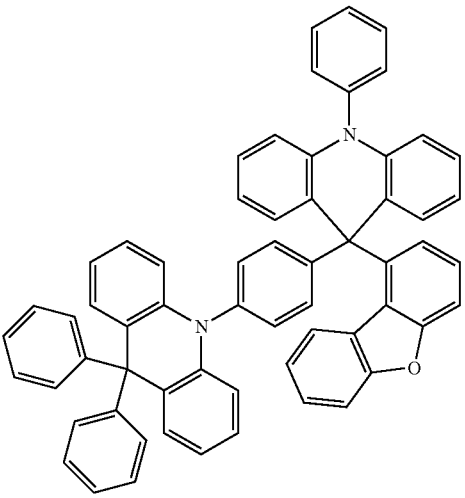
41
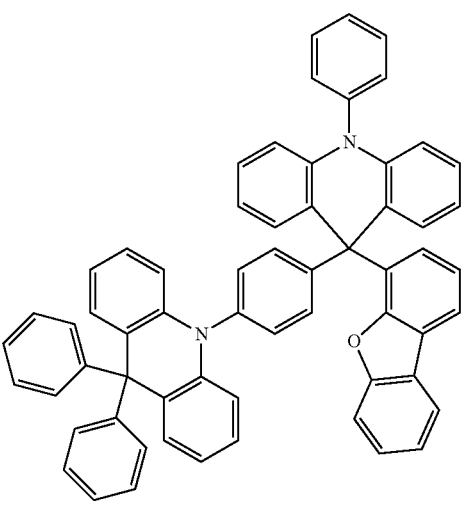
42
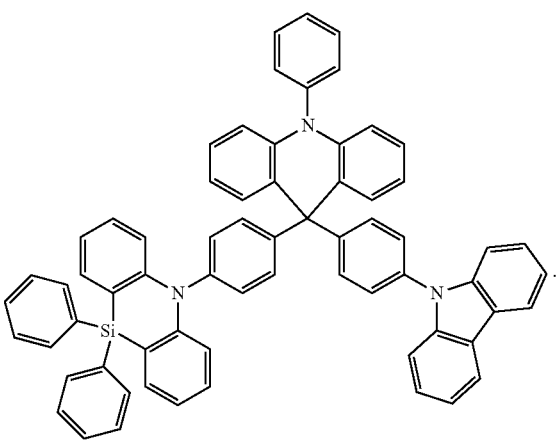
* * * * *